(12) United States Patent
Ghods et al.

(10) Patent No.: US 11,946,877 B2
(45) Date of Patent: Apr. 2, 2024

(54) CONSTRUCTION MATERIAL ASSESSMENT METHOD AND SYSTEMS

(71) Applicants: Pouria Ghods, Gloucester (CA); Rouhollah Alizadeh, Nepean (CA); Andrew Fahim, Ottawa (CA); Sarah De Carufel, Ottawa (CA); Mustafa Salehi, Nepean (CA)

(72) Inventors: Pouria Ghods, Gloucester (CA); Rouhollah Alizadeh, Nepean (CA); Andrew Fahim, Ottawa (CA); Sarah De Carufel, Ottawa (CA); Mustafa Salehi, Nepean (CA)

(73) Assignee: Giatec Scientific Inc., Nepean (CA)

( * ) Notice: Subject to any disclaimer, the term of this patent is extended or adjusted under 35 U.S.C. 154(b) by 702 days.

(21) Appl. No.: 17/052,434

(22) PCT Filed: May 3, 2019

(86) PCT No.: PCT/CA2019/000057
§ 371 (c)(1),
(2) Date: Nov. 2, 2020

(87) PCT Pub. No.: WO2019/210389
PCT Pub. Date: Nov. 7, 2019

(65) Prior Publication Data
US 2021/0063336 A1    Mar. 4, 2021

Related U.S. Application Data

(60) Provisional application No. 62/666,188, filed on May 3, 2018.

(51) Int. Cl.
*G01N 22/00* (2006.01)
*B28C 5/42* (2006.01)
(Continued)

(52) U.S. Cl.
CPC ............ *G01N 22/00* (2013.01); *B28C 5/422* (2013.01); *B28C 7/02* (2013.01); *G01N 3/066* (2013.01);
(Continued)

(58) Field of Classification Search
None
See application file for complete search history.

(56) References Cited

U.S. PATENT DOCUMENTS

2017/0227481 A1*   8/2017   Ghods .................... G01N 27/02

* cited by examiner

*Primary Examiner* — Raul J Rios Russo
*Assistant Examiner* — Carl F. R. Tchatchouang
(74) *Attorney, Agent, or Firm* — Rosenberg, Klein & Lee

(57) ABSTRACT

Globally our environment comprises structures built to perform a meet different requirements including residential, commercial, retail, recreational and service infrastructure. Whilst, millions of tons of construction materials are deployed annually the quality control procedures in many instances have not changed to reflect today's demands. Accordingly, it would be beneficial to provide construction companies, engineering companies, infrastructure owners, regulators, etc. with means to automated testing/characterization of construction materials during at least one of its manufacture, deployment in construction and subsequent infrastructure life. It would be further beneficial for such automated methods to exploit self-contained data acquisition/logging modules allowing them to be employed with ease at the different points in the life cycle of a construction material and/or construction project.

19 Claims, 38 Drawing Sheets

(51) Int. Cl.
*B28C 7/02* (2006.01)
*G01N 3/06* (2006.01)
*G01N 9/24* (2006.01)
*G01N 15/08* (2006.01)
*G01N 23/00* (2006.01)
*G01N 27/06* (2006.01)
*G01N 27/22* (2006.01)
*G01N 33/38* (2006.01)
*G06N 20/00* (2019.01)
*G16C 20/70* (2019.01)
*G16C 60/00* (2019.01)

(52) U.S. Cl.
CPC ........... *G01N 23/00* (2013.01); *G01N 27/221* (2013.01); *G06N 20/00* (2019.01); *G16C 60/00* (2019.02); *G01N 9/24* (2013.01); *G01N 15/08* (2013.01); *G01N 27/06* (2013.01); *G01N 33/383* (2013.01); *G16C 20/70* (2019.02)

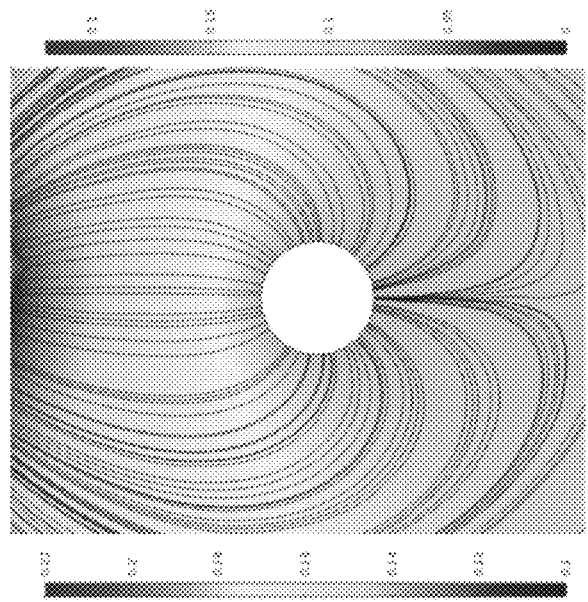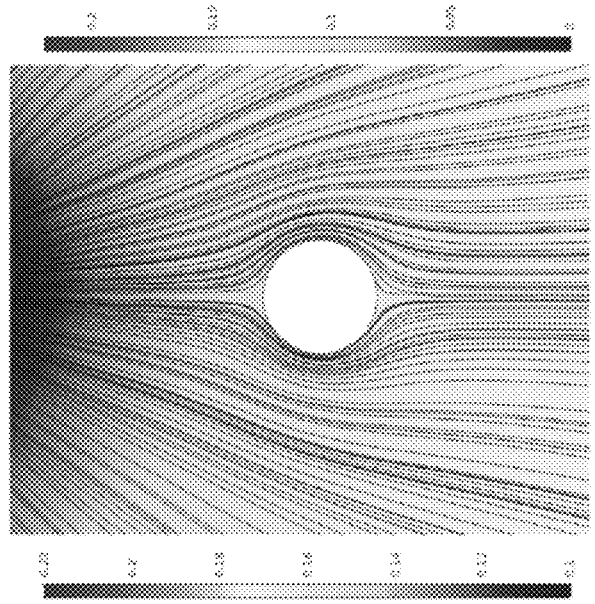
Figure 29
Figure 30

CONSTRUCTION MATERIAL ASSESSMENT METHOD AND SYSTEMS

CROSS-REFERENCE TO RELATED APPLICATIONS

This patent application claims priority as a 371 National Phase entry application of PCT/CA2019/000,057 filed 3 May 2019 entitled "Construction Material Assessment Method and Systems", which itself claims priority from U.S. Provisional Patent application 62/666,188 filed 3 May 2018 entitled "Construction Material Assessment Method and Systems."

FIELD OF THE INVENTION

The present inventions relate to construction material testing and concrete material characterization, and more particularly to electrical methods and compact self-contained electrical sensors with wireless interfaces.

BACKGROUND OF THE INVENTION

Concrete can be one of the most durable building materials and structures made of concrete can have a long service life. Concrete is a composite construction material composed primarily of aggregates, cement, and water. It provides superior fire resistance, compared with wooden construction and can gain strength over time. Further, as it is used as liquid that subsequently hardens it can be formed into complex geometries and may be poured either directly into formworks at the construction sites (so-called ready mix concrete) or employed remotely to pre-build concrete elements and structures. Overall concrete is the most widely used construction material in the world.

There are many types of concrete available, created by varying the proportions of the main ingredients of cement, aggregate, and water as well as reinforcement means, chemical admixtures, and mineral admixtures. In this way or by substitution for the cementitious and aggregate phases, the finished product can be tailored to its application with varying strength, density, or chemical and thermal resistance properties. Examples of chemical admixtures include accelerators to speed up the hardening of concrete, retarders to slow the hardening of concrete for large or difficult pours, air entrainments to enhance freeze-thaw resistance, plasticizers to increase workability, pigments for colour, corrosion inhibitors, bonding agents and pumping aids. Recently the use of recycled materials as concrete ingredients has been gaining popularity because of increasingly stringent environmental legislation.

Concrete is strong in compression, as the aggregate efficiently carries the compression load. However, it is weak in tension as the cement holding the aggregate in place can crack, allowing the structure to fail. Reinforced concrete solves these problems by adding steel reinforcing bars, steel fibers, glass fiber, or plastic fiber to carry tensile loads. Thereafter the concrete is reinforced to withstand the tensile loads upon it. Due to their low cost and wide availability steel reinforcing bar (commonly referred to as rebar) has been the dominant reinforcing material for the past 50 years. However, these steel rebars may corrode whereby the oxidation products (rust) expand and tend to flake, thereby cracking the concrete and reducing the bonding between the rebar and the concrete. Such corrosion may arise from several sources including carbonation when the surface of concrete is exposed to high concentration of carbon dioxide or chlorides, such as when the concrete structure is in contact with a chloride-contaminated environment such as marine exposure environments or concrete pavements exposed to de-icing salts.

Corrosion is an electro-chemical process. Accordingly, the flow rate of the ions between the anode and cathode areas, and therefore the rate at which corrosion can occur, is affected by the resistivity of the concrete. Empirical tests comparing electrical resistivity ($\rho$) measurements with other physical and chemical analysis have generated threshold values with the prior art for determining the wherein if $\rho > 120$ $\Omega \cdot m$ corrosion is deemed unlikely, if $\rho < 80$ $\Omega \cdot m$ then corrosion is fairly certain, and where $80$ $\Omega \cdot m \leq \rho \leq 120$ $\Omega \cdot m$ corrosion is possible. However, these values have to be used cautiously as there is strong evidence that chloride diffusion and surface electrical resistivity are dependent on other factors such as mix composition and age. Further, the electrical resistivity of the concrete cover layer decreases due to increasing concrete moisture content, increasing concrete porosity, increasing temperature, increasing chloride content, and decreasing carbonation depth. However, as an overall industry rule when the electrical resistivity of the concrete is low, the rate of corrosion increases. When the electrical resistivity is high, e.g. in case of dry concrete, the rate of corrosion decreases.

However, it would be evident that for the US alone with over 600,000 concrete bridges and their associated support piers together with 55,000 miles of concrete road surface and billions of tons of concrete in buildings represent a significant measurement hurdle in terms of establishing protocols for rapid testing as well as associating the measurements specifically to particular elements of the physical infrastructure being evaluated. This is without considering all of the other elements of infrastructure built using concrete such as aqueducts, viaducts, railway bridges, pedestrian bridges, underground railways, subways, and buildings for example.

Accordingly, it would be beneficial to provide construction companies, engineering companies, infrastructure owners, regulators, etc. with means to automated testing/characterization of construction materials during at least one of its manufacture, deployment in construction and subsequent infrastructure life. It would be further beneficial for such automated methods to exploit self-contained data acquisition/logging modules allowing them to be employed with ease at the different points in the life cycle of a construction material and/or construction project.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to address limitations within the prior art relating construction material testing and concrete material characterization, and more particularly to electrical methods and compact self-contained electrical sensors with wireless interfaces.

In accordance with an embodiment of the invention there is provided a method comprising:
  embedding a transmission line probe within a construction material;
  performing a time domain reflectometry (TDR) measurement using an electrical signal applied to the transmission line probe to establish an effective dielectric constant for the construction material; and establishing in dependence upon the established effective dielectric constant a predetermined characteristic of the construction material.

In accordance with an embodiment of the invention there is provided a method comprising:

embedding a device within a construction material comprising at least a microwave circuit for generating and processing microwave signals, a microprocessor, a battery, a first antenna for transmitting a microwave signal generated by the microwave circuit, a second antenna for receiving the microwave signal from the first antenna, and a wireless interface operating according to a predetermined wireless protocol for transmitting data from the device;

establishing in dependence upon timing information relating to microwave signals transmitted by the first antenna and received by the second antenna an effective dielectric constant for the construction material;

establishing in dependence upon the established effective dielectric constant a predetermined characteristic of the construction material; and transmitting from the device at least one of the effective dielectric constant and the determined predetermined characteristic.

In accordance with an embodiment of the invention there is provided a method comprising:

embedding a device within a construction material comprising at least a microprocessor, a battery, a wireless interface operating according to a predetermined wireless protocol for transmitting data from the device, and a resistivity module comprising at least a porous material in contact with the construction material;

allowing the porous material to reach equilibrium with a pore solution within pores in the construction material;

measuring the resistivity of the porous material with the pore solution of the construction material; and determining in dependence upon the resistivity a measurement of the pore solution conductivity.

In accordance with an embodiment of the invention there is provided a method comprising:

embedding a device within a construction material, the device comprising at least a microprocessor, a battery, a wireless interface operating according to a predetermined wireless protocol for transmitting data from the device, and an acoustic receiver acoustically in contact with the construction material;

receiving an acoustic signal from another device embedded within the construction material or another device external to the construction material; and establishing in dependence upon timing information relating to the received acoustic signal an acoustic velocity for the intervening construction material between the another device and the device;

determining in dependence upon the acoustic velocity a density measurement of the construction material and therein a determination of air content within the construction material.

In accordance with an embodiment of the invention there is provided a method comprising:

embedding a device within a construction material, the device comprising at least a microprocessor, a battery, a wireless interface operating according to a predetermined wireless protocol for transmitting data from the device, and an acoustic transmitter acoustically in contact with the construction material;

transmitting an acoustic signal to another device embedded within the construction material or another device external to the construction material;

establishing in dependence upon timing information relating to the acoustic signal an acoustic velocity for the intervening construction material between the device and the another device; and determining in dependence upon the acoustic velocity a density measurement of the construction material and therein a determination of air content within the construction material.

In accordance with an embodiment of the invention there is provided a method comprising:

providing a sensor upon an inner surface of a drum forming part of a concrete truck, the sensor providing an output in dependence upon the conductivity of any material in contact with the sensor;

loading a construction material into the drum and rotating the drum during transportation of the construction material from a point of loading and a point of deployment;

monitoring the output of the sensor during rotation of the drum; and establishing in dependence upon the monitored sensor output at least one of a number of rotations of the drum and a material property of the construction material within the drum.

In accordance with an embodiment of the invention there is provided a device comprising a module comprising a controller, a pulse generator, a pulse detection circuit, a timing circuit, and a wireless interface; and a first probe; wherein the controller executes a process comprising:

generating a first electrical pulse with the signal generator;

determining receipt of a second electrical pulse by the pulse detection circuit;

determining an effective dielectric constant in dependence upon a time difference between the generation of the first electrical pulse and receipt of the second electrical pulse established by the timing circuit; and establishing in dependence upon the established effective dielectric constant a predetermined characteristic of the construction material.

In accordance with an embodiment of the invention there is provided a device comprising:

a body;

a porous material disposed within a predetermined portion of the body;

a control circuit disposed within the body;

a first electrical contact coupled to the control circuit and the porous material at a first predetermined location;

a second electrical contact coupled to the control circuit and the porous material at a second predetermined location; wherein a predetermined portion of the porous material is exposed to an environment surrounding the device.

In accordance with an embodiment of the invention there is provided a device comprising:

a body;

a cavity within a predetermined portion of an exterior of the body;

a control circuit disposed within the body;

a first electrical transducer coupled to the control circuit and disposed at a first predetermined location within a first surface of the cavity;

a second electrical transducer coupled to the control circuit and disposed at a second predetermined location within a second surface of the cavity facing the first electrical transducer; wherein the control circuit determines a characteristic of an environment surrounding the device.

In accordance with an embodiment of the invention there is provided a system comprising:

a plurality of devices, each device comprising:
a body;
a control circuit disposed within the body;
a plurality of electrical transducers, each electrical transducer coupled to the control circuit and disposed at a predetermined location within an exterior surface of the device; wherein
a first device of the plurality of devices generates a plurality of first signals within an environment surrounding the plurality of devices, each first signal generated by an electrical transducer of the first device of the plurality of devices;
a second device of the plurality of devices receives a second signal, the second signal received from the environment surrounding the plurality of devices and generated by an electrical transducer of the first device of the plurality of devices; and
each electrical transducer is at least one of a microwave transmitter and a microwave receiver.

In accordance with an embodiment of the invention there is provided a method comprising:

establishing a specification relating to a construction material;
establishing a geographical location relating to a deployment of the construction material;
establishing contractual requirements relating to the deployment of the construction material;
establishing a projected time for the deployment of the construction material;
extracting historical environmental data for the location of the deployment of the construction material at the projected time;
extracting historical performance data relating to previous deployments of the construction material with the established specification;
analyzing the extracted historical environmental data and historical performance data with respect to the contractual requirements.

In accordance with an embodiment of the invention there is provided a method comprising:

retrieving first data relating to a concrete mixture;
retrieving second data relating to the concrete mixture;
extracting performance data from the second data;
processing the first data and the extracted performance data within one or more machine learning algorithms;
establishing one or more influences of the first data upon the second data; and
establishing an adjustment to the concrete mixture; wherein
the adjusted concrete mixture is established to enhance a characteristic of the performance of the adjusted concrete mixture relative to the concrete mixture; and
the characteristic is one of long term strength, reduced chloride ion content, reduced time for formwork removal, and reduced ambient environmental sensitivity.

In accordance with an embodiment of the invention there is provided a method comprising:

applying a narrow electrical pulse to a pair of first electrodes in contact with an area of concrete containing a rebar;
measuring a time dependent voltage response from a pair of second electrodes in line with and between the pair of first electrodes and in contact with the area of concrete containing a rebar;
fitting the measured time dependent voltage response to a theoretical transient to establish a fitted transient function;
determining constants of the fitted transient function; and
determining one or more electrical equivalent circuit elements of an equivalent circuit model of the concrete containing the rebar.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 29 depicts the high frequency current path after 1 μs of current application for a simulated structure employing passive reinforcements established through simulations;

FIG. 30 depicts the low frequency current path after 1 μs of current application for a simulated structure employing passive reinforcements established through simulations;

DETAILED DESCRIPTION

Figure 1:
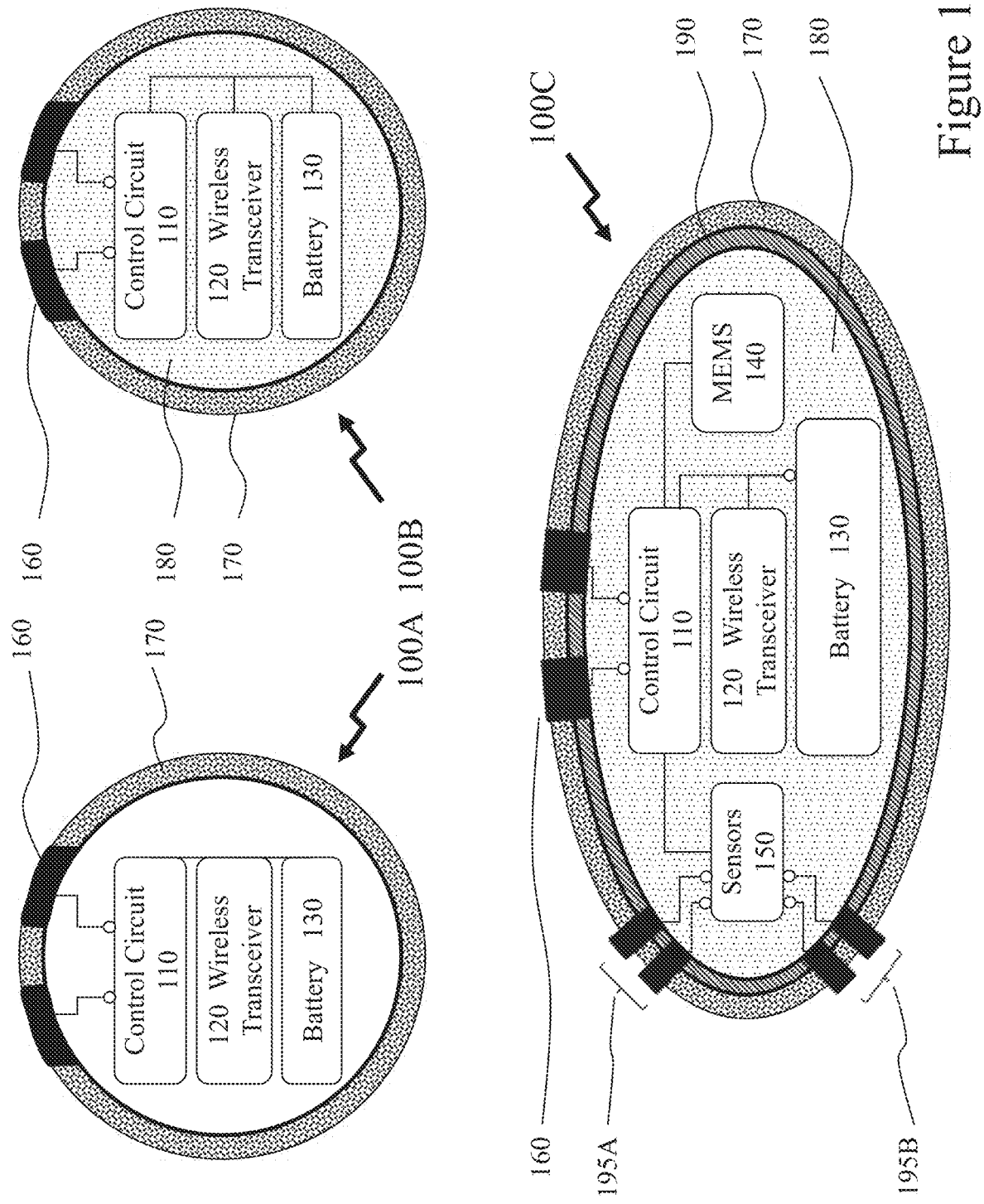
FIG. 1 depicts examples of embedded sensors for data logging concrete properties from initial mix through pouring, curing, and subsequently according to an embodiment of the invention.

The present invention is directed to construction material testing and concrete material characterization, and more particularly to electrical methods and compact self-contained electrical sensors with wireless interfaces.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A "portable electronic device" (PED) as used herein and throughout this disclosure, refers to a wireless device that requires a battery or other independent form of energy for power. This includes devices including, but not limited to, cellular telephone, smartphone, personal digital assistant (PDA), portable computer, pager, portable multimedia player, portable gaming console, laptop computer, tablet computer, and an electronic reader.

A "fixed electronic device" (FED) as used herein and throughout this disclosure, refers to a wired and/or wireless device used which is dependent upon a form of energy for power provided through a fixed network, e.g. an electrical mains outlet coupled to an electrical utilities network. This includes devices including, but not limited to, portable computer, desktop computer, computer server, Internet enabled display, mainframe, and server cluster. Such PEDs and FEDs supporting one or more functions and/or applications including, but not limited to, data acquisition, data storage, data analysis, communications, and Internet/Web interface.

A "machine learning algorithm" as used herein and throughout this disclosure, refers to algorithms and/or statistical models for a computer systems used to effectively perform a specific task without using explicit instructions, relying on patterns and inference instead. Such machine learning algorithms may exploit a mathematical model based on sample data, known as "training data", in order to make predictions or decisions without being explicitly programmed to perform the task. Such computer systems may include, but not be limited to, artificial neural networks, support vector machines, Bayesian networks, and genetic algorithms. Such computer systems and machine learning algorithms may exploit, for example, feature learning, sparse dictionary learning, anomaly detection, decision trees, and association rules in combination with, for example, supervised and/or semi-supervised learning, unsupervised learning, and reinforcement analysis.

Sensor Configurations

In order to provide construction material manufacturers, construction companies exploiting construction materials, designers, engineers, infrastructure owners, and regulators with improved data acquisition for enhanced analytics, real time monitoring, current and projected construction material characteristics, and analytics the inventors have established designs for embedded sensors or what the inventors refer to as "SMArt rocKs" (SMAKs, namely sensors) wherein SMAKs may be embedded into construction materials at various points in their life cycle from their manufacture, deployment, and post-deployment. The inventors describing several SMAK concepts within U.S. Patent Publication No. 2017/0,284,996 entitled "Embedded Wireless Monitoring Sensors" and U.S. Patent Publication No. 2017/0,108,456 entitled "Electrical Methods and Systems for Concrete Testing."

As such these embedded sensors, may for example, be added to a concrete batch loaded onto a concrete truck at a batching plant. It is therefore possible to "tag", i.e. load into, the embedded sensor information relevant to the mix as well as delivery data etc. This information as well as other measurements made by the embedded sensors during the transportation, pouring, and placement can be accessed by wireless interface by the end user during delivery, once the concrete is delivered to the construction site, as it is poured, and during its curing, maturation processes.

As such the tagging of the SMAKs may include, but not be limited to, information such as batch identity, truck identity, date, time, location, batch mix parameters, etc. but may also include specific information such as the maturity calibration curves for the mix established by the manufacturer. Accordingly, depending upon the degree of complexity embedded into the SMAK such data may be either retrieved for remote storage and subsequently used or it may be part of the SMAKs processing of electrical measurement data such that calibration data of the concrete mix is already factored into the data provided by the SMAKs. Accordingly, the SMAKs may be added to the concrete at a manufacturing point according to the construction material. For example, this may be a concrete batching point, a production line for gypsum based sheets (namely plaster board, drywall, gypsum board), a production line for wood or fiber based products such as particle board, low density fiberboard, medium density fiberboard, etc. SMAKs may be loaded tagged already, tagged during addition, or tagged after addition. Subsequently upon delivery and employment at the construction site the SMAKs may be read for information regarding their manufacture, delivery process, etc.

Accordingly, once deployed the SMAKs may be read for acquired information from the one or more sensors within the SMAK and then subsequently, depending upon the battery—power consumption etc., periodically read for lifetime data of the construction material. In each instance the acquired data may be acquired wirelessly and stored on a user's PED or it may then be pushed to a network and therein to one or more servers. For devices wirelessly interrogating the SMAKs these may be executing a software application which presents to the user concrete parameter data either as provided from the SMAK(s) directly using the calibration curves stored within or upon the device using calibration curve data stored within the SMAK but not processed by it, stored within the device or retrieved from the data stored upon a remote server. As depicted the SMAKs may be interrogated with a PED or alternatively the data stored upon the remote server may be interrogated and accessed by a PED.

A SMAK may be enabled by a wireless signal, by a vibration measured by the SMAK exceeding a threshold, via an electrical circuit forming part of the SMAK being completed, an increase in humidity beyond a threshold, a decrease in light, etc. Accordingly, SMAKs according to embodiments of the invention may support tagging with information at deployment, the embedding of calibration data such as concrete maturity calibration curves in the sensor, and the acquisition of sensor data.

Based upon the combination of SMAKs within the construction material, their wireless interrogation, and mobile/cloud based software applications other technical enhancements may be implemented, including for example:

Weather forecast API, such that the ambient temperature prediction in conjunction with current concrete data can be used to predict/project the strength identifying quality problems earlier;

Automatic detection of construction material deployment, e.g. for concrete from an electrical connection being completed once the concrete is poured or change in the pressure, humidity, light etc. or a characteristic vibration from a nail gun or other tool for plasterboard, particle board etc.;

Tagging the sensor using NFC with smartphone;

Data integrity and management on remote servers;

Data analytics and/or artificial intelligence on data analysis as the SMAK manufacturer may acquire data from a large number of job sites allowing additional analytics, reporting, alarms etc.;

A SMAK manufacturer may establish so-called "big data" on construction material properties and construction material cycles/processes across a large number of job sites, geographic regions, time frames etc. allowing them to provide feedback from their server based processes to the end user;

Push notifications, such as for example the concrete contractor is notified when is the time to remove the formwork based upon actual concrete curing data; and Heat optimization wherein for example closed loop feedback of the temperature history and strength development can be employed to optimize heating employed in cold climates to ensure the concrete slabs gain sufficient strength within a specific period.

In addition to measuring, for example, temperature, DC electrical conductivity, and AC electrical conductivity it would be evident that additional parameters as discussed and described within US 2017/0,284,996 and US 2017/0,108, 456 may be monitored including moisture content, concrete relative humidity, pH, mixture consistency, workability (slump), hydraulic pressure, segregation, cracking, penetration of external ions into concrete, dispersion of fibers, and dispersion of chemical additives and supplementary cementitious materials.

Accordingly, referring to FIG. 1 there are depicted first to third SMAKs 100A to 100C according to embodiments of the invention as described within US 2017/0,284,996 and US 2017/0,108,456. Referring to first SMAK 100A contacts 160 are formed within outer shell 170 defining an interior within which are disposed a control circuit 110 comprising a microprocessor with associated memory (hereinafter, processor) and associated electrical circuits required to power, drive, measure the electrical signals generated by the sensors 150 etc. The control circuit 110 being coupled to a wireless transceiver 120 and a battery 130. Accordingly, electrical conductivity (for example) between the contacts 160 may be monitored (e.g. arising from water within a concrete mix), processed with the control circuit 110, stored and then subsequently transmitted via wireless transceiver 120 when a link is established to a portable electronic device (PED) such as smartphone, tablet PC, or dedicated device. The shell 170 may be formed from a variety of materials, including but not limited to, metals (from which the contacts are isolated by insulating rings etc.), ceramics (e.g. alumina, zirconia, etc.), composites (e.g. fiber reinforced polymer, ceramic matrix composites, concrete, glass-reinforced plastic) and plastics (e.g. short-fiber thermoplastics, long-fiber thermoplastics, thermosetting plastics, filled plastics, synthetic rubber, elastomer, etc.).

Second SMAK 100B depicts essentially the same construction as SMAK 100A except that the interior of the shell is now filled with a filler 180. Second filler material 180 may be a resilient filler 180 surrounded by a soft shell 170 such as synthetic rubber or elastomer, for example, or alternatively the filler 180 may be semi-resilient in combination with a resilient shell 170. Such semi-resilient fillers 180 may include thermosetting resins, catalyzed resins, cured silicone gels, etc. used in conjunction with a shell 170 formed from a plastic or rubber, for example.

Third SMAK 100C exploits the same filler 180 with shell 170 but now an intermediate casing 190 is disposed between the outer shell 170 and the inner filler 180. For example, casing 190 may be an impermeable membrane, e.g. Gore-Tex™, that limits moisture ingress to the SMAK 100C but allows air or gas permeability. Further, SMAK 100C now comprises in addition to the control circuit 110, wireless transceiver 120, and battery 130 additional sensors 160 which are coupled to first and second SENsor INTerfaces (SENINTs) 195A and 195B which together with contacts 160 provide external sensing data to the control circuit 110. Further a microelectromechanical system (MEMS) 140 within the SMAK 100C provides data to the control circuit 110 wherein the MEMS 140 may comprise, for example, an accelerometer such as a one-dimensional (1D), two-dimensional (2D) or three-dimensional (3D) accelerometer providing data relating to motion, shock, etc.

Within different embodiments of the invention some SENSINTs may have direct exposure to the external environment whereas others may be indirect or via a barrier material etc. or have a characteristic that varies in response to an external environmental aspect. Sensors may include, but are not limited to, temperature, electrical resistance, pressure, light, acceleration (e.g. MEMS accelerometer), vibration (e.g. MEMS sensor), humidity (e.g. capacitive sensor barriered with a vapour barrier to prevent direct fluid contact), pH (e.g. ion sensitive field effect transistor—ISFET pH sensor), ion content (to detect externally penetrating chemicals or materials), chloride content, microphone or acoustic sensor (to detect crack propagation), gas sensor (e.g. nitrogen, oxygen to detect air within cracks propagating to the surface of the concrete), corrosion detectors, visible optical sensors, ultraviolet optical sensors, and infrared optical sensors. More advanced sensors may provide dedicated hardware, functionality, and software to enable more advanced techniques such as nuclear magnetic resonance, electrochemical impedance spectroscopy, X-ray diffraction, optical spectrometry, thermogravimetric analysis, a half cell, etc. as well as corrosion resistance etc.

Time Domain Reflectometry Water Determination

Within construction materials such as concrete which are deployed in liquid form and subsequently cure and harden knowledge of the water content can provide important information regarding the construction material's manufacturing, curing, hardening, etc. Accordingly, the inventors have established sensors such as those depicted in FIGS. 2B, 2C, 3A and 3B respectively for measuring the water content within a construction material exploiting the measurement of the construction material's dielectric constant.

The propagation velocity of electromagnetic waves within a medium is a function of the dielectric constant of the medium. Concrete is a heterogeneous material, which can be simply decomposed into three phases: a solid phase, including all the solid components (aggregates, hydrated components, anhydrous cement, etc.); a gaseous phase (air); and a liquid phase, which is a conductive solution. The sum of the volume fractions of air and saline solution equals the total porosity of the material. The relative permittivity of the solid phase is a real number usually lying between 3 and 5, depending on the mineral composition. The real value of the solid phase permittivity indicates that solid components present negligible losses. The mixture of solid and gaseous phases (dry concrete) gives a non-dispersive medium, i.e. the permittivity is not frequency dependent. The existence of dispersion in concrete results only from the presence of free water in the pores and its significance is governed by the volumetric water content.

Further, as the dielectric constant of water is significantly higher than that of air or the solid skeleton of concrete, i.e. the cement paste and aggregates, changes in water content can be detected through the change in dielectric constant of the concrete medium at a single frequency. Frequencies for performing a measurement of the dielectric constant can in principle lie within the frequency range 10 kHz to 95 GHz. However, for cost, footprint, etc. typical operating frequencies are more likely to be within the frequency range 10 kHz-3 GHz, 10 kHz-1 GHz, or 10 kHz-100 MHz.

Figure 2A:
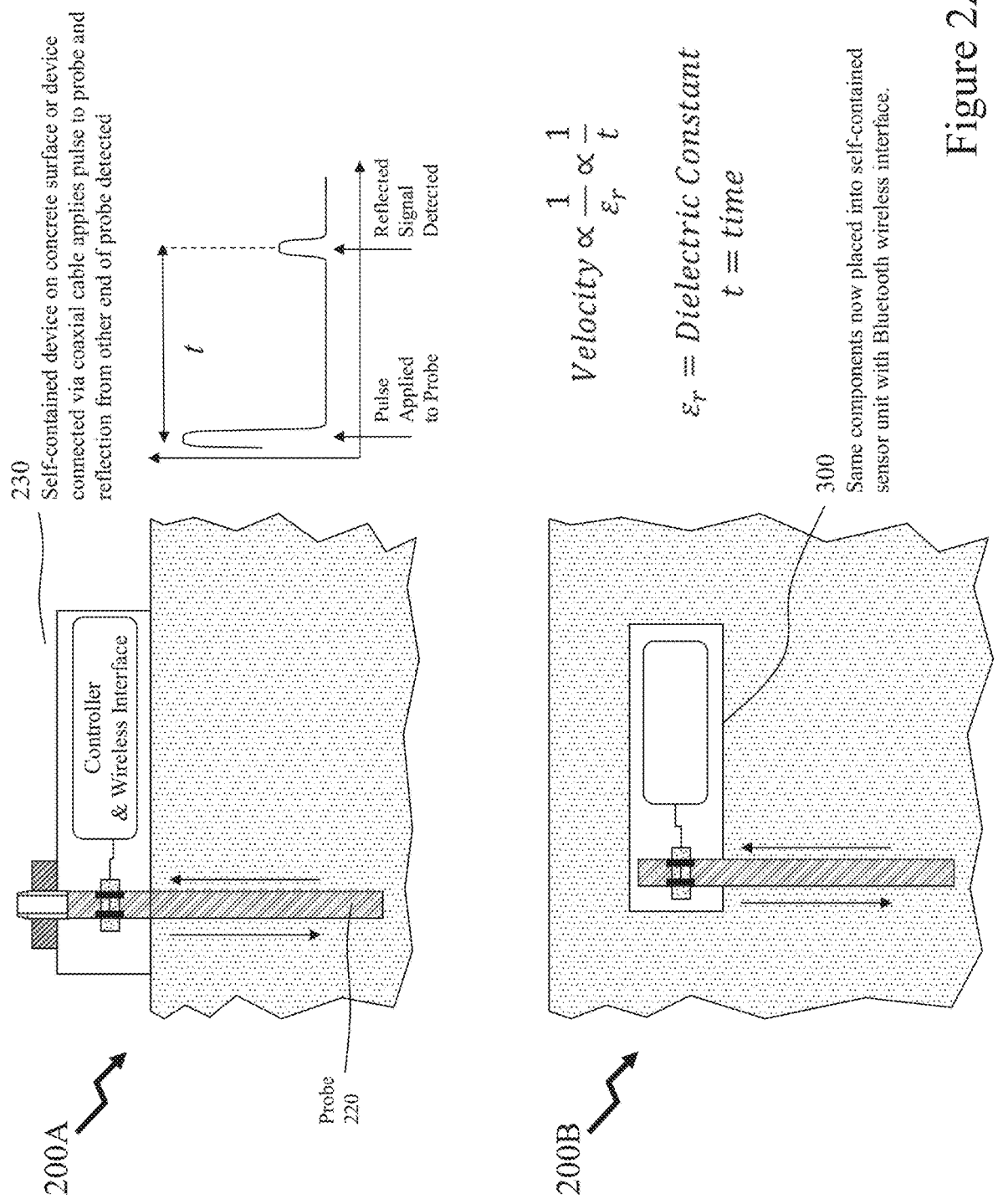
FIG. 2A depicts exemplary schematics of partially embedded and fully embedded geometries for time domain measurements according to embodiments of the invention.

Referring to FIG. 2A there are depicted first and second configurations 200A and 200B respectively in respect of time domain sensor embedding. Within first configuration 200A which is described further in FIG. 2B the probe 220 is partially embedded within the construction material, e.g. concrete, such that the measurement electronics 230 is attached externally to the construction material. This being either permanently attached or demountably attached within embodiments of the invention. Accordingly, a pulse is applied at a point in time and travels down the probe wherein it is reflected back and the overall round-trip time, t, is measured. As the velocity of the pulse within the probe is inversely proportional to this time then the dielectric constant of the construction material can be determined and therein properties of the construction material. In contrast in second configuration 200B the probe is completely embedded within the construction material as is the sensor 300 of which it forms part. This being described further in FIG. 3A. The measurement electronics may comprise, for example, a microprocessor or controller, a pulse generator for generating the electrical pulse, a pulse detection circuit for detecting the returned electrical pulse, and a timing circuit to determine the timing between the generation of the electrical pulse and its subsequent receipt.

Figure 2B:
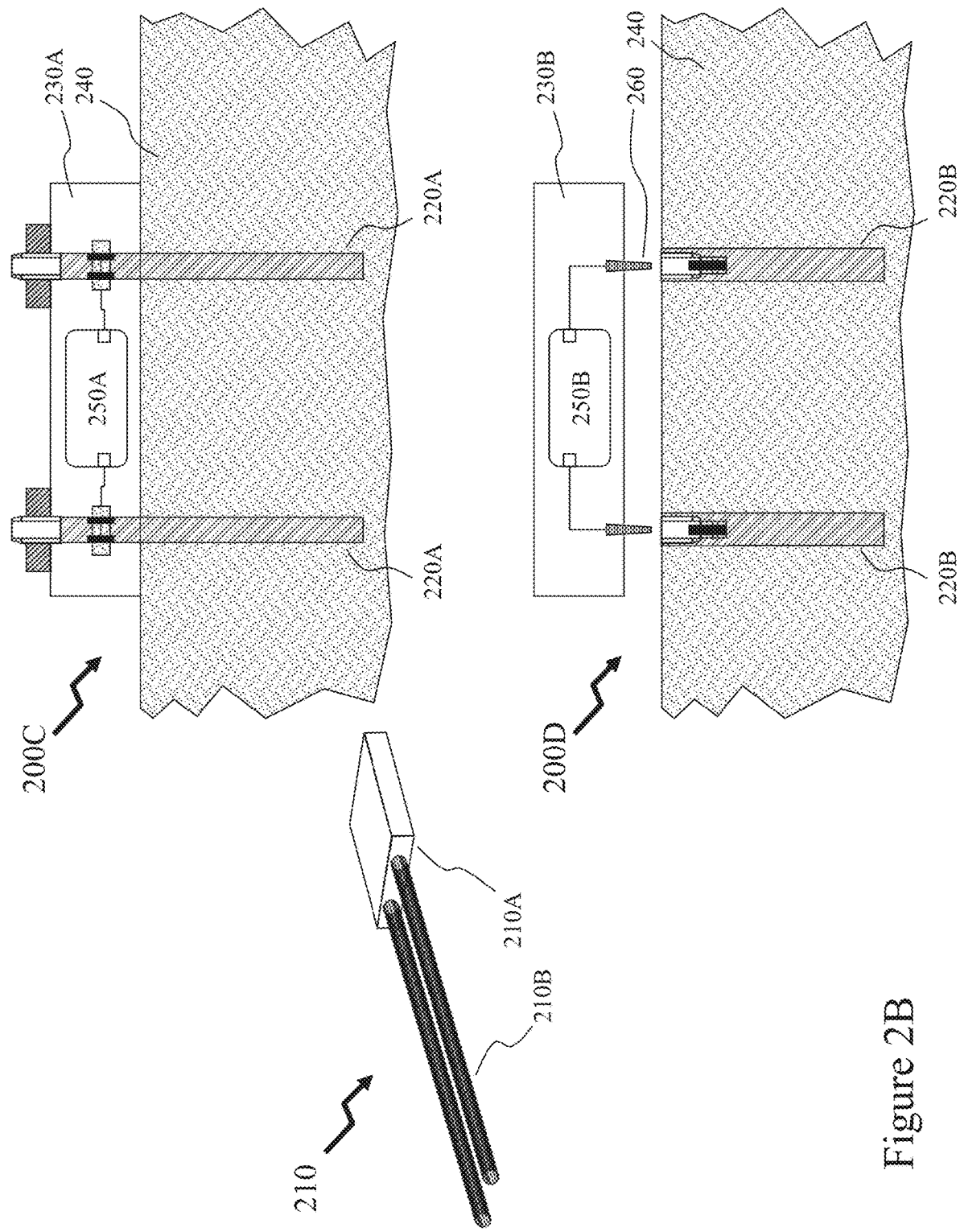
FIGS. 2B and 2C depict exemplary embedded sensor concepts with external access according to embodiments of the invention for providing time domain measurements to establish water content within concrete.

Accordingly, referring to FIG. 2B there are depicted first cross-section 200C and second cross-section 200D with respect to embodiments of the invention for a transmission line probe assembly 210 comprising a pair of conductors 210A and a housing 210B. Optionally, the conductors 210A may be isolated and combined to form the transmission line once assembled within the construction material such as depicted in first cross-section 210A. Accordingly, as depicted a pair of probe conductors 220A are disposed within the construction material 240 and are attached to a probe controller 230A within which is an electrical circuit 250A. As depicted each probe conductor 220A feeds through the probe controller 230A wherein a fitting maintains the probe controller 230A and probe conductor 220A in contact. Electrical contact is made from the electrical circuit 230A to the probe conductor 220 such that the electrical pulse can be applied and the reflected signal from the other end of the probe conductor 220 is detected and its timing information relative to the applied pulse is determined.

Within the configuration depicted in first cross-section 200C either the pair of conductors 220A form the entire probe are accordingly spaced apart by a distance comparable to that of the pair of conductors 210A of transmission line probe assembly 210, namely a few centimeters (an inch to two inches typically) or each conductor 220A forms part of a pair of conductors disposed perpendicular to the plane of the cross-section depicted and accordingly each of the conductors 220A represents one conductor with a transmission line probe and a pair of transmission line probes are depicted. Within other embodiments of the invention the transmission line probe may comprise three conductors.

Accordingly, as the velocity ($\upsilon$) of electrical signal propagated by the transmission lines is inversely dependent upon the effective dielectric constant of the probe, i.e. $\upsilon \propto 1/\kappa_A$, where $\kappa_A$ is the effective dielectric constant. Hence, the larger the time difference between the applied electrical pulse and the reflected signal from the other end of the probe the slower the velocity of the electrical signal. Accordingly, this time difference, $\Delta t \propto \kappa_A$. Based upon the effective dielectric constant the water content of the construction material, e.g. concrete, can be established through pre-determined calibration functions for that construction material.

As such the electrical circuit comprises several elements including a pulse generator to provide the desired pulse at the desired operating frequency, e.g. a fast rising step pulse generator, a timing circuit to determine the timing interval between the pulse and its reflection, a wireless interface to support communications to a PED or other device acquiring the data from the SMAK, a microprocessor, a battery, and a memory. The memory may store raw timing data versus time of acquisition, calibration data, converted effective water content etc.

Within first cross-section 200C the probe controller 230A is removed by undoing the fittings wherein the probes are left protruding from the surface of the construction material. Whilst this may be acceptable in some parts of a structure it is not acceptable in others as the protruding portions of the probes impact subsequent aspects of the structures build. Accordingly, in second cross-section 200D the probes 220B are designed to be contained within the construction material 240. As such the probes 220B now interface with electrical circuit 250B within the probe controller 230B via contacts 260 upon its lower surface such that the probe controller 230B is placed into position and the measurements performed. Optionally, the contacts 260 are spring loaded to accommodate variations in depth of the probes 220B.

Figure 2C:
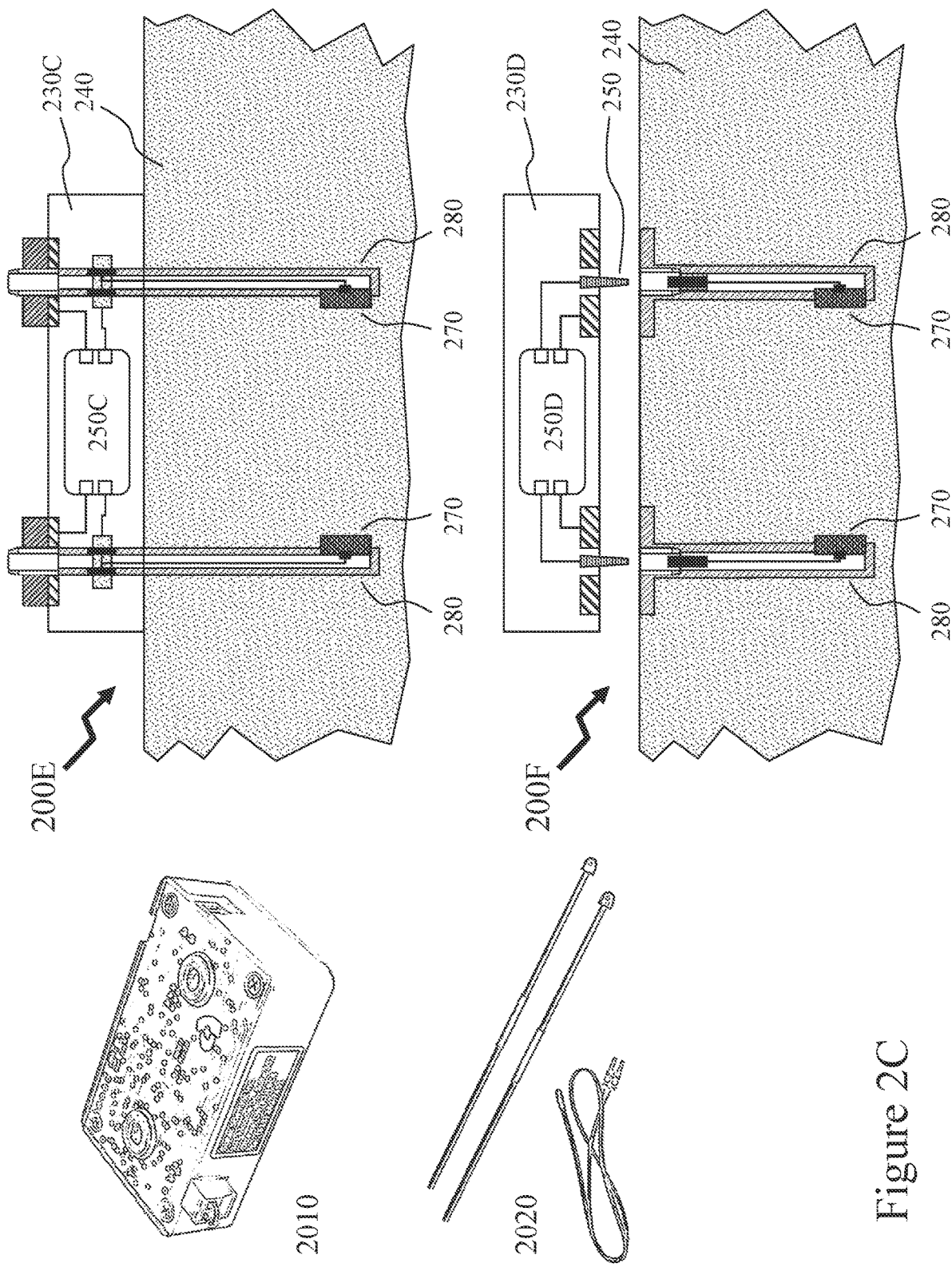

Within embodiments depicted in first and second cross-sections 200C and 200D the electrical measurement is a time domain reflectometry measurement. Alternatively, within FIG. 2C with third and fourth cross-sections 200E and 200F a variant probe configuration is depicted wherein rather than time domain measurements of an electrical signal propagating down a conductor embedded within the construction material the dielectric constant is derived from electromagnetic signals propagating directly through the construction medium. Accordingly, in third and fourth images 200E and 200F the basic premise of elements within the construction material being embedded with ends protruding or being fully embedded are maintained as are many of the other aspects. However, each probe now comprises a body 280 and an antenna element 270 such that within each pair of probes one radiates an electromagnetic signal and the other receives the signal. As the conductors to and from the antenna elements 270 are now independent of the dielectric constant of the construction material then the difference between pulses within the construction material to a reference timing in air is now dependent upon the dielectric constant of the construction material through which the signals propagate directly. First cross-section 200E in FIG. 2C depicts a similar mounting mechanism as that within first cross-section 200C in FIG. 2B whereas second cross-section 200F in FIG. 2C depicts a similar spring-mounted probe connection between the probe and module such as depicted and described in respect of second cross-section 200D in FIG. 2B. However, the probe body 280 now inserted within the material includes an additional ring at the surface which engages to a ring within the bottom of the module thereby providing a ground connection between the probe and module in addition to the electrical connections through the spring mounted probes.

Compact thin film/thick film antenna circuits being known in the art for providing antenna elements operating at different frequencies of interest within the range propagated through the medium. Similarly, compact microwave/RF resonators to provide the microwave signal and microwave switches to provide appropriate pulses. Accordingly, the control circuits 250C and 250D in the configurations depicted in third and fourth cross-sections 200E and 200F would in addition to the microwave/RF oscillator and switch provide the timing circuit to determine the timing interval for the propagation of the pulse, a wireless interface to support communications to a PED or other device acquiring the data from the SMAK, a microprocessor, a battery, and a memory. The memory may store raw timing data versus time of acquisition, calibration data, converted effective water content etc.

The control circuits 250A, 250B, 250C and 250D may accordingly comprise, for example, a microprocessor or controller, a pulse generator for generating the electrical pulse/signal, a microwave/RF switch, a pulse detection circuit for detecting the returned electrical pulse/signal, and a timing circuit to determine the timing between the generation of the electrical pulse/signal and receipt of the returned electrical pulse/signal.

Figure 3A:
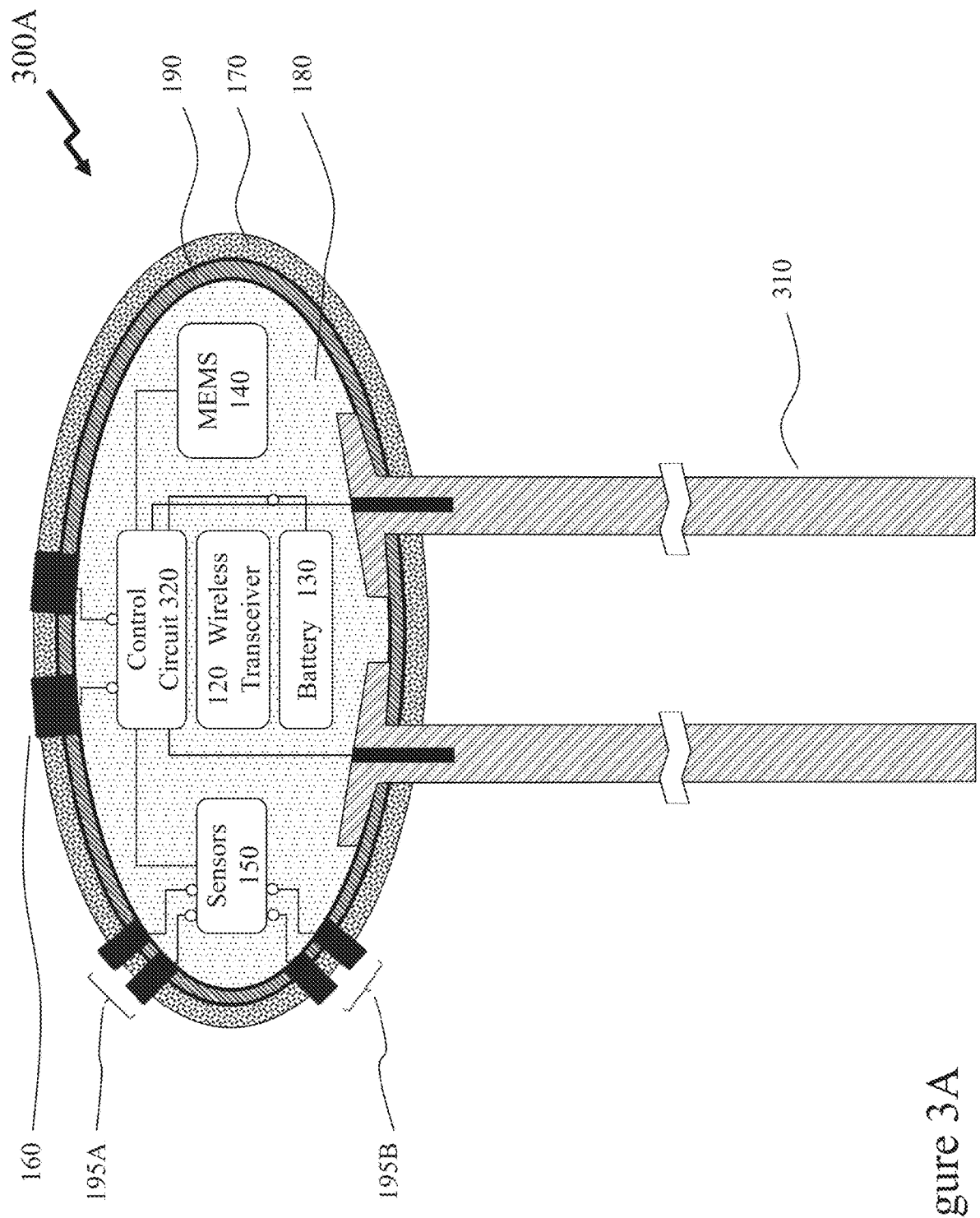
FIGS. 3A and 3B depict exemplary embedded sensor concepts according to embodiments of the invention for providing time domain to establish water content within concrete.

Now referring to FIG. 3A there is depicted a SMAK incorporating a time domain reflectometry-based water content sensor. As such SMAK 300A comprises contacts 160 formed within an outer shell 170 defining an interior within which is an intermediate casing 190 wherein the interior is filled within filler 180. Disposed within the SMAK 300A are control circuit 320, wireless transceiver 120, battery 130, MEMS 140, and sensors 150 which are coupled to first and second SENsor INTerfaces (SENINTs) 195A and 195B. The control circuit 320 coupled to the probes 310 comprises, typically, in addition to the pulse generator and timing circuit for the time domain reflectometry measurement, a microprocessor and a memory. Accordingly, pulses applied to the probe(s) 310 lead to a measurement of the effective dielectric constant and through calibration data the water content of the construction material the SMAK 300A is embedded within. Whilst SMAK 300 depicts a pair of probes 310 it would be evident that within other embodiments of the invention the SMAK may have a single probe or multiple probes.

Figure 3B:
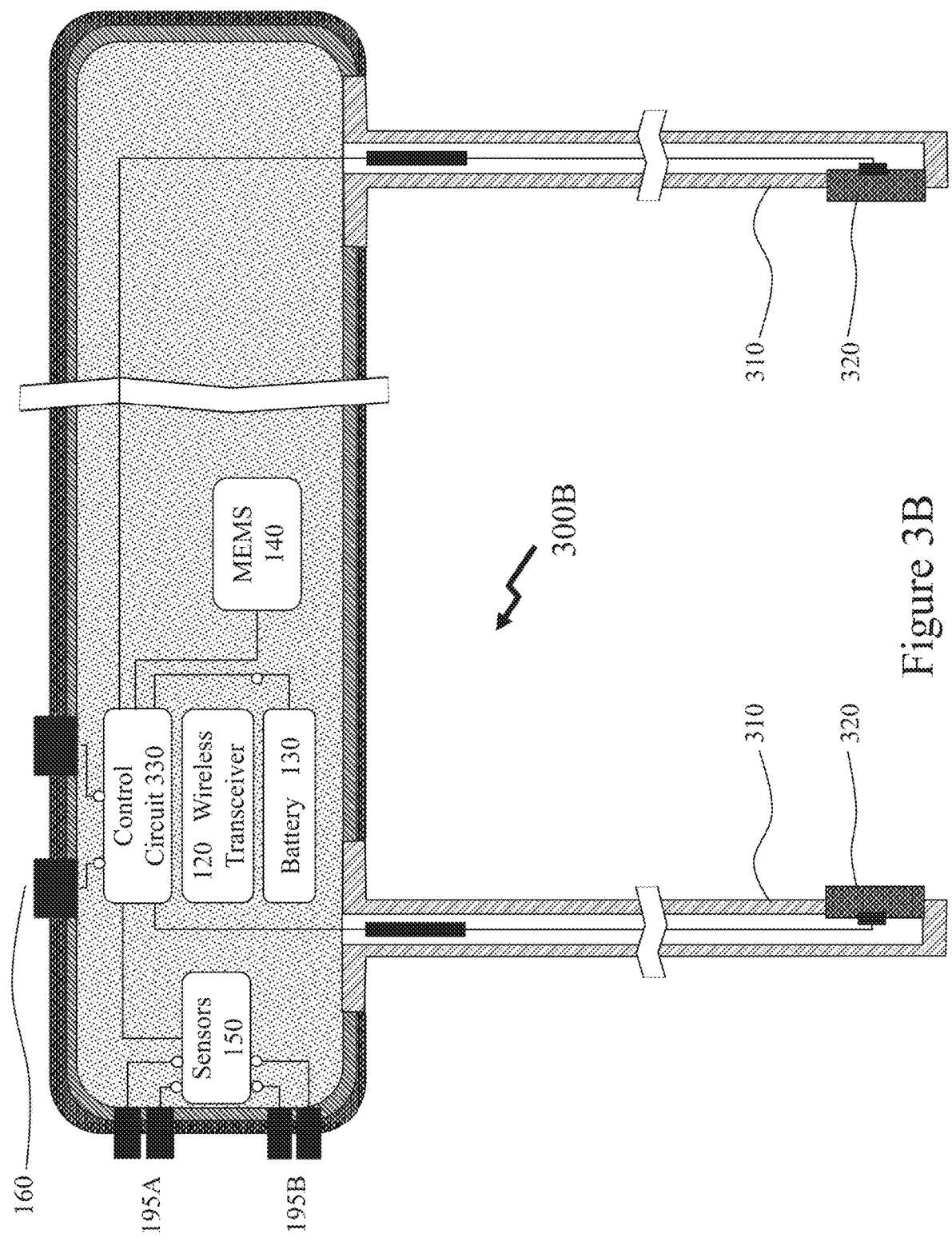

Referring to FIG. 3B there is depicted a SMAK incorporating a pulse based water content sensor comprising probes 310 and antenna elements 320. As such SMAK 300B comprises contacts 160 formed within an outer shell 170 defining an interior within which is an intermediate casing 190 wherein the interior is filled within filler 180. Disposed within the SMAK 300A are control circuit 320, wireless transceiver 120, battery 130, MEMS 140, and sensors 150 which are coupled to first and second SENsor INTerfaces (SENINTs) 195A and 195B. The control circuit 320 coupled to the probes 310 comprises, typically, in addition to the microwave/RF generator and timing circuit for the pulse based measurements, a microprocessor and a memory. Accordingly, pulses applied to one of the probes 310 and therein its antenna 320 are transmitted and coupled to the other antenna 320. Accordingly, the resulting time domain measurement yields the effective dielectric constant of the construction material and through calibration data the water content of the construction material the SMAK 300B is embedded within is established.

The control circuits 320 and 330 may comprise, for example, a microprocessor or controller, a pulse generator for generating the electrical pulse/signal, a microwave/RF switch, a pulse detection circuit for detecting the returned electrical pulse/signal, and a timing circuit to determine the timing between the generation of the electrical pulse/signal and receipt of the returned electrical pulse/signal.

Solution Characteristics and Water to Cement Ratio Using Embedded Porous Materials.

Figure 4A:
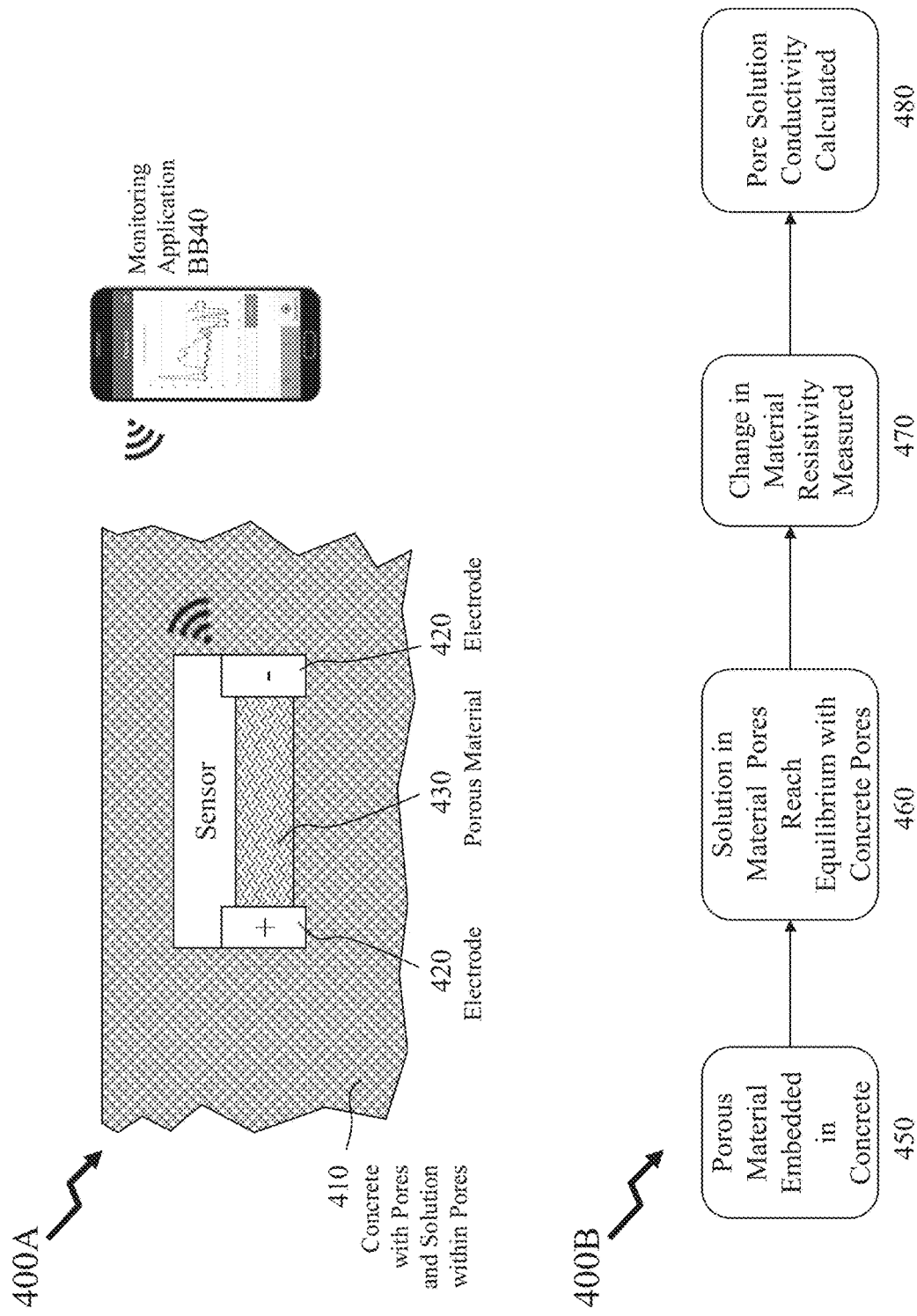
FIG. 4A depicts exemplary schematic for establishing pore solution conductivity via embedded sensors with porous elements according to embodiments of the invention.

Some construction materials such as concrete are porous materials and as a result either initially by being in liquid or slurry form, retaining water when cured or subsequently absorbing moisture the conductivity of the solution available in such pores is of interest in defining specific aspects of the construction material in different deployment applications of the construction material. Accordingly referring to FIG. 4A there is depicted an embedded sensor methodology in first image 400A according to an embodiment of the invention wherein a porous material 430 establishes equilibrium with any solution within the construction material 410, e.g. concrete. The conductivity of the porous material is measured via electrodes 420 disposed at either end of the porous material 430. The embedded sensor communicates to a monitoring application 440 upon a scanning device via a wireless interface. Accordingly, second image 400B depicts the conceptual flow wherein a porous material is embedded within concrete in first step 450 wherein subsequently the solution within the concrete pores reach equilibrium with the porous material in step 460. Accordingly, the sensor allows in step 470 for measurement of changes in the porous material resistivity and therein the pore solution conductivity can be calculated in step 480.

Embedded pH Sensor: The determination of concrete pH is of importance to the concrete industry since it provides an indication of the state of the steel reinforcement with respect to corrosion. Changes of in-situ pH can also be used to determine the rate at which other concrete degradation mechanisms are occurring. pH is a measurement of the concentration of hydrogen ions in a certain solution/medium. This can be determined through measuring the electrode potential of a pH electrode such as an ion-selective electrode made of a doped glass membrane that is sensitive to hydrogen (or other specific ions), a solid-state pH electrode, or an Ion Sensitive Field Effect Transistor (ISFET) for example. Such pH sensors may form part of one or more SMAK configurations according to embodiments of the invention.

Conductivity Measurement from pH: As concrete is a porous material, the conductivity of solution available in pores within the concrete is of interest in specific applications. Since pH is a measure of the concentration of hydrogen ions in the solution, such a measurement can be employed to determine the concentration of hydroxyl ions or alkali concentration in solution. The alkali concentration can therefore indicate the resistivity of the pore solution which is beneficial for determining several properties of the concrete. For instance, if the conductivity of the pore solution is determined along with the overall conductivity of concrete one or more parameters relating to the concrete, including what is known as the Formation Factor, can be calculated which provide information regarding the total porosity, tortuosity and pore connectivity of the concrete.

Water/Cement Content from Overall Concrete Resistivity and Pore Solution Resistivity: The electrical conductivity of water is orders of magnitude higher than that of other components of plastic concrete, i.e. concrete that has not yet set, such as aggregates or cement particles. Therefore, a measurement of the electrical resistivity of concrete can determine, indirectly, the amount of water in a specific volume of concrete. However, the conductivity of mixing water changes throughout mixing due to an ongoing chemical interaction with cement and chemical admixtures. Therefore, a measurement of the conductivity of the water is an important element, in addition to the conductivity of the whole concrete mixture, in the process of determining the water-to-cementitious-materials (W/CM) ratio. Accordingly, a SMAK capable of determining the resistivity of the overall concrete as well as the conductivity of the pore solution (determined either indirectly, through measuring the medium's pH, or directly, through the changes of conductivity of an embedded porous material) can establish the W/CM ratio of the concrete it is embedded within. Accordingly, the W/CM ratio may be established in-situ during casting with one or more SMAKs comprising sensors for pH and electrical resistivity or alternatively during transportation using one or more SMAKs or one or more dual sensor-based devices either mounted to a concrete truck or forming part of a mixer drum, a mixer blade upon the inner surface of the mixer drum or a mixer blade within the mixer drum.

Figure 4B:
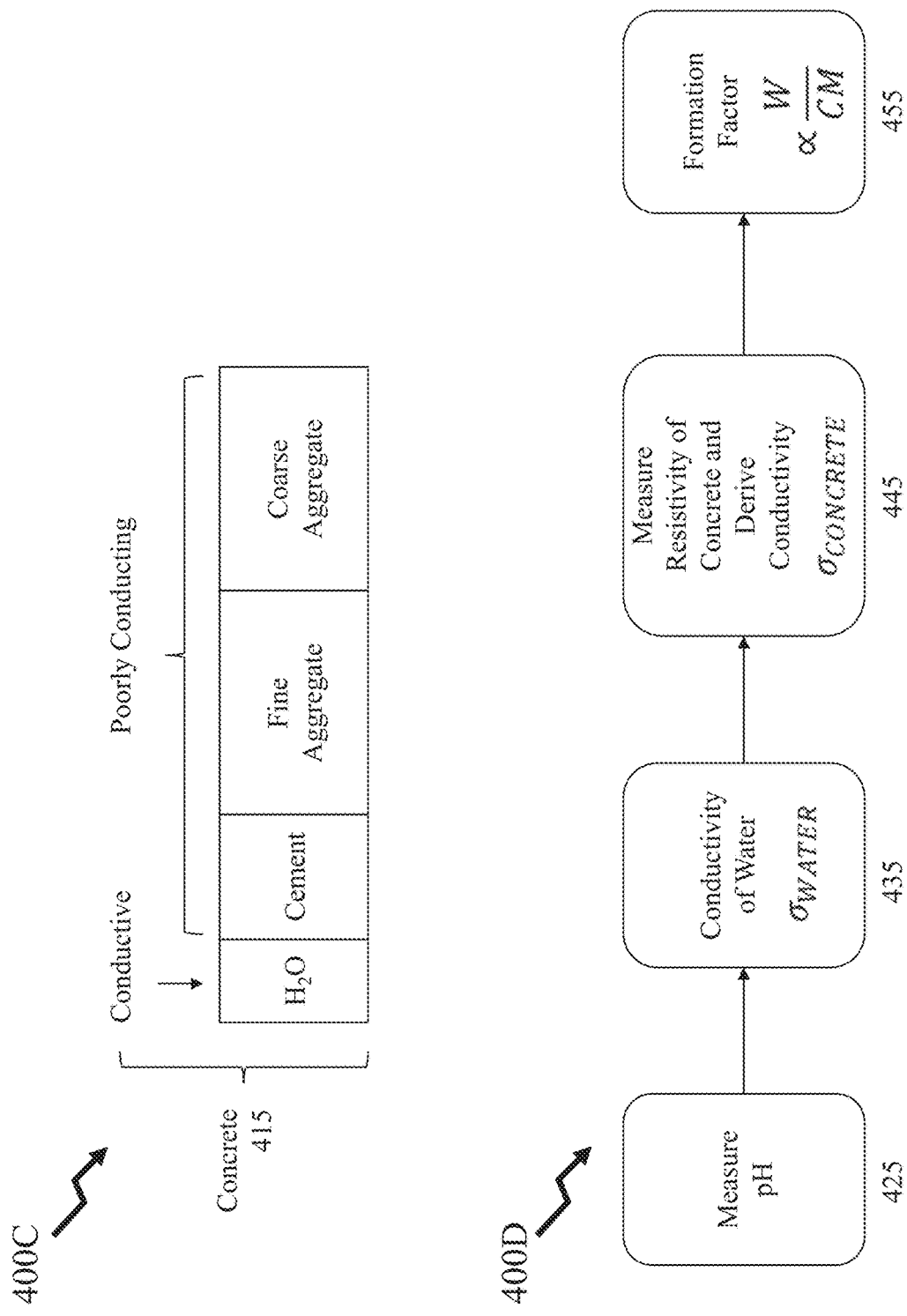
FIG. 4B depicts exemplary schematics for establishing water to cement ratio using embedded sensors according to embodiments of the invention.

Accordingly, as depicted within FIG. 4B within first image 400C concrete comprises several components wherein the cement, fine aggregate and coarse aggregate are poorly conductive whilst the water portion is highly conductive. Accordingly, in second image 400D an exemplary process is depicted wherein in first step 425 the pH of the concrete is measured. Subsequently the conductivity of water, $\sigma_{WATER}$, is measured in step 435 followed by the determination of the resistivity of concrete and therein the conductivity of the concrete, $\sigma_{CONCRETE}$ in step 445. Accordingly, the formation factor, which is proportional to the water to cement ratio, W/CM can be established in step 455.

Figure 4C:
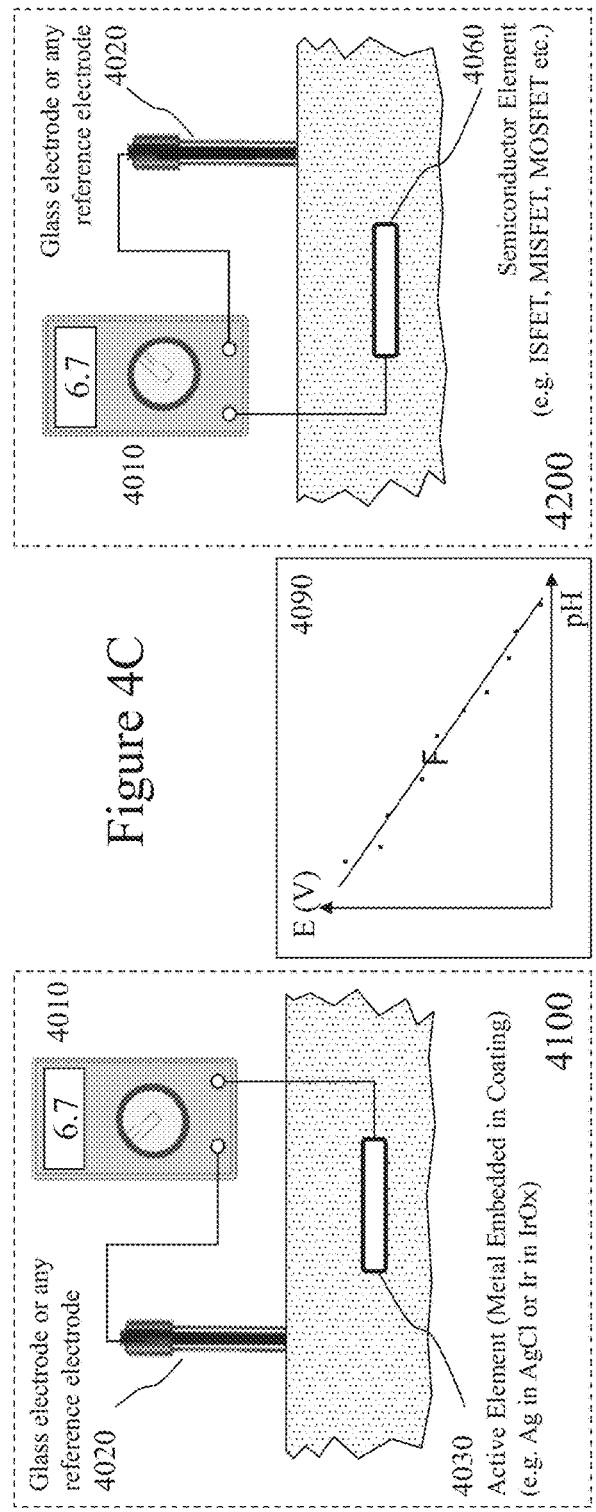
FIG. 4C depicts exemplary embedded and partially embedded sensor configurations for establishing pH according to embodiments of the invention.
Figure 4C:
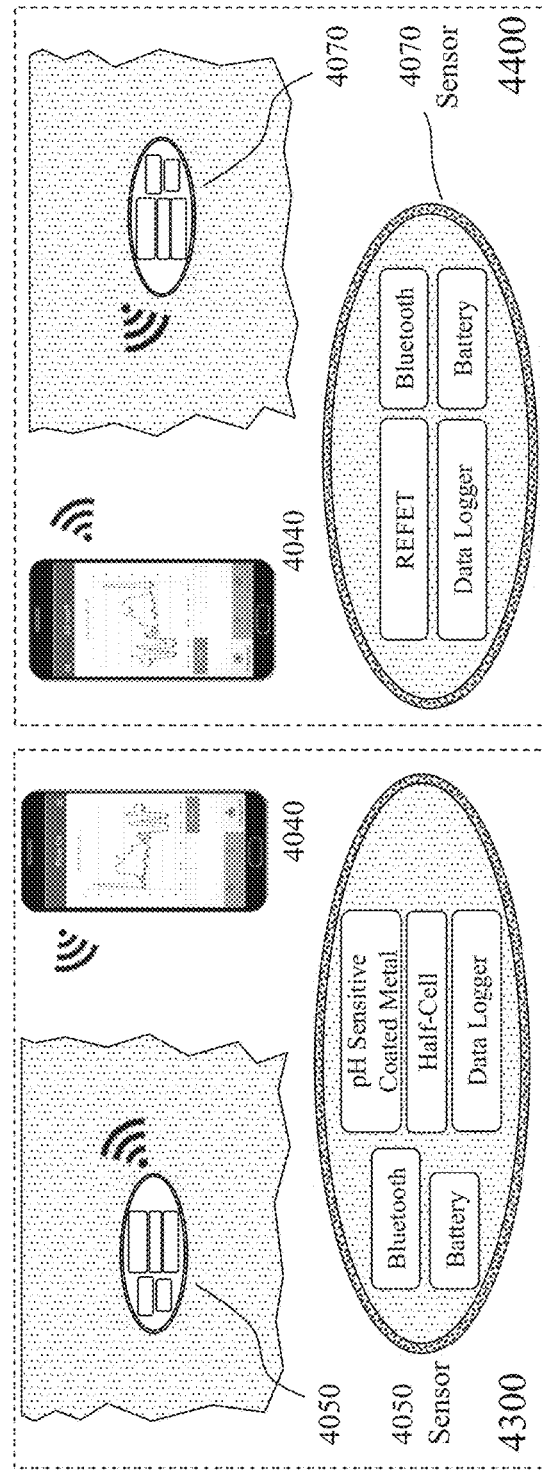

Referring to FIG. 4C there are exemplary embedded and partially embedded sensor configurations for establishing pH according to embodiments of the invention within first to fourth images 4100 to 4400 respectively. Within first image 4100 a partially embedded sensor configuration is depicted wherein a measurement device 4010 is connected to a reference electrode 4020, e.g. a glass electrode as known in the art, connected to the surface of the concrete directly or via a conductive pad (not depicted). The device 4010 is also connected to an active element 4030 embedded within the concrete such as a metal element embedded within a coating such as Ag in AgCl or Ir in IrOx. Within second image 4200 the device 4010 and reference electrode 4020 are the same but the active element is now a semiconductor element 4060 such as an ISFET, MISFET, MOSFET etc.

Within third image 4300 an embedded sensor 4050 exploiting the concept depicted in first image 40100 is depicted which performs the measurements of measurement device 4010, reference electrode 4020, and active element 4030 but within a self-contained sensor, the embedded sensor 4050. As depicted the embedded sensor 4050 contains a data logger, a half-cell for the reference electrode, a pH sensitive coated metal, a battery, and a Bluetooth transceiver which allows data to be transferred from the embedded sensor 4050 to a device 4040. Other elements, not depicted in third image 40300, may form part of the embedded sensor 4050.

Within fourth image 4400 an embedded sensor 4070 exploiting the concept depicted in second image 40200 is depicted which performs the measurements of measurement device 4010, reference electrode 4020, and semiconductor element 4060 but within a self-contained sensor, the embedded sensor 4070. As depicted the embedded sensor 4070 comprises a REFET, datalogger, battery and a Bluetooth transceiver which allows data to be transferred from the embedded sensor 4070 to a device 4040. Other elements, not depicted in fourth image 40400, may form part of the embedded sensor 4050.

Figure 5A:
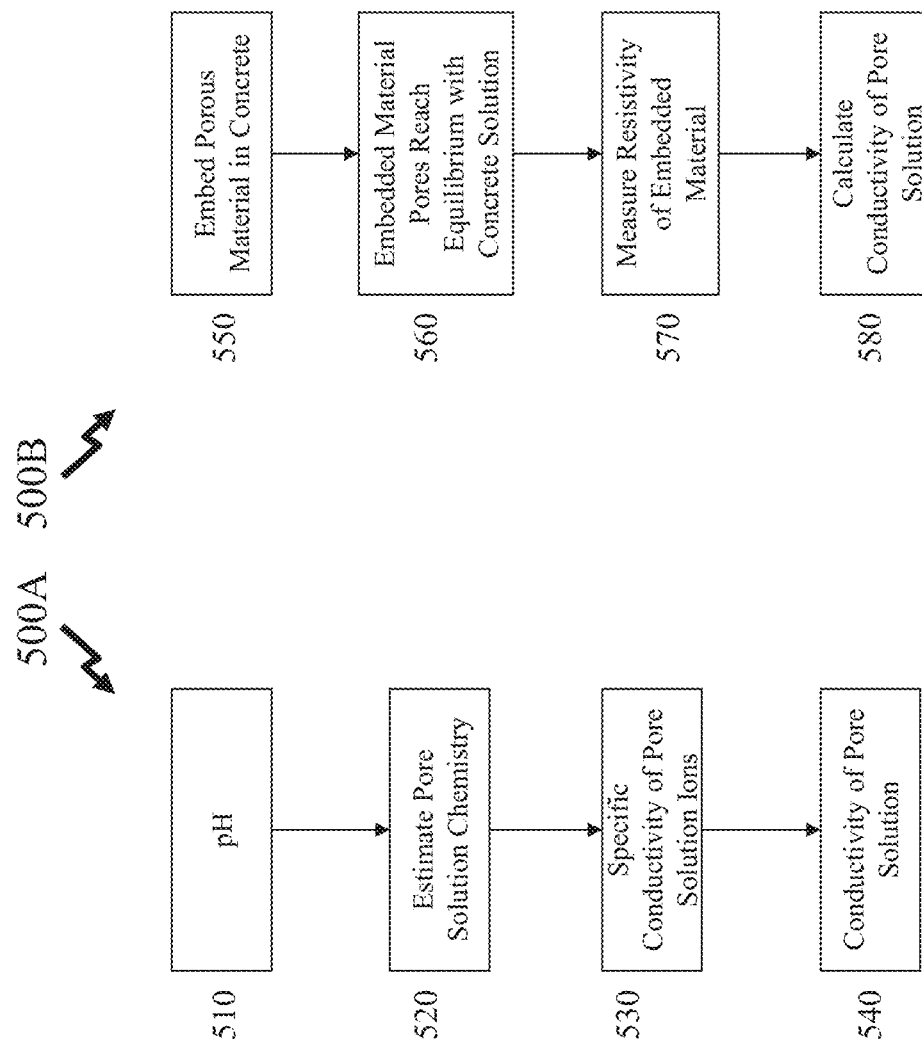
FIG. 5A depicts process flows for establishing pore solution conductivity via embedded porous elements forming part of the sensors in contrast to a pH-based methodology according to embodiments of the invention.

Pore Solution Conductivity from Embedded Porous Material: Referring to FIG. 5A there are depicted first and second exemplary process flows 500A and 500B respectively for determining the conductivity of this solution exploiting embodiments of the invention through either pH measurements or embedding a porous material forming part of a sensor within the construction material. These first and second exemplary process flows 500A and 500B respectively may employ SMAKs according to embodiments of the invention. Considering the pH based route then this is depicted in first process flow 500A comprising first to fourth steps 510 to 540 respectively, these being:

First step 510 wherein the SMAK acquires a pH measurement using a pH sensor such as an ISFET for example;

Second step 520 wherein the pore solution chemistry is estimated for the construction material either generally or in dependence upon the pH measured;

Third step 530 wherein for the pore solution chemistry established; and

Fourth step 540 wherein the pore solution conductivity is established.

It would be evident that steps 520 and 530 may have been performed previously and that step 510 therefore in the measurement of the pH leads to establishing the pore solution conductivity in step 540 from a lookup table, application of one or more algorithms previously established etc. As with the consideration of maturity curves etc. discussed above such lookup table(s), algorithms etc. may be stored within the SMAK allowing direct establishment of the pore solution conductivity by the SMAK which is communicated to any scanning device and therein to the cloud-based storage etc. or the raw pH value is acquired by the scanning device and the calculations performed upon it or remotely within the cloud-based application(s) associated with the acquisition, processing, and storage of data relating to SMAKs within construction materials. Alternatively, as described the pore solution chemistry and pore solution ion conductivities are established real time either generally or specifically in dependence upon the pH.

Referring to second process flow 500B a methodology based upon measuring the conductivity of the solution within the construction material is presented comprising first to fourth steps 550 to 580 respectively. These comprising:

First step 550 wherein the SMAK is embedded within the construction material, e.g. concrete, as described in respect of SMAKs previously but the SMAK now includes a porous material in direct contact with the construction material;

Second step 560 wherein the embedded porous material reaches equilibrium with the pores within the construction material;

Third step 570 wherein for the resistivity of pore solution is measured; and Fourth step 580 wherein the pore solution conductivity is determined in dependence upon the resistivity.

Accordingly, if the pore solution changes then the equilibrium state with the embedded porous material will subsequently adjust such that the ongoing resistivity allows for ongoing determination in respect of changes in the pore solution of the construction material.

Figure 5B:
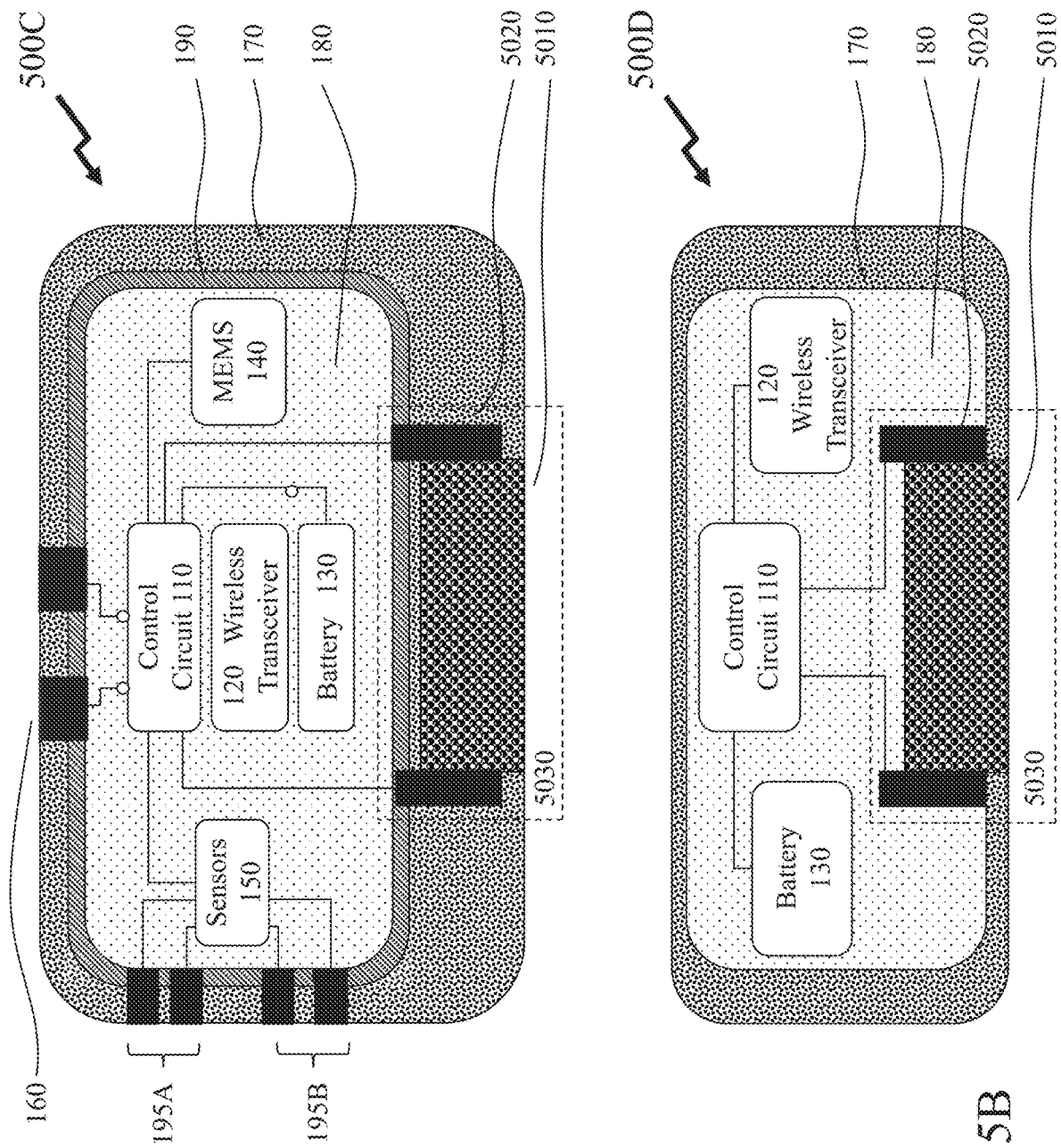
FIGS. 5B and 5C depict exemplary embedded sensor concepts for establishing pore solution conductivity via embedded porous elements forming part of the sensors according to embodiments of the invention.

Referring to FIG. 5B there are depicted exemplary first and second SMAK designs 500C and 500D according to embodiments of the invention. In first SMAK design 500C the SMAK comprises the control circuit 110, wireless transceiver 120, battery 130, MEMS 140, and sensors 150 which are coupled to first and second SENsor INTerfaces (SENINTs) 195A and 195B. The control circuit 110 is also coupled to contacts 160 and a resistivity sensor 530 comprising a porous material 5010 and resistivity contacts 5020. The porous material 510 is exposed to the external environment such that when embedded within the construction material the porous material 5010 can reach equilibrium with the solution portion of the construction material. Accordingly, the control circuit 110 can establish resistivity measurements for the resistivity sensor 5030. As depicted the SMAK comprises an intermediate casing 190 which encapsulates the sensor filler 180, e.g. a foam, air, etc. and is surrounded by an outer shell 170. As depicted the porous material 5010 is entirely external to the intermediate casing 190 and only resistivity contacts 5020 extend through it for the resistivity sensor 5030 although other contacts 160 and first and second SENINTs 195A and 195B also do.

In second SMAK design 500D the SMAK is reduced in complexity to the control circuit 110, wireless transceiver 120, and battery 130 together with the resistivity sensor 5030 comprising porous material 5010 and resistivity contacts 5020. In this embodiment the porous material 510 is not outside an intermediate casing and is depicted as being within both the outer shell 170 and filler 180 although it would be evident that according to the filler 180 that the outer shell 170 may be omitted.

Optionally, a SMAK comprising a porous sensor 5030 may be stored such that the porous material is sealed prior to use such as by the use of a peel-off cover or sealing the SMAK within a bag discretely or in combination with a material such as a desiccant or solution of predetermined and known composition. Optionally, a solution may be added to the porous material 5010 prior to deployment, e.g. deionized water.

The control circuit 110 within first and second SMAK designs 500A and 500B may, for example, comprise a microprocessor or controller, a pulse generator for generating the electrical pulse/signal, a microwave/RF switch, a pulse detection circuit for detecting the returned electrical pulse/signal, and a timing circuit to determine the timing between the generation of the electrical pulse/signal and receipt of the returned electrical pulse/signal.

Moisture Content and Water to Cement Ratio from Time Domain Measurements

As described and discussed above with respect to embodiments of the invention in FIGS. 2A to 3B respectively the dielectric constant of a construction material such as concrete is dependent upon its water content as water has a dielectric constant of 81 versus approximately 2-4 for dry concrete. Accordingly, the dielectric constant of concrete, other cementitious materials and other construction materials will vary from initial manufacture through to its final cured state as the water content changes. It would be evident therefore that a measurement of the dielectric constant of the construction material, such as concrete, can be employed in order to establish the water content of the construction material. For cementitious materials such as concrete the resulting water content can be employed to determine the water to cement ratio of the construction material. Accordingly, time domain measurements exploiting either transmission line probe assemblies such as depicted in FIGS. 2A and 2B, embedded time domain assemblies such as depicted in FIG. 2C, or SMAK based embedded time domain reflectometry (TDR) devices such as depicted in FIGS. 3A and 3B respectively can be employed to determine the dielectric constant of the construction material they are embedded within and therein the water content or other parameters dependent upon the dielectric constant.

However, the measurements exploit microwave/RF signal propagation within the construction material can result in factors related to the frequency at which these measurements are performed. For example, there is a difference between measurements performed below approximately 10 GHz versus those performed above this frequency. This arises as the loss factor of the construction material can be significantly impacted by an increase in pore solution conductivity arising from ions such as chloride, for example, within the pore solution. Whilst the ionic content of the pores does not significantly affect dielectric constant, although there is some dependence, the loss factor which causes attenuation can be changed due to the increase in ohmic conductivity.

Accordingly, considering cement mortar, both conductivity and dielectric constant increase with increasing amounts of chloride and sodium ions. This effect can also change with the water/cement (w/c) ratio as the impact on pore structure from chloride ions, within materials such as Portland cement based mortar, varies with w/c ratio. Accordingly, additional data relating to the moisture content and pores of the concrete can also be determined from the loss derived from microwave/RF based measurements either using time domain pulse techniques or time domain reflectometry based techniques.

Figure 5C:
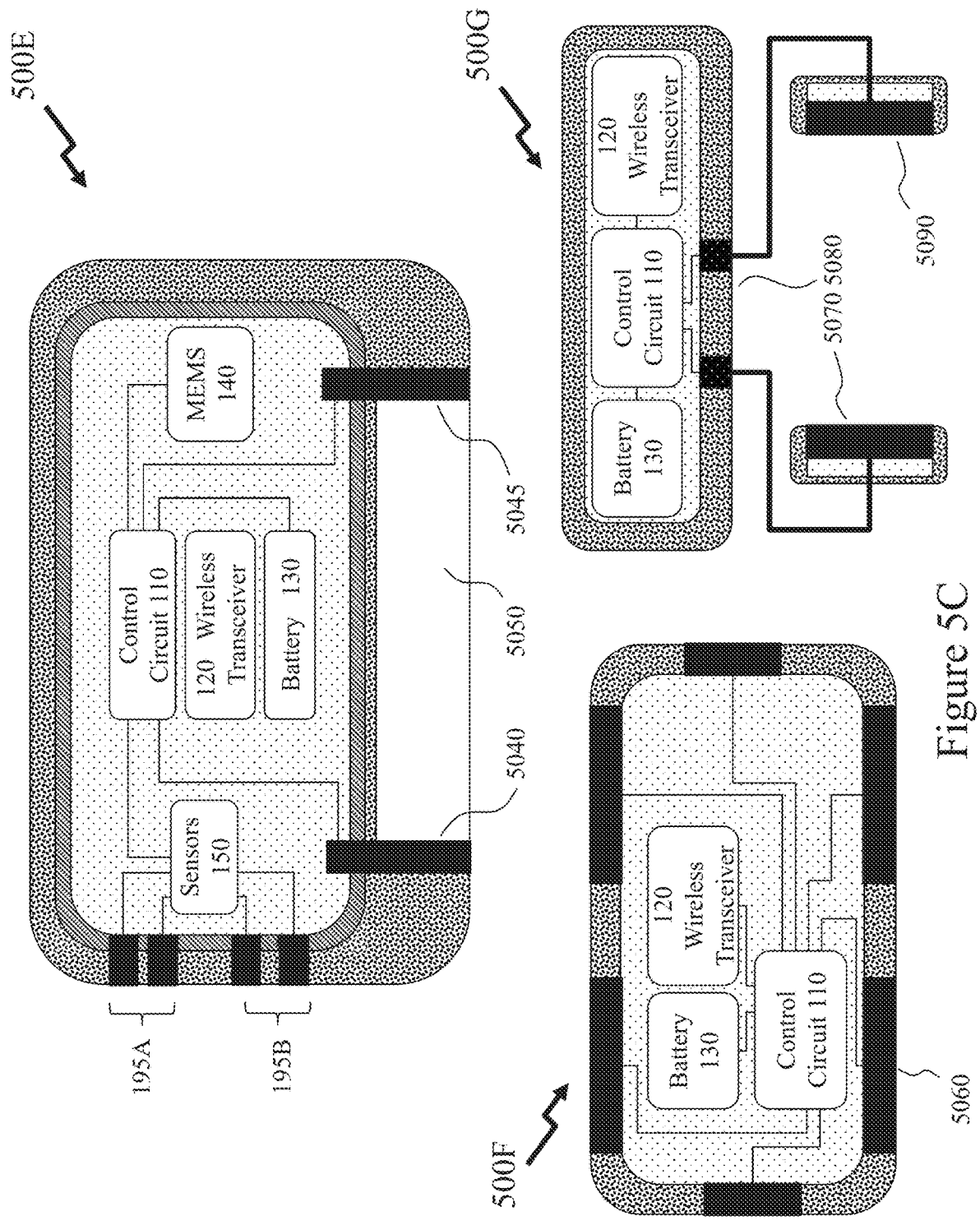
Figure 6B:
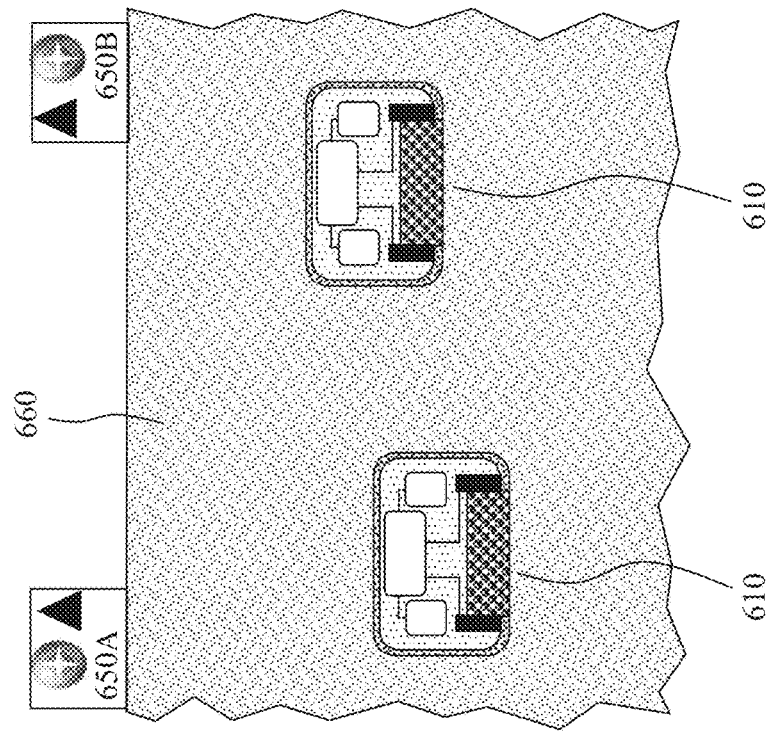
FIGS. 6A and 6B depict exemplary systems for the triangulation of embedded sensors according to an embodiment of the invention.
Figure 6A:
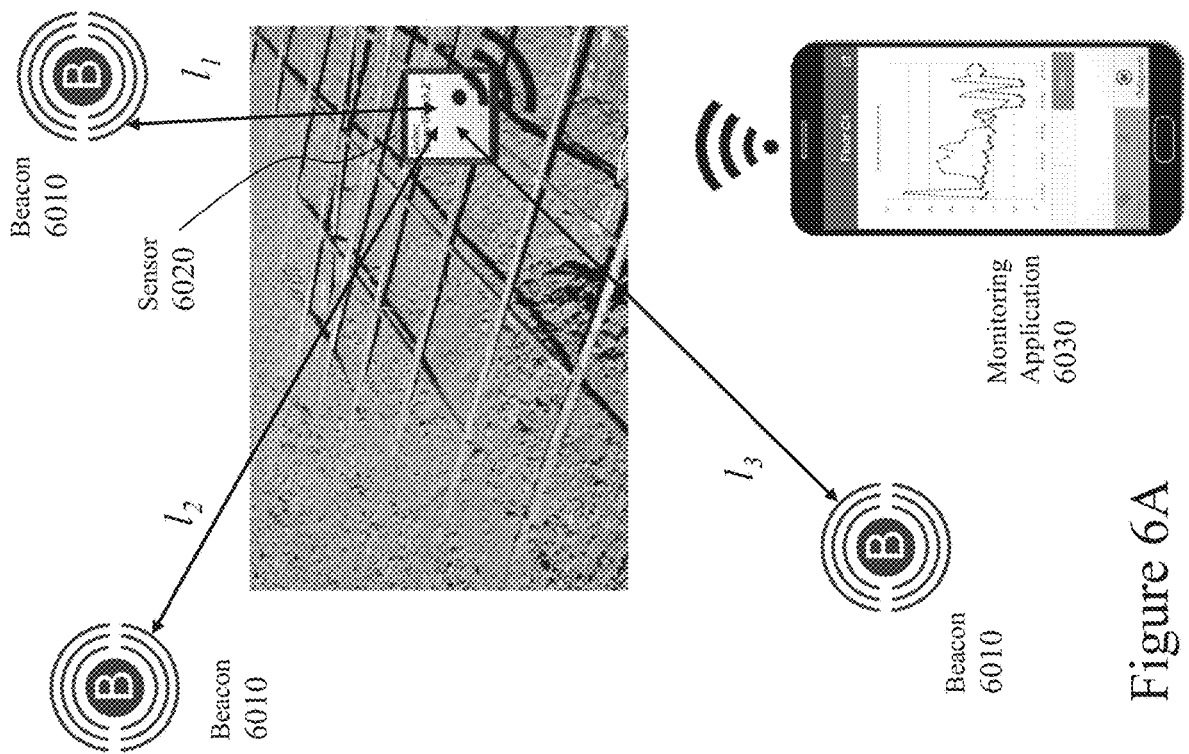

Referring to FIG. 5C there are depicted exemplary third to fifth SMAK designs 500E to 500G respectively according to embodiments of the invention. In third SMAK design 500E the SMAK comprises the control circuit 110, wireless transceiver 120, battery 130, MEMS 140, and sensors 150 which are coupled to first and second SENsor INTerfaces (SENINTs) 195A and 195B. The control circuit 110 is also coupled to microwave emitter 5040 and microwave receiver 5045 which are disposed at opposite ends of a cavity 5050 formed in the external surface of the third SMAK design 500E. Accordingly, when the third SMAK design 500E is embedded into a material the material fills the cavity 5050 such that microwave/RF signals emitted by the microwave emitter 5040 are coupled to the microwave receiver 5045 through the material filling the cavity. Accordingly, variations in the microwave properties of the material filling the cavity 5050 result in variations in the transmission delay and/or attenuation in the microwave/RF signals received by the microwave receiver 5045. Accordingly, these variations can be converted by the control circuit 110 directly or by a remote device to which the data is transmitted via the wireless transceiver 120.

Now referring to fourth SMAK design 500F there is depicted a SMAK according to an embodiment of the invention comprising a battery 130, wireless transceiver 120, and control circuit 110 which is connected to the battery 130 and wireless transceiver 120 together with multiple microwave transducers 5060. Within an embodiment of the invention each microwave transducer 5060 may comprise a microwave transmitter and a microwave receiver wherein each fourth SMAK design 500F may be established through the control circuit to transmit microwave/RF signals in a first mode and receive microwave/RF signals in a second mode. Accordingly, a fourth SMAK design 500F may alternate between these modes according to a predetermined schedule stored within a memory such that the fourth SMAK design 500F alternately transmits and receives. With a second SMAK within the material to the same fourth SMAK design 500F operating according to a second predetermined schedule may be receiving whilst another SMAK is transmitting and transmitting when the other SMAK is receiving. Optionally, within other embodiments of the invention a subset of the microwave transducers 5060 may be microwave transmitters whilst another subset of the microwave transducers 5060 may be microwave receivers.

Accordingly, multiple SMAKs according to the fourth design 500F are disposed within a material then these may upon initial deployment establish initial microwave/signal properties such as received signal level amplitudes and timing of signals etc. transmitted by a subset of the SMAKs to the other SMAKs. Subsequently, variations of properties derived from subsequently transmitted/received microwave/RF signals can be employed to establish variations within the material within which the SMAKs are deployed. Accordingly, in contrast to the third SMAK design 500E the distance between microwave transmitter and microwave receiver is not limited to the dimensions of the third SMAK design 500E but rather the distance between the SMAKs within the material.

Accordingly, each SMAK may transmit a different microwave/RF signal, for example, upon a different frequency or encoded differently such that a SMAK receiving multiple microwave/RF signals can determine which SMAK they were transmitted by and thereby differentiate between signals from other SMAKs.

Alternatively, fifth SMAK design 500G employs a first device 5080 comprising a control circuit 110 which is coupled to a battery 130 and wireless transceiver 120. The first device 580 is coupled to a first microwave module 5070 and a second microwave module 5090. For example, the first microwave module 5070 may be a transmitter and the second microwave module 5090 a receiver. Alternatively, the first microwave module 5070 and second microwave module 5090 may each comprise a microwave transceiver. Accordingly, microwave measurements may be established in dependence upon the microwave signals transmitted from a microwave module, such as the first microwave module 5070, to another microwave module, such as the second microwave module 5090 or vice-versa. In contrast to third SMAK design 500E the distance between microwave transmitter and microwave receiver is not limited to the dimensions of the third SMAK design 500E but rather the distance between the first microwave module 570 and second microwave module 5090 within the material. Accordingly, this separation is determined by the positioning of the first microwave module 5070 and second microwave module 5090 and/or the lengths of the cables connecting the first microwave module 5070 and second microwave module 5090 to the first device 5080.

The control circuit 110 within third and fourth SMAK designs 500C and 500D may, for example, comprise, a microprocessor or controller, a microwave/RF signal generator for generating microwave/RF signals, a microwave/RF switch, a microwave/RF receiver circuit for detecting and/or measuring the received microwave/RF signals, and a timing circuit to determine timing transmitted and received microwave/RF signals.

Embedded Air Content

The speed of sound in a medium, such as a solid, is affected by the density, compressibility and shear modulus of the medium. Where the medium is a construction material such as concrete in the plastic state then this can be viewed as a two-phase mixture, or an aerated liquid. The speed of propagation of sound in such a case is highly affected by the volume fraction of air since this parameter affects the density and compressibility of the mixture. If the wavelength of the acoustic waves is larger than the size of the air bubbles within the medium, then the air volume fraction can be found directly from the speed of propagation of sound in such a mixture. Accordingly, embodiments of the invention exploit an acoustic source (transmitter) and an acoustic receiver separated by a known distance as well as a signal processor to determine the speed of propagation of the acoustic signal. Accordingly, as described and depicted in respect of FIGS. 6B to 8 SMAKs and test systems supporting acoustic transmitters and receivers are presented.

Accordingly, the knowledge of the location of the acoustic transmitter and acoustic receiver is required in order to define the separation between them and hence allow derivation of the velocity from the timing established in respect of the acoustic signals sent and received. Where the SMAK is physically attached to an element of the infrastructure prior to the application of the construction material, e.g. being attached to a rebar then the physical location of the SMAK may be defined through traditional surveying means etc. or exploit a concept which provides for an automatic establishment of the location of a device based upon exploiting a plurality of beacons. Such a methodology being depicted in FIG. 6A wherein a system configuration for automatic location mapping of electrical measurements according to an embodiment of the invention wherein a sensing device such as electrical test equipment (not depicted) or a sensor 6020 for example receives signals from a plurality of beacons 6010. As depicted the sensor 6020 is in wireless communication with a PED executing a monitoring application 6030 to extract data from the sensor 6020. In addition to the electrical measurements etc. performed by the sensor 6020 and data relating to the sensor 6020 itself the raw location data and/or processed location data with respect to the plurality of beacons 6010 may be transferred. In this manner the extracted data is geotagged to a specific location as well as a specific sensor. A variety of signaling and/or location techniques may be employed to establish the relative location of the sensor 6020 relative to the plurality of beacons 6010. One or more of the beacons 6020 may further incorporate a method to establish its location such as accessing global navigation satellite system (GNSS) signals or wireless triangulation to wireless base stations etc. which themselves establish their location via GNSS signals etc.

This technique may be extended to include automatic location of embedded SMAKs where their location is initially unknown, such as being pre-deployed within a delivery of concrete that is then poured at the work site. Accordingly, this methodology can be employed as depicted in first image 600 of FIG. 6B wherein a pair of SMAKs 610 are depicted embedded within a construction material 660. Also depicted are first and second beacons 650A and 650B which contain a GPS receiver together with an ultrasonic transmitter and/or radio frequency (RF) transmitter together with a wireless interface, not shown for clarity. An ultrasonic receiver within a SMAK 610 receives the ultrasonic signals from the ultrasonic transmitters allowing it to determine its distance from each of the first and second beacons 650A and 650B respectively. Alternatively, RF signals may be employed.

Optionally, the ultrasonic signals may include data relating to the GPS location of the respective beacon of the first and second beacons 650A and 650B respectively allowing the SMAKs to establish their location such that this is then included within subsequent readings of SMAK data by a scanning device. Alternatively, the SMAKs may transmit ultrasonic signals which are then received by the first and second beacons 650A and 650B and processed by a PED, for example, in wireless communication with the first and second beacons 650A and 650B such that the PED processes all the data and determines the sensor location which is then stored in the remote storage. Optionally, the PED may be a scanning device and transmits the established location to the SMAK.

The addition of ultrasonic ranging, or another ranging technique, to augment the GPS location arises as the standard quoted accuracy of a low cost GPS receiver is approximately 15 meters (49 feet) and that even for high quality receivers according to the GPS Standard Positioning Service (SPS) it is currently approximately 3 meters (10 feet) (http://www.gps.gov/systems/gps/performance/accuracy/). However, with ultrasonic ranging the accuracy of location setting achieved by the inventors is less than 10 cm representing approximately two orders of magnitude improvement over GPS and other local positioning systems (LPS) based upon wireless signal triangulation, radio broadcast tower triangulation, and imaging with accuracies of the order of a meter. It would be evident that in operation typically employ 3 beacons would be employed to remove ambiguities over position whilst they are described as having 2 beacons. Optionally, ultrasonic range determination may be replaced by other techniques including, but not limited to, visible optical, infrared optical, visible or infrared laser based optical, microwave, and radio frequency distance measurements. Optionally, the beacon range determination may be one method when the SMAK is initially deployed without the construction material and another once covered by the construction material. Optionally, other variants may include performing the distance determination within the beacons, obtaining GPS location from a GPS receiver within the SMAK prior to deployment where it is affixed to the structure being characterised once the construction material is applied.

Optionally, the GPS location, which may be considered a reference in some circumstances from which the secondary locations of the measurements points are determined may be replaced by another method of establishing a reference on the structure, including but not limited to architectural structures, foundations, brick/block walls, pavements, bridges/overpasses, and motorways/roads. Alternative methods may include, local positioning systems (LPSs) employing wireless techniques in conjunction with cellular base stations, Wi-Fi access points, and radio broadcast towers for example, establishing a predetermined point such as established by techniques such as surveying etc., or a predetermined distinctive point such as marker embedded into the structure. Accordingly, measurements may be established according to embodiments of the invention with references which are intrinsically linked (i.e. forming part of) or extrinsically linked (i.e. not forming part of) the structure and/or area being characterised and analysed. As such techniques may include a global positioning system, wireless triangulation, wireless multilateration, surveying from a survey reference point, and surveying from a predetermined point on the concrete structure. In some embodiments of the invention an initial reference point may be established and physically identified for subsequent periodic inspections. With location accuracies below 10 cm exploiting ranging techniques by the inventors it would be evident that periodic inspections are now feasible. Further, through the use of multiple measurements obtained with a portable measurement system/or multiple SMAKs embedded within a structure a contour map or multiple contour maps of properties of the structure may be generated. Where embedded SMAKs are employed then these contours maps and/or measurements can be referenced to initial measurements obtained when the structure is initially built, constructed etc.

Figure 7A:
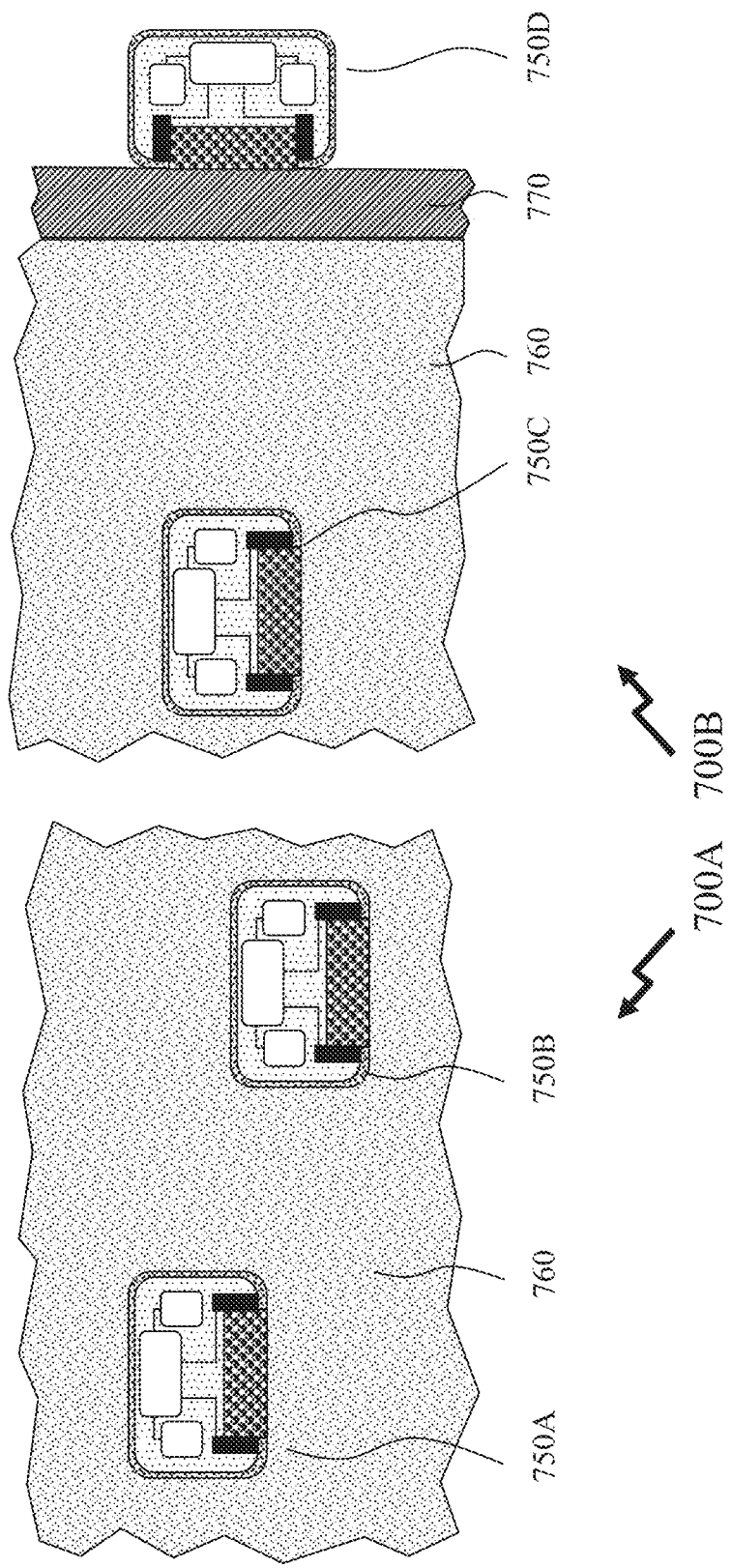
FIG. 7A depicts exemplary embedded sensor configurations according to embodiments of the invention for establishing air content within concrete.
Figure 7B:
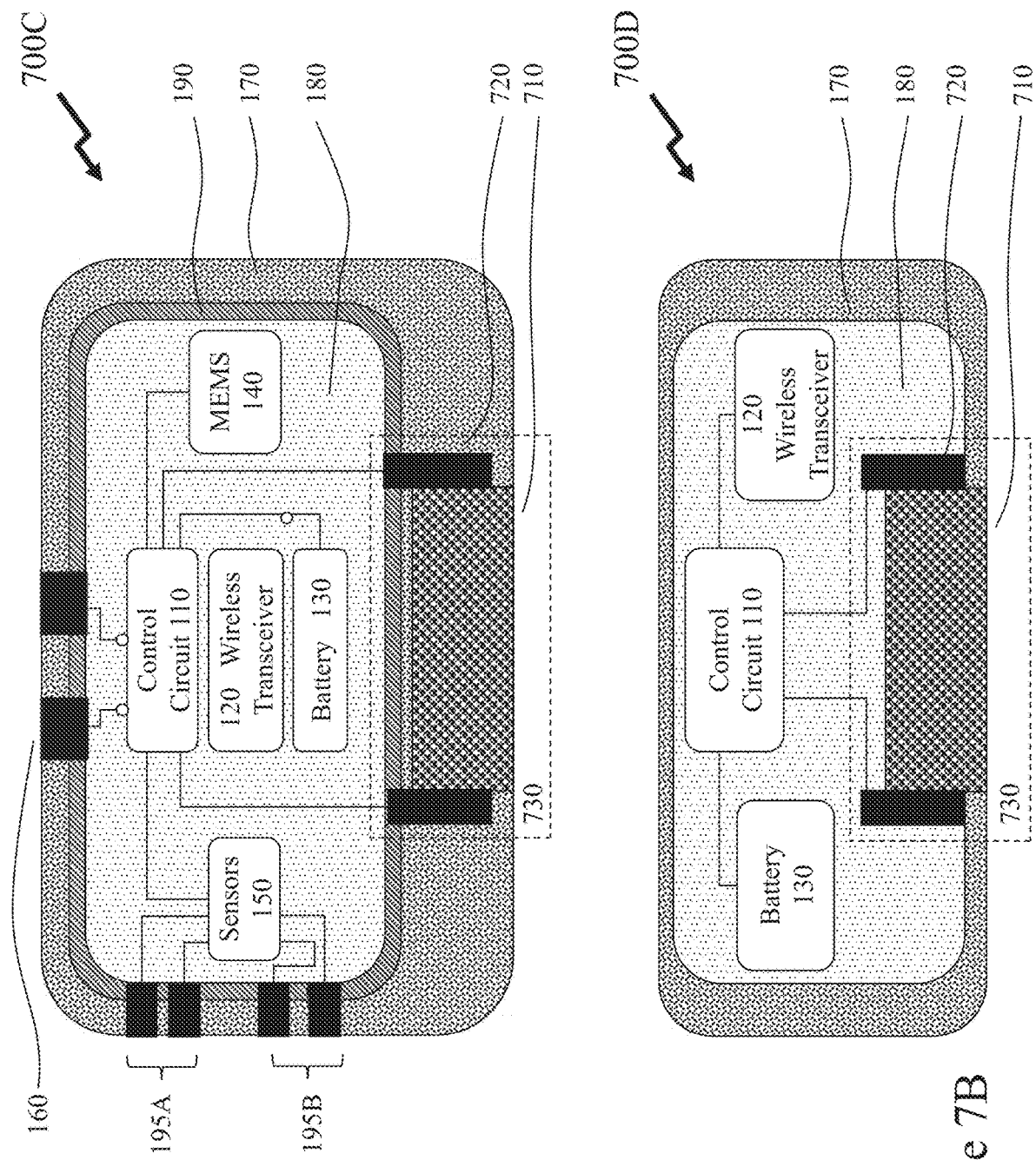
FIG. 7B depicts exemplary embedded sensor concepts according to embodiments of the invention for establishing air content within concrete.

Now referring to FIG. 7A there are depicted first and second configurations 700A and 700B respectively in respect of employing SMAKs such as those described and depicted in FIG. 7B to perform acoustic (ultrasonic) based air content determination of the construction material. Within first configuration 700A first and second SMAKs 750A and 750B respectively are depicted representing a SMAK with an acoustic or ultrasonic transmitter and a SMAK with an acoustic or ultrasonic receiver respectively, or vice-versa. Optionally, a SMAK may operate as both an acoustic or ultrasonic transmitter and a receiver. Accordingly, the first and second SMAKs 750A and 750B can establish the air content of the construction material 760 based upon the timing information relating to the acoustic or ultrasonic signals sent by one and received by the other etc. Optionally, a single acoustic transmitter SMAK may provide acoustic signals to a plurality of acoustic receiver SMAKs.

Within second configuration 700B a single SMAK 710C is depicted embedded together with an acoustic transmitter and/or receiver 750D disposed external to the construction material. In fact, as depicted the acoustic transmitter and/or receiver 750D is disposed with another material 770 between it and the construction material 760. This, may for example, be formwork for poured concrete allowing air content to be established for the concrete as poured and subsequently during curing, etc.

Now referring to FIG. 7B there are depicted exemplary first and second SMAK designs 700C and 700D according to embodiments of the invention for SMAKs incorporating acoustic transmitter elements and/or receiver elements. In first SMAK design 700C the SMAK comprises the control circuit 110, wireless transceiver 120, battery 130, MEMS 140, and sensors 150 which are coupled to first and second SENsor INTerfaces (SENINTs) 195A and 195B. The control circuit 110 is also coupled to contacts 160 and an acoustic transducer 730 comprising a transducer element 710 and drive contacts 720. Accordingly, the control circuit 110 can establish appropriate drive signals to the acoustic transducer 730 such that the SMAK launches acoustic signals. Alternatively, the acoustic transducer 730 may receive acoustic signals and provide converted electrical signals to the control circuit 110. As depicted the first SMAK design 700A comprises an intermediate casing 190 which encapsulates the sensor filler 180, e.g. a foam, air, etc. and is surrounded by an outer shell 170. As depicted the transducer element 710 is entirely external to the intermediate casing 190 and only drive contacts 720 extend through it for the acoustic transducer 730 although other contacts 160 and first and second SENINTs 195A and 195B also do.

In second SMAK design 700D the SMAK is reduced in complexity to the control circuit 110, wireless transceiver 120, and battery 130 together with the acoustic transducer 730 comprising transducer element 710 and resistivity contacts 520. In this embodiment the transducer element 710 is not outside an intermediate casing and is depicted as being within both the outer shell 170 and filler 180 although it would be evident that according to the filler 180 that the outer shell 170 may be omitted.

The control circuit 110 within the first and second SMAK designs 700C and 700D may, for example, comprise a microprocessor or controller, a pulse generator for generating the electrical pulse/signal to drive the acoustic transducer, a pulse detection circuit for detecting the returned converted acoustic pulse/signal, and a timing circuit to determine the timing between the generation of the electrical pulse/signal and receipt of the returned electrical pulse/signal.

Figure 8:
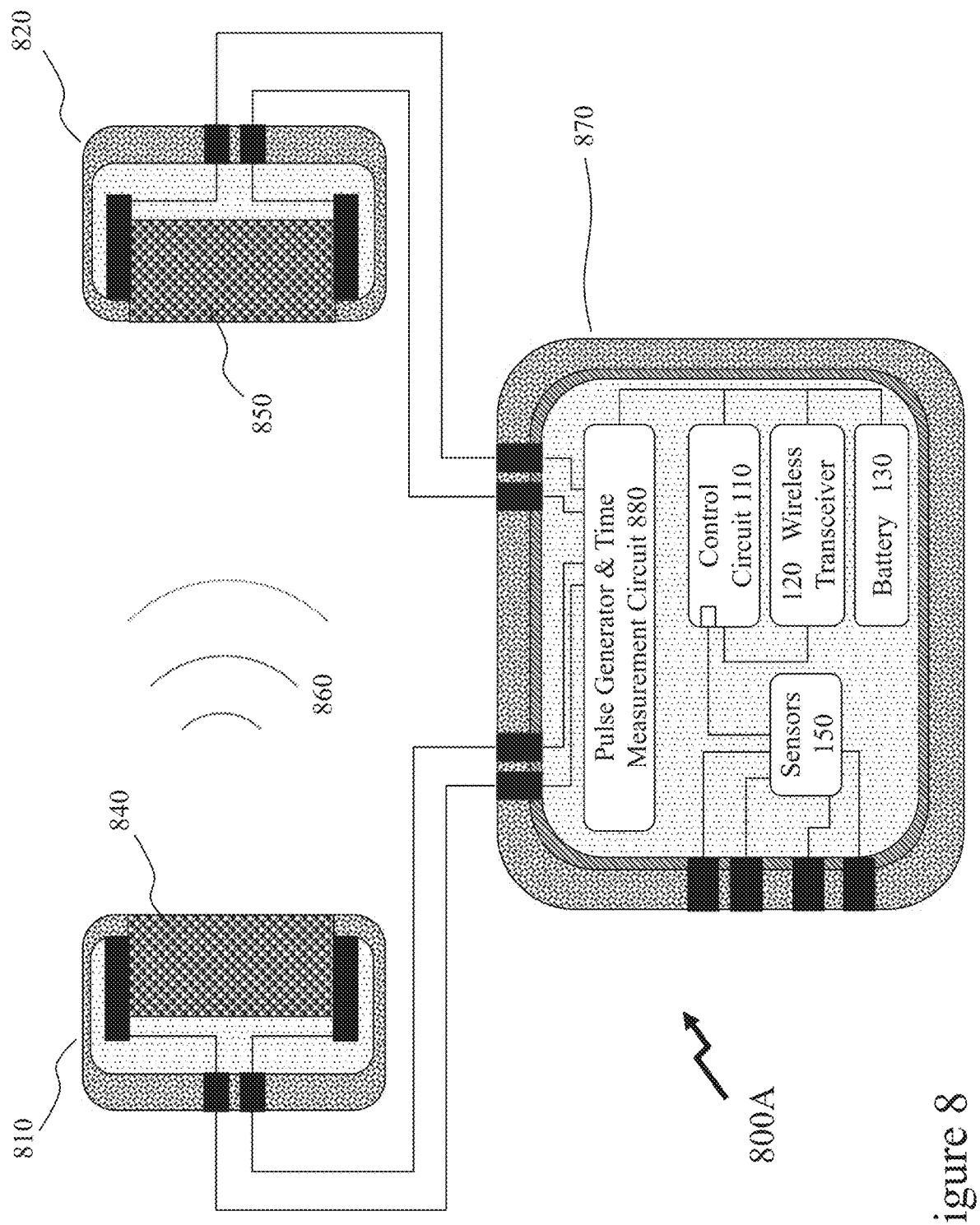
FIG. 8 depicts an exemplary embedded sensor concept according to an embodiment of the invention for establishing voids within concrete exploiting ultrasound.

Referring to FIG. 8 there is depicted a configuration wherein an acoustic transmitter 810 comprising a first transducer element 840 emits acoustic signals which are received by acoustic receiver 820 via the second transducer element 850. Each of the acoustic transmitter 810 and acoustic receiver 820 are wired to a SMAK 870 which comprises a pulse generator and time measurement circuit 880 together with the control circuit 110, wireless transceiver 120, battery 130 and other sensors 150.

Examples of transducer elements 710 and 810 may include, but are not limited to, electromagnetic acoustic transducer (EMAT), piezoelectric transducers such as those exploiting polyvinylidene fluoride (PVDF), loudspeakers such as piezoelectric and electrostatic for example, and microphones such as piezoelectric, fiber optic, and capacitance based for example. Optionally a SMAK may contain one, two or multiple transducer elements acting as acoustic transmitter, acoustic receiver or as both acoustic transmitter and acoustic receiver. Optionally, the outer surface of the SMAK may be the acoustic transducer.

Figure 9A:
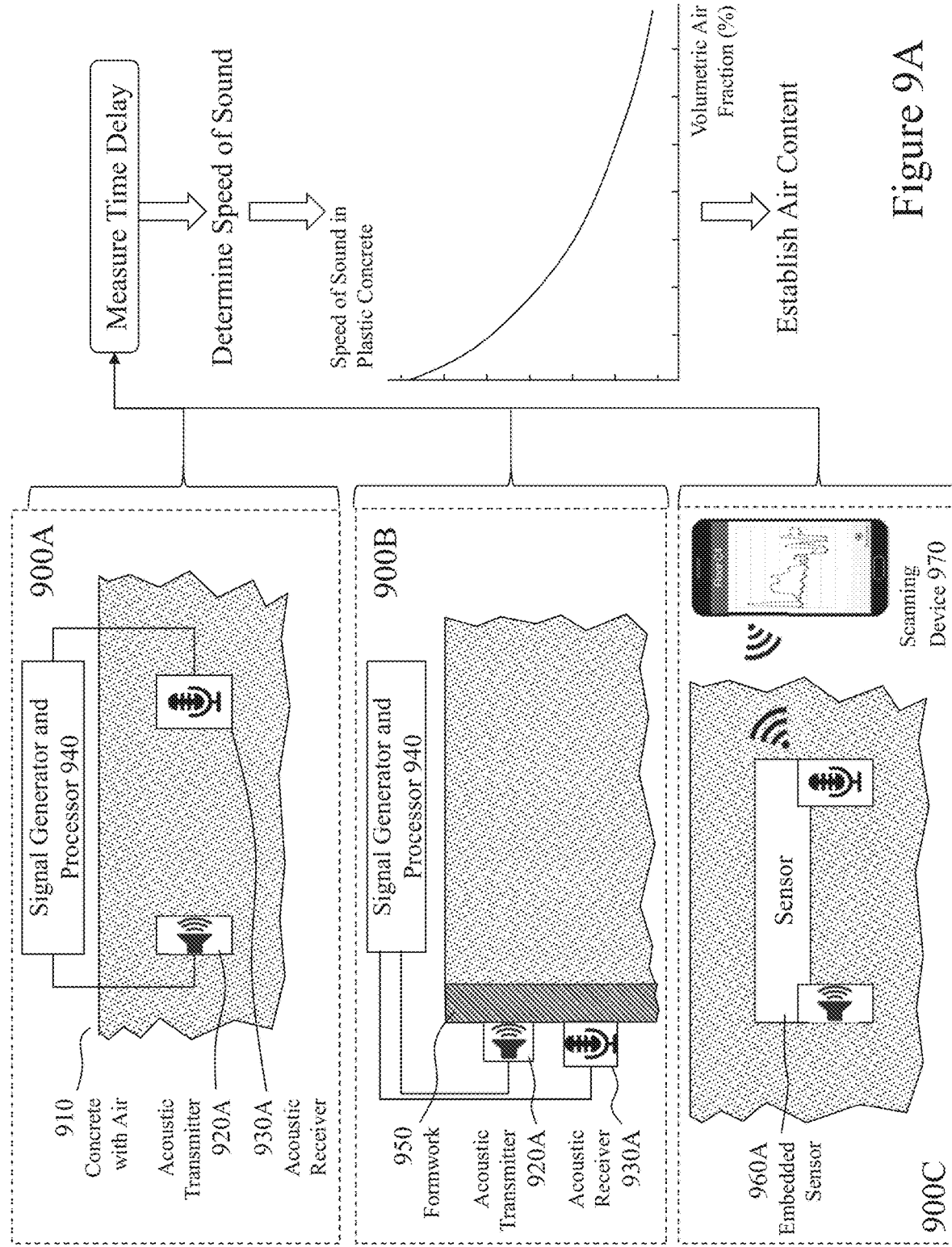
FIGS. 9A and 9B depict exemplary configurations for exploiting embedded sensor devices for establishing air content and concrete characteristics respectively.

Hence, referring to FIG. 9A first to third configurations 900A to 900C are depicted for establishing material properties exploiting acoustic pulses. First configuration 900A comprises an acoustic transmitter 920A embedded within a construction material 910 such as concrete together with an acoustic receiver 930A which is also embedded within the construction material 910. These are electrically connected to a measurement device 940 comprising a signal generator and processor in order to generate the driving signal for the acoustic transmitter 920A, receive the signal from the acoustic receiver 930A and process to determine the speed of sound within the construction material. This is then employed through an appropriate calibration curve either generic to multiple mixes or mix specific to establish the volumetric air fraction within the construction material.

Alternatively, in second configuration 900B the acoustic transmitter 920A and acoustic receiver 930A are both external to the construction material and may have additional material(s) such as formwork disposed between them and the construction material. Accordingly, the acoustic signal propagates within the construction material until reflected from an interface of the construction material such as air on another side of the construction material. Alternatively, in third configuration 900C the acoustic transmitter 920A and acoustic receiver 930A are both embedded within the construction material and form part of an embedded sensor 960A which then wirelessly communicates data to a scanning device 970.

The pulse velocity of longitudinal (compression) stress waves in concrete is related to its dynamic modulus of elasticity, density and Poisson's ratio through well-established formulae. Therefore, the velocity of propagation of ultrasonic pulses can be used to assess the density of concrete. This means that such a measurement can be implemented in assessing cracking, consistency, availability of large voids and occurrence of honeycombing. The method uses transducers that are in contact with the concrete, a pulse generator utilizing a preset frequency, an amplifier, and a time-measuring circuit to detect the velocity of propagation of the acoustic pulse.

Figure 9B:
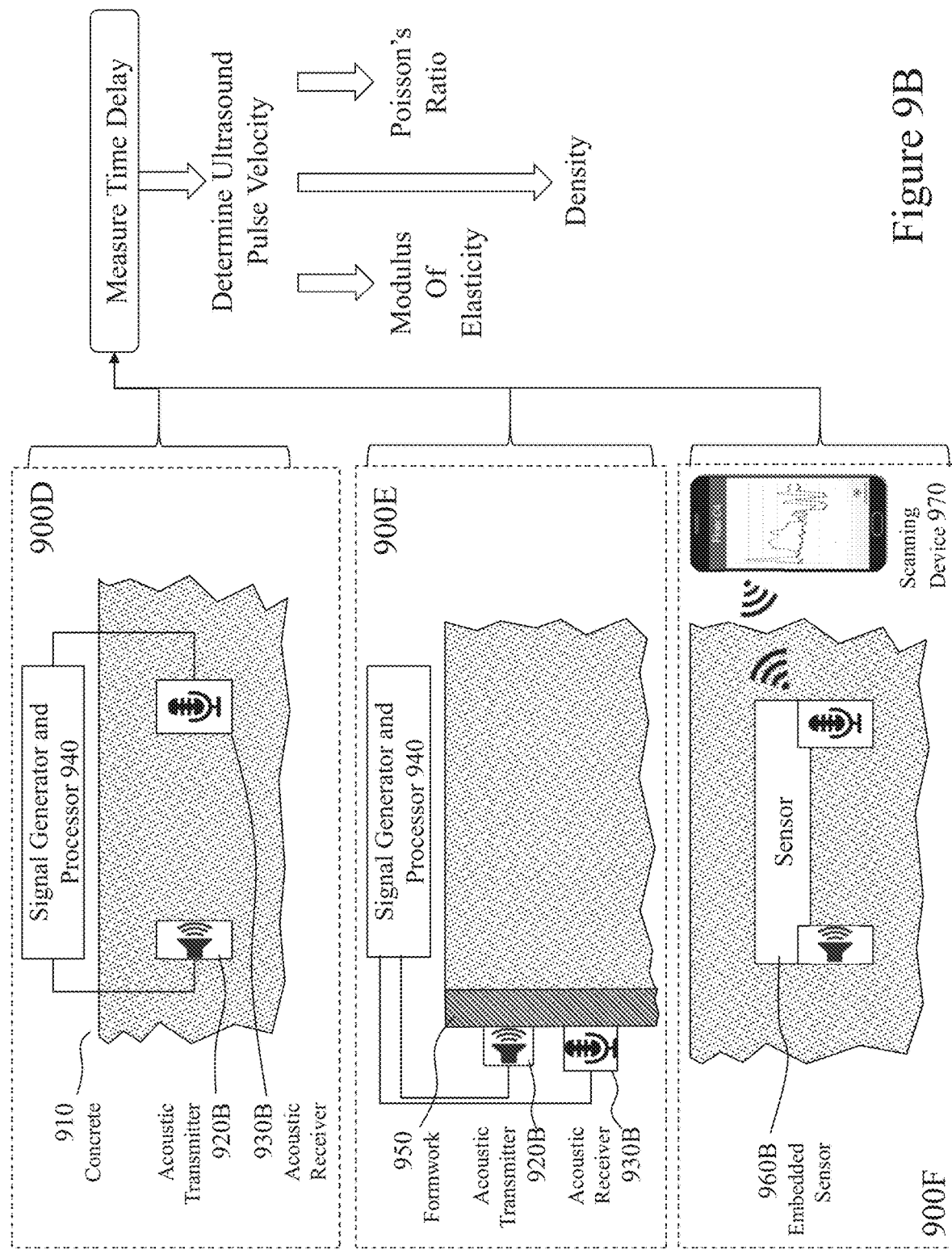

Accordingly, within other embodiments of the invention ultrasonic pulses may be employed such as depicted in FIG. 9B with reference to fourth to sixth configurations 900D to 900F respectively. Third configuration 900D comprises an acoustic transmitter 920B embedded within a construction material 910 such as concrete together with an acoustic receiver 930B which is also embedded within the construction material 910. These are electrically connected to a measurement device 940 comprising a signal generator and processor in order to generate the driving signal for the acoustic transmitter 920B, receive the signal from the acoustic receiver 930B and process to determine the speed of sound within the construction material. This is then employed through an appropriate calibration curve either generic to multiple mixes or mix specific to establish the volumetric air fraction within the construction material.

Alternatively, in fifth configuration 900E the acoustic transmitter 920B and acoustic receiver 930B are both external to the construction material and may have additional material(s) such as formwork disposed between them and the construction material. Accordingly, the acoustic signal propagates within the construction material until reflected from an interface of the construction material such as air on another side of the construction material. Alternatively, in sixth configuration 900F the acoustic transmitter 920B and acoustic receiver 930B are both embedded within the construction material and form part of an embedded sensor 960B which then wirelessly communicates data to a scanning device 970.

The inventors have established that there exists a relationship between the strength of concrete and its formation factor. Accordingly, with a knowledge of formation factor the strength of the concrete can be derived. The relationship between strength and formation factor may be established, for example, for a specific mix at a specific air content, for a specific mix over a range of air contents, for all mixes at a specific air content, for all mixes over a range of air contents, for a specific set or range of mixes at a specific air content, and for a specific set or range of mixes over a range of air contents.

Figure 10:
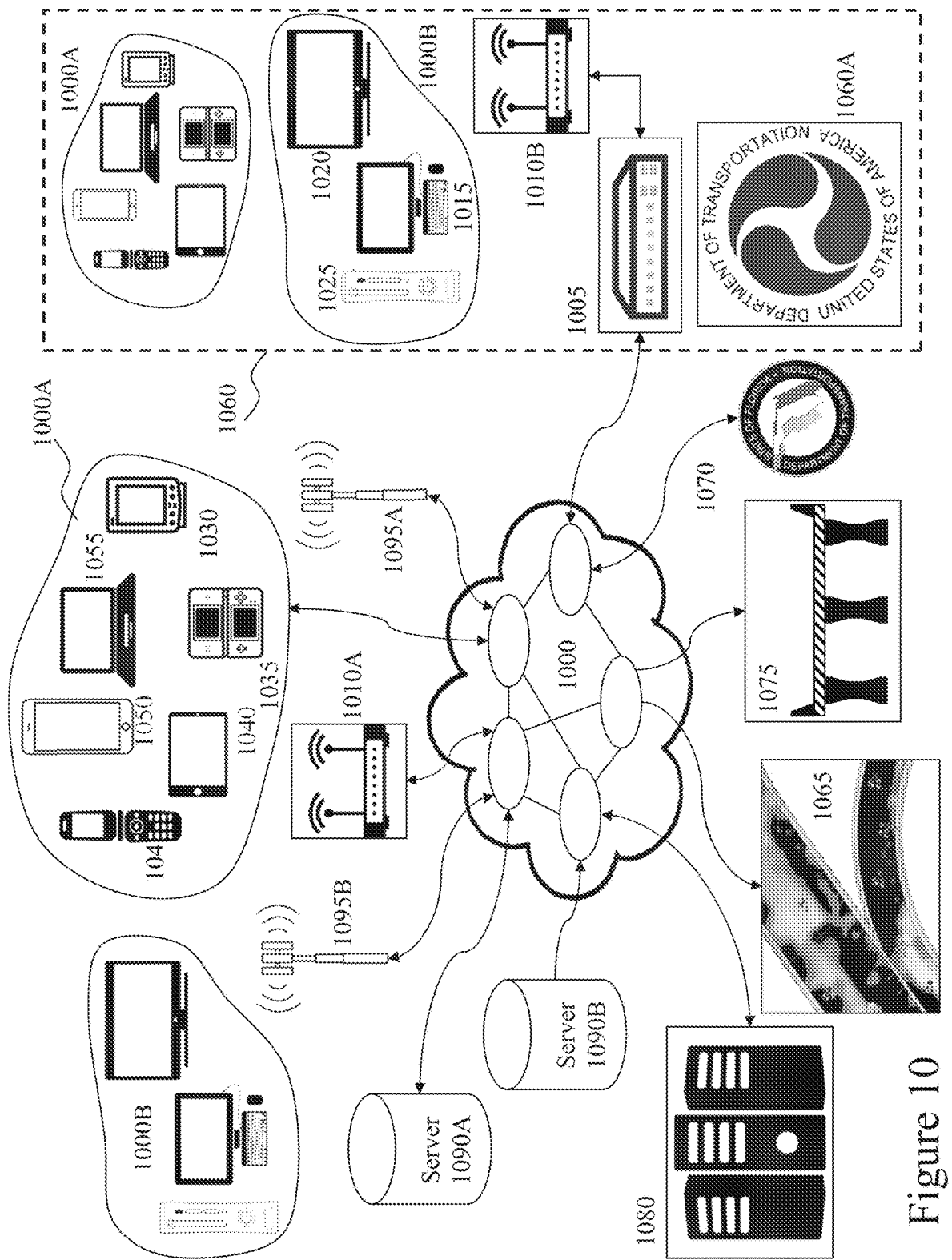
FIG. 10 depicts a network supporting communications to and from electronic devices implementing contextual based UIs according to embodiments of the invention.

Exemplary Network and Device Configurations for Construction Material Characterisation Now referring to FIG. 10 there is depicted a network 1000 supporting communications to and from electronic devices implementing contextual based UIs according to embodiments of the invention. As shown first and second user groups 1000A and 1000B respectively interface to a telecommunications network 1000. Within the representative telecommunication architecture, a remote central exchange 1080 communicates with the remainder of a telecommunication service providers network via the network 1000 which may include for example long-haul OC-48/OC-192 backbone elements, an OC-48 wide area network (WAN), a Passive Optical Network, and a Wireless Link. The central exchange 1080 is connected via the network 1000 to local, regional, and international exchanges (not shown for clarity) and therein through network 1000 to first and second wireless access points (AP) 1095A and 1095B respectively which provide Wi-Fi cells for first and second user groups 1000A and 1000B respectively. Also connected to the network 1000 are first and second Wi-Fi nodes 1010A and 1010B, the latter of which being coupled to network 1000 via router 1005. Second Wi-Fi node 1010B is associated with Government Body 1060A and environment 1060 within which are first and second user groups 1000A and 1000B. Second user group 1000B may also be connected to the network 1000 via wired interfaces including, but not limited to, DSL, Dial-Up, DOCSIS, Ethernet, G.hn, ISDN, MoCA, PON, and Power line communication (PLC) which may or may not be routed through a router such as router 1005.

Within the cell associated with first AP 1010A the first group of users 1000A may employ a variety of portable electronic devices including for example, laptop computer 1055, portable gaming console 1035, tablet computer 1040, smartphone 1050, cellular telephone 1045 as well as portable multimedia player 1030. Within the cell associated with second AP 1010B are the second group of users 1000B which may employ a variety of fixed electronic devices including for example gaming console 1025, personal computer 1015 and wireless/Internet enabled television 1020 as well as cable modem 1005.

Also connected to the network 1000 are first and second APs which provide, for example, cellular GSM (Global System for Mobile Communications) telephony services as well as 3G and 4G evolved services with enhanced data transport support. Second AP 1095B provides coverage in the exemplary embodiment to first and second user groups 1000A and 1000B. Alternatively the first and second user groups 1000A and 1000B may be geographically disparate and access the network 1000 through multiple APs, not shown for clarity, distributed geographically by the network operator or operators. First AP 1095A as shown provides coverage to first user group 1000A and environment 1060, which comprises second user group 1000B as well as first user group 1000A. Accordingly, the first and second user groups 1000A and 1000B may according to their particular communications interfaces communicate to the network 1000 through one or more wireless communications standards such as, for example, IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-2000. It would be evident to one skilled in the art that many portable and fixed electronic devices may support multiple wireless protocols simultaneously, such that for example a user may employ GSM services such as telephony and SMS and Wi-Fi/WiMAX data transmission, VOIP and Internet access. Accordingly, portable electronic devices within first user group 1000A may form associations either through standards such as IEEE 802.15 and Bluetooth as well in an ad-hoc manner.

Also connected to the network 1000 are concrete mapping environment 1065, State Body 1070, and Bridge Structure environment 1075 as well as first and second servers 1090A and 1090B which together with others not shown for clarity, may host according to embodiments of the inventions multiple services associated with one or more organizations, including but not limited to, a provider of the software operating system(s) and/or software application(s) associated with the electronic device(s), a provider of the electronic device, provider of one or more aspects of wired and/or wireless communications, provider of the electrical measurement devices, provider of mapping analysis software, provider of electrical measurement analysis software, global position system software, materials databases, building databases, regulatory databases, license databases, construction organizations, websites, and software applications for download to or access by FEDs, PEDs, and electrical measurement systems. First and second servers 1090A and 1090B may also host for example other Internet services such as a search engine, financial services, third party applications and other Internet based services.

Accordingly, it would be evident to one skilled in the art that electrical measurement systems and/or rebar corrosion analysis according to embodiments of the invention described above in respect of FIGS. 1 to 9B and 11 to 22 may be connected to a communications network such as network 1000 either continuously or intermittently. It would be further evident that the electrical resistivity measurements of concrete and/or rebar together with the analysis of the measurements and their mapping may be triggered as a result of activities triggered by, for example, the Government Body 1060A and/or State Body 1070 in order to address regulatory requirements, safety concerns etc.

Accordingly, the engineers, workers and/or technicians who will be performing the measurements may be able to access Bridge Structure Environment 1075 to obtain architect drawings, engineering data, design data, etc. relating to the concrete structure being assessed. It would be evident that other databases addressing other environments such as for example, shopping malls, road surfaces, public walkways, residential housing, and commercial buildings may be accessed where the requirements for assessment relate to these structures and the regulatory bodies may be similarly transportation or include others such as Department of Housing, Federal Highway Administration, and Bureau of Industry and Security. Where all or part of the structure being assessed has been previously assessed then data may be retrieved from the Concrete Mapping Environment for example. It would be evident that with coordinated based measurement acquisition that an engineer may view in real time a contour map of the structure being assessed as the data is acquired and accordingly may ask for additional measurements or repeated measurements to be performed. Additionally, previous contour mapping and electrical measurements may allow for targeted re-assessment of areas of concern at a different frequency to that of the overall structure.

Figure 11:
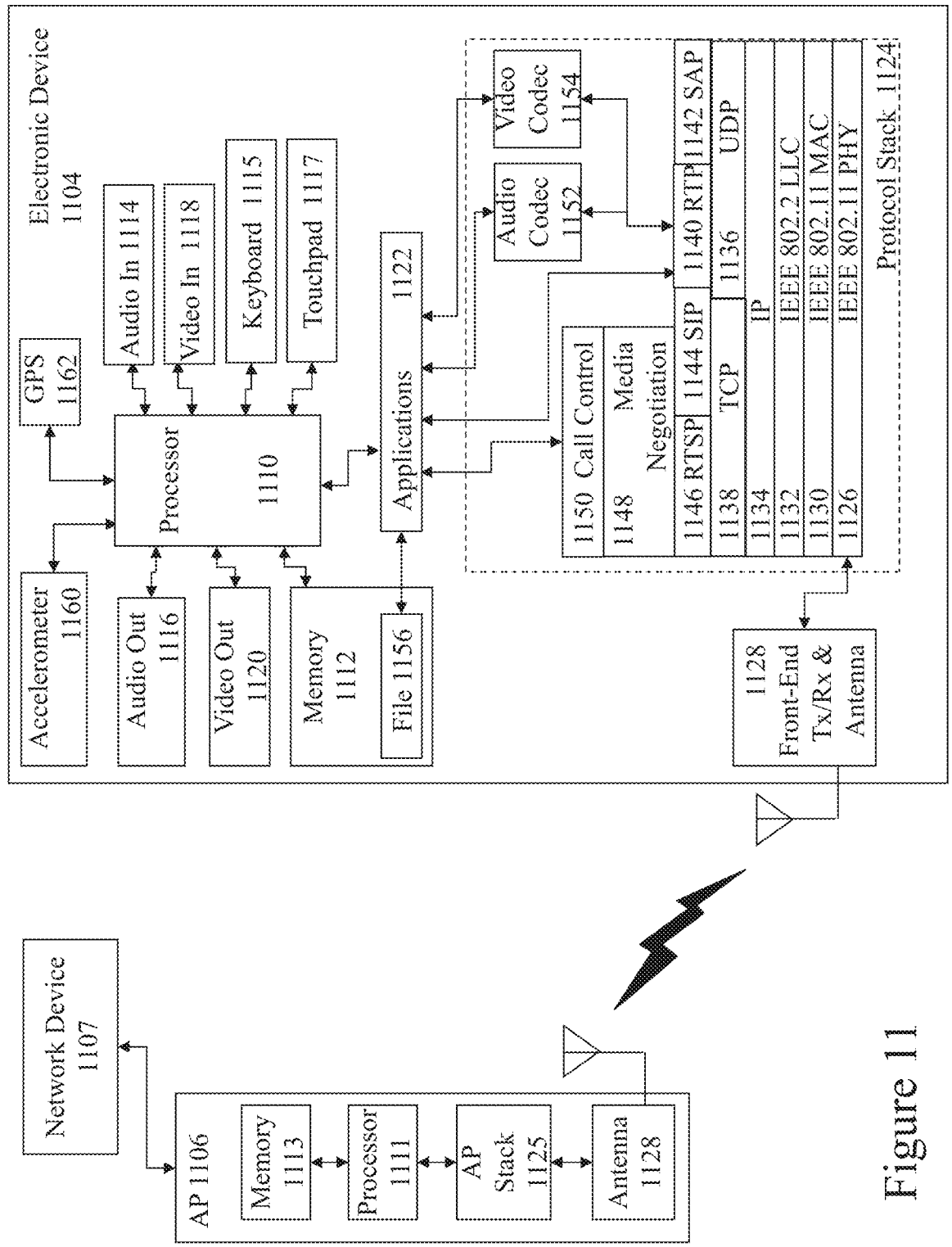
FIG. 11 depicts an electronic device and network access point supporting contextual based UIs according to embodiments of the invention.

Now referring to FIG. 11 there is depicted an electronic device 1104 and network access point 1107 supporting contextual based UIs according to embodiments of the invention. Electronic device 1104 may for example be a portable electronic device or a fixed electronic device and may include additional elements above and beyond those described and depicted. Also depicted within the electronic device 1104 is the protocol architecture as part of a simplified functional diagram of a system 1100 that includes an electronic device 1104, such as a smartphone 1055, an access point (AP) 1106, such as first AP 1010, and one or more network devices 1107, such as communication servers, streaming media servers, and routers for example such as first and second servers 1090A and 1090B respectively. Network devices 1107 may be coupled to AP 1106 via any combination of networks, wired, wireless and/or optical communication links such as discussed above in respect of FIG. 10. The electronic device 1104 includes one or more processors 1110 and a memory 1112 coupled to processor(s) 1110. AP 1106 also includes one or more processors 1111 and a memory 1113 coupled to processor(s) 1111. A non-exhaustive list of examples for any of processors 1110 and 1111 includes a central processing unit (CPU), a digital signal processor (DSP), a reduced instruction set computer (RISC), a complex instruction set computer (CISC) and the like. Furthermore, any of processors 1110 and 1111 may be part of application specific integrated circuits (ASICs) or may be a part of application specific standard products (ASSPs). A non-exhaustive list of examples for memories 1112 and 1113 includes any combination of the following semiconductor devices such as registers, latches, ROM, EEPROM, flash memory devices, non-volatile random-access memory devices (NVRAM), SDRAM, DRAM, double data rate (DDR) memory devices, SRAM, universal serial bus (USB) removable memory, and the like.

Electronic device 1104 may include an audio input element 1114, for example a microphone, and an audio output element 1116, for example, a speaker, coupled to any of processors 1110. Electronic device 1104 may include a video input element 1118, for example, a video camera, and a video output element 1120, for example an LCD display, coupled to any of processors 1110. Electronic device 1104 also includes a keyboard 1115 and touchpad 1117 which may for example be a physical keyboard and touchpad allowing the user to enter content or select functions within one of more applications 1122. Alternatively, the keyboard 1115 and touchpad 1117 may be predetermined regions of a touch sensitive element forming part of the display within the electronic device 1104. The one or more applications 1122 that are typically stored in memory 1112 and are executable by any combination of processors 1110. Electronic device 1104 also includes accelerometer 1160 providing three-dimensional motion input to the process 1110 and GPS 1162 which provides geographical location information to processor 1110.

Electronic device 1104 includes a protocol stack 1124 and AP 1106 includes a communication stack 1125. Within system 1100 protocol stack 1124 is shown as IEEE 802.11 protocol stack but alternatively may exploit other protocol stacks such as an Internet Engineering Task Force (IETF) multimedia protocol stack for example. Likewise, AP stack 1125 exploits a protocol stack but is not expanded for clarity. Elements of protocol stack 1124 and AP stack 1125 may be implemented in any combination of software, firmware and/or hardware. Protocol stack 1124 includes an IEEE 802.11-compatible PHY module 1126 that is coupled to one or more Front-End Tx/Rx & Antenna 1128, an IEEE 802.11-compatible MAC module 1130 coupled to an IEEE 802.2-compatible LLC module 1132. Protocol stack 1124 includes a network layer IP module 1134, a transport layer User Datagram Protocol (UDP) module 1136 and a transport layer Transmission Control Protocol (TCP) module 1138.

Protocol stack 1124 also includes a session layer Real Time Transport Protocol (RTP) module 1140, a Session Announcement Protocol (SAP) module 1142, a Session Initiation Protocol (SIP) module 1144 and a Real Time Streaming Protocol (RTSP) module 1146. Protocol stack 1124 includes a presentation layer media negotiation module 1148, a call control module 1150, one or more audio codecs 1152 and one or more video codecs 1154. Applications 1122 may be able to create, maintain and/or terminate communication sessions with any of devices 1107 by way of AP 1106. Typically, applications 1122 may activate any of the SAP, SIP, RTSP, media negotiation and call control modules for that purpose. Typically, information may propagate from the SAP, SIP, RTSP, media negotiation and call control modules to PHY module 1126 through TCP module 1138, IP module 1134, LLC module 1132 and MAC module 1130.

It would be apparent to one skilled in the art that elements of the electronic device 1104 may also be implemented within the AP 1106 including but not limited to one or more elements of the protocol stack 1124, including for example an IEEE 802.11-compatible PHY module, an IEEE 802.11-compatible MAC module, and an IEEE 802.2-compatible LLC module 1132. The AP 1106 may additionally include a network layer IP module, a transport layer User Datagram Protocol (UDP) module and a transport layer Transmission Control Protocol (TCP) module as well as a session layer Real Time Transport Protocol (RTP) module, a Session Announcement Protocol (SAP) module, a Session Initiation Protocol (SIP) module and a Real Time Streaming Protocol (RTSP) module, media negotiation module, and a call control module.

Portable and fixed electronic devices represented by electronic device 1104 may include one or more additional wireless or wired interfaces in addition to the depicted IEEE 802.11 interface which may be selected from the group comprising IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, IMT-2000, DSL, Dial-Up, DOCSIS, Ethernet, G.hn, ISDN, MoCA, PON, and Power line communication (PLC).

Concrete RH Profile Prediction/Calculation; Using RH Sensor Data Embedded with Algorithms/Software.

To predict the RH profile and moisture content at different depths from the surface of concrete (with unknown properties and pore network), a sensor can be first embedded near the surface of concrete to monitor the short-term changes in the RH and moisture from fresh stage (when concrete has 100% RH). Ambient RH needs to be recorded at the same time. This can either be obtained from the weather history data or another sensor placed outside concrete. Then, this data can be used through inverse modelling algorithms to develop an accurate model for the pore structure and pore connectivity properties of the concrete material. Finally, knowing the forecast or assuming the ambient RH values for future dates, the constructed model can be utilized to predict the rate of drying, moisture vapor emission rate, and RH and moisture content at a particular depth from the surface at a specific time in the future.

The deployment of a SMAK within a structure allows for the measurement of one or more material parameters and the determination from these of one or more other parameters relating to the material. Additionally, these measurements also allow for the determination from these of one or more other parameters relating to the material at a different position within the structure. For example, referring to FIG. 12 the measurement of relative humidity (RH) at a first depth X is employed in the projection of relative humidity at a different depth Y. Accordingly a sensor (SMAK) 1210 is embedded within the material 1220, e.g. concrete, at a depth X. Extracted data from the sensor 1210 yields a first RH curve 1230 with time. Typically, this is a series of discrete measurements over time rather than a continuous measurement, but it may be. These results are fed into a computational model 1240 which establishes a second RH curve 1250 at a second depth Y. Accordingly, based upon this analysis not only can the current RH be projected at the depth Y but also a forward projecting analysis undertaken to establish a predicted RH at different points forward in time. For example, a maximum RH may be established at the depth Y during the curing stage of the material 1220 in order to determine the point at which the formwork is removed. Longer term the RH projections may be employed to assess water penetration into the structure and accordingly when would water reach metal reinforcing structures for example. Similar measurements and predictions can be made for other aspects of the material such as chloride penetration and similarly projected forward. Optionally, computational algorithms may also be employed to determine the equilibrium relative humidity after covering the concrete with flooring materials, membranes, etc.

Sensor Activation

In order to maximise sensor lifetime maintaining the battery life required for the sensing application is important. Accordingly, keeping the sensors inactive during their shelf life or transportation prior to use is beneficial. Accordingly, there is a requirement to activate the sensors when they are at the job site and prior to their installation so that they could be detected and connected to by the scanning devices. Alternatively, the sensors may be activated prior to deployment within the construction material at the point of manufacture or transportation to the job site. The hibernating (inactive) sensors will become temporarily/permanently active once triggered through one or more activation methods.

Within an embodiment of the invention the temporarily activated sensors could then be connected to via a scanning device and become permanently active and start their main function (for example datalogging). It would be beneficial that activating the sensors requires little to no additional equipment and must be as simple as possible to facilitate on site activation by unskilled individuals. Within embodiments of the invention the temporarily activated sensors could then be connected to via a scanning device and become inactive after a predetermined period of time or establish an operating mode with a generally low power state (sleep mode) with periodic activation to perform a measurement or transmit their data to a scanning device. Optionally, the devices within the generally low power state perform these periodic measurements according to a predetermined schedule and maintain this cycle unless an activation is received from a scanning device. As noted above these periodic measurements may be at a higher frequency during initial deployment and then at increasing lower frequencies established either based upon elapsed time or one or more determined characteristics of the material being monitored.

Figure 13:
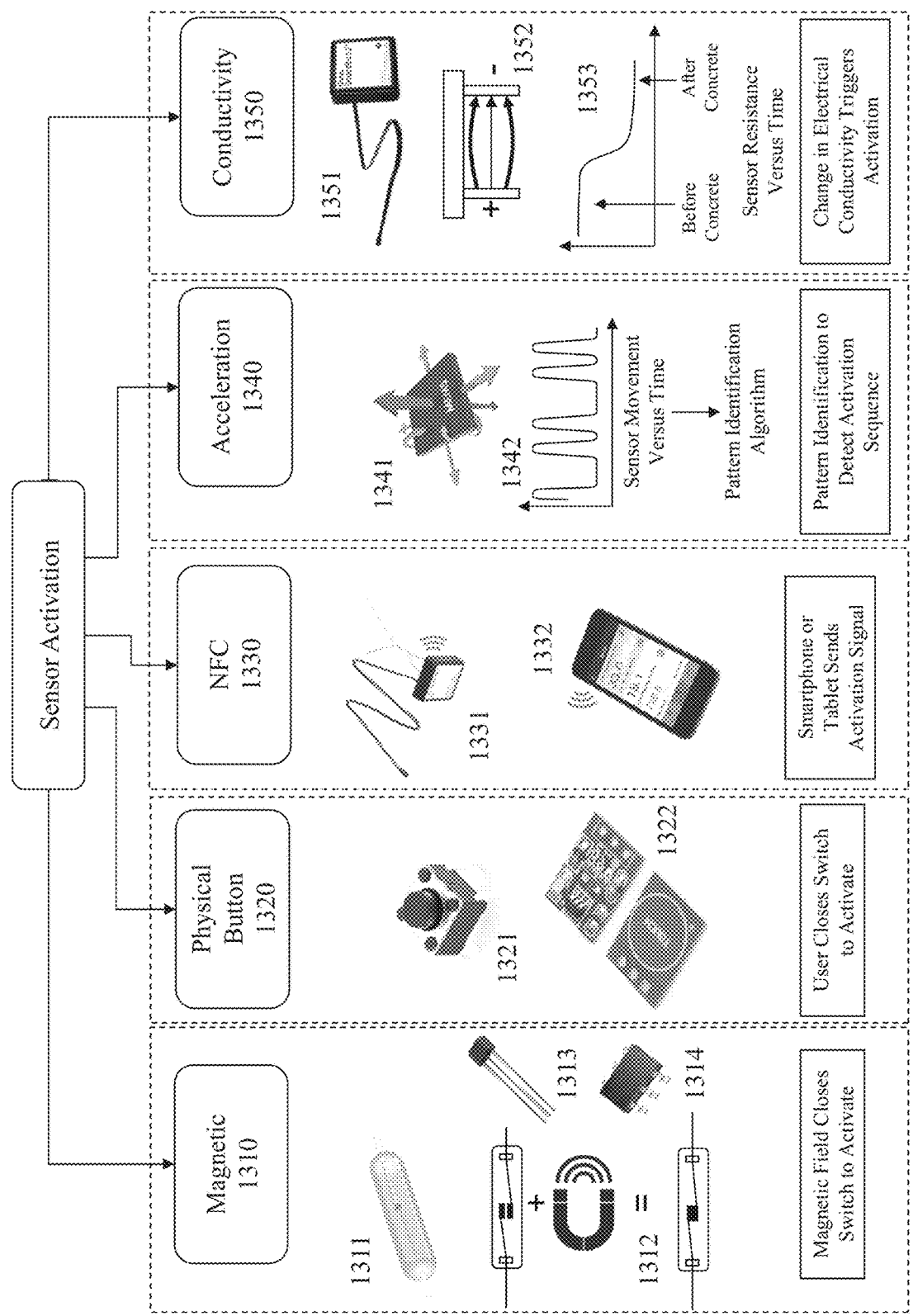
FIG. 13 depicts schematically examples of activation mechanisms for embedded sensors according to embodiments of the invention.

Activation of the SMAKs within embodiments of the invention may exploit one or more methods as depicted in FIG. 13. However, it would be evident that other sensor activation techniques may also be employed or that a combination of activation mechanisms may be required to activate a SMAK to avoid incorrect activation. As depicted in FIG. 13 the techniques include, but not limited to:

Magnetic: A magnetic field sensor within the SMAK may be employed to detect a request by the user to activate the sensor. Accordingly, as depicted in FIG. 13 within first block 1310 a reed switch 1311 is depicted wherein bringing a magnet 1312 into proximity of a SMAK comprising the reed switch at a certain predefined location closes the switch thereby activating the sensor. Alternately, solid state magnetically activated switches may be employed such as a Hall sensor 1313 and a magnetoresistive circuit 1314.

Button: As depicted in second block 1320 a physical switch may be employed as part of the SMAK such as, for example, a push button 1321 covered within a waterproof elastic membrane may be employed to allow a user to activate the sensor. Alternatively, a touch sensitive "button" 1322 may be provided.

Near Field Communication (NFC): A variety of electronic devices such as smartphones, tablets, dataloggers etc. are capable of communicating wireless through one or more NFC protocols. The NFC signal as depicted within third block 1330 exploits a wireless signal from a scanning device 1332 which can be received and translated into a request to activate the sensor 1331. This will then activate the main wireless communication process enabling the sensor to start logging and connecting with the scanning devices. Optionally, within an embodiment of the invention the initial NFC communication may be sufficient to power a predetermined portion of the SMAK thereby initiating an initial connection of the battery to the electronics within the SMAK such that the device is then self-powered from that point on. Accordingly, unlike magnetic and button based activations this as well as acceleration and conductivity described below require part of the sensor be active all the time to monitor for the activation signal.

Acceleration (Shaking, Impact etc.): Where the SMAK incorporates a sensor capable of detecting vibration and/or acceleration and is in a low power mode then a predetermined pattern of impact/acceleration may trigger the SMAK into an active mode where the predetermined pattern allows for the trigger pattern to be distinguished from an unintentional initiation. This being depicted in fourth block 1340 wherein a microelectromechanical system (MEMS) accelerometer 1341 generates an output signal 1342 in dependence upon motion and this is monitored for a match to a predetermined pattern. The predetermined pattern may for example be an intentional human generated acceleration via shaking the sensor or predetermined periodic motion such as where the sensor is within the rotating drum of a concrete truck etc. Such predetermined patterns allow distinguishing of the intentional activation versus unintentional machine/setup generated vibrations etc.

Conductivity: Activation may also be triggered through the completion of an electrical circuit between a pair of electrical contacts upon the outer surface of the SMAK as depicted in fifth block 1350. This may, for example, be the same pair of electrical contacts which subsequently measure the conductivity of a material the SMAK is embedded within. Accordingly, as depicted the sensor 1351 applies a voltage to a first electrode and measures the resistance to a second electrode wherein the change in conductivity is detected as a drop in resistance or current flow through completion of the electrical circuit from the first electrode to the second electrode by the conductive material surrounding the sensor, e.g. wet concrete. The resulting change in the monitored characteristic triggers the sensor to move from a low power mode to one where measurements are logged etc. Alternatively, the contacts may be a different pair of contacts as the contacts for the measurement apply a voltage or current. Accordingly, the triggering may be via a user's finger touching the SMAK or the SMAK being deployed within an electrically conductive medium, such as wet concrete.

In-Situ Workability/Slump Measurements

The slump of concrete is evaluated at present using a slump test wherein a cone is filled with the concrete and subsequently after removal of the cone the resulting slump of the concrete is measured. However, this measurement must be made at the work site either before, during or after a pour wherever the operator can do so on the work site. Accordingly, it would be beneficial to provide an automated measurement of workability/slump within the truck transporting the concrete to the work site. The drum of a concrete truck rotates with a blade or blades, typically a spiral blade, that continues to mix the concrete during transportation. Optionally, one or more additions may be made to the concrete during transportation such as water or an admixture wherein the rotation and blade ensure thorough mixing.

As the drum rotates the displacement of the plastic concrete within the mixer varies according to its characteristics (such as viscosity, consistency and yield stress). Accordingly, the displacement of the plastic concrete within the mixer can be determined through resistivity meters fixed at the mixer wall such that the measurement system continuously collects resistivity data which can be correlated to the duration of contact between the concrete mixture and the plurality of sensors for each rotation. Knowing this duration at each rotation cycle, the extent of displacement of concrete within the mixer can be determined and correlated to the slump/workability of the concrete mixture. The rotation rate of the mixer drum may be derived from the resistivity data, from a different sensor, or from the controller of the motor driving the drum for example.

Figure 14:
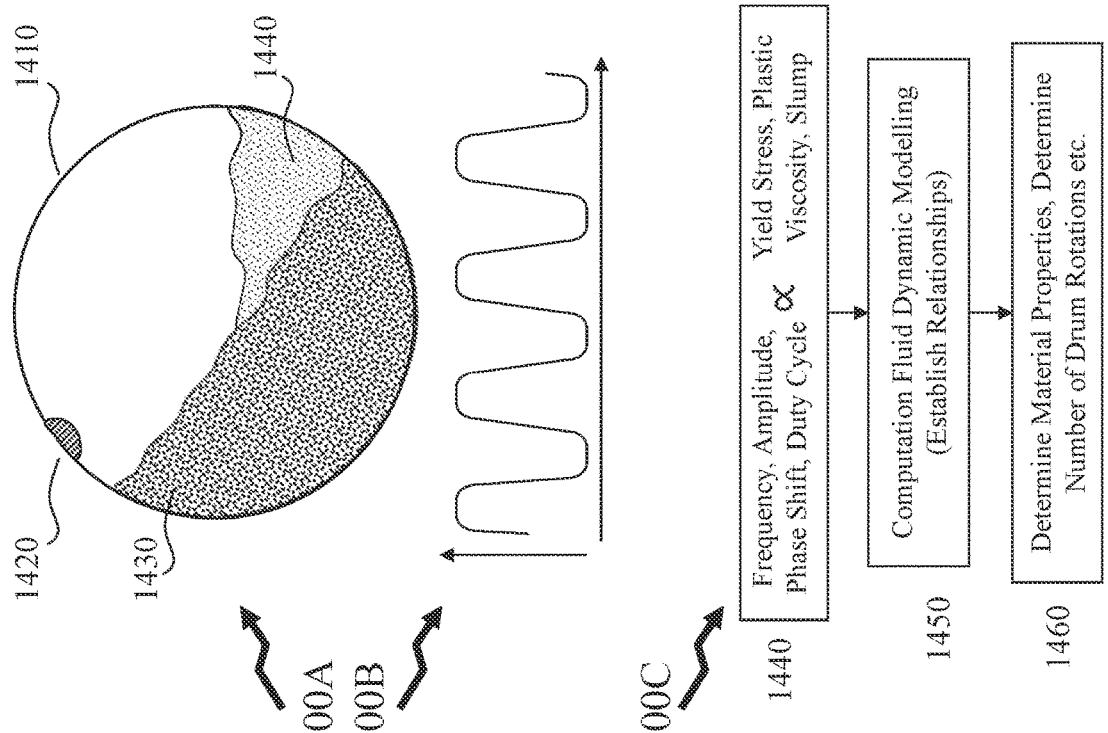
FIG. 14 depicts schematically determination of workability (slump) during transportation of concrete according to an embodiment of the invention.
Figure 12:
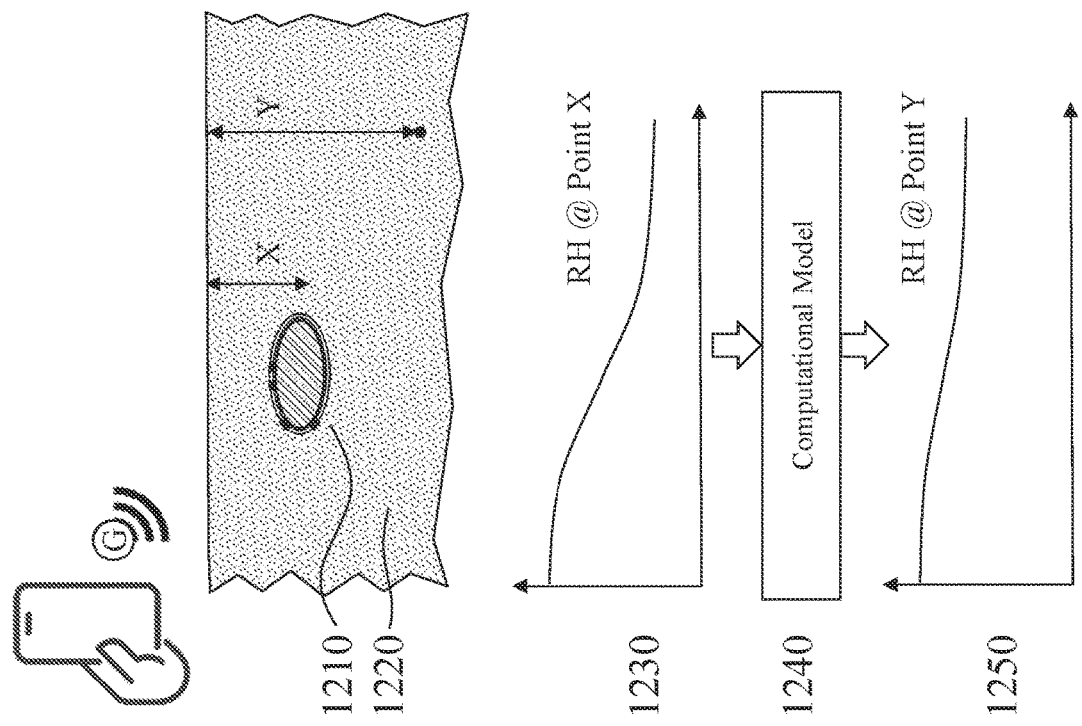
FIG. 12 depicts schematically the determination of relative humidity at a point within a structure based upon characterization at a different point within the structure.

This is depicted within FIG. 14 wherein first image 1400A depicts schematically the drum 1410 with an electrical resistivity sensor 1420 deployed upon the drum 1410. At rest the concrete mixture fills the bottom of the drum as first material 1440 but as the drum 1410 rotates the concrete mixture is rotated around the drum 1410 according to the properties of the concrete mixture, this being depicted as second material 1430. Accordingly, the electrical resistivity monitored by the sensor 1420 exhibits a time dependent response as indicated in second image 1400B wherein the electrical resistivity is high when the sensor 1420 is in the air and low when the sensor 1420 is within the concrete material. Accordingly, referring to third image 1400C a schematic flow diagram of analysis is presented wherein in first block 1440 the frequency, amplitude, phase shift (between the resistivity fluctuation cycles and the drum revolution cycles), and duty cycle of the electrical resistivity measurement are related to the yield stress, plastic viscosity and slump. In second block 1450 computational fluid dynamic (CFD) modelling is employed to establish the relationships between these parameters allowing in third block 1460 for the material properties from the measured response of the sensor 1420 during rotation of the drum 1410. Additionally, the measured response of the sensor 1420 during rotation of the drum 1410 allows for determination of frequency of rotation, number of rotations of drum completed during transportation of the concrete etc.

Embedded Chloride and Corrosion Monitoring Sensors

Chloride-sensitive/selective electrodes in which a metal (or a metal wire) is surrounded by a solution, a coating or deposits of its oxide or its chloride solution (such as Ag/AgCl electrodes or Ir/IrO electrodes) display an electrical potential that is dependent on the surrounding environment. The dependence of the potential of this electrode on the chloride content is well-established and follows Nernst Law. Therefore, the electrical potential of this electrode, measured by means of another half-cell, can indicate the concentration of chlorides in the surrounding medium. This is possible through pre-determined calibration formulae in which the relationship between the electrode potential and the chloride concentration is determined. Such a chloride-sensitive/selective electrode may form part of a SMAK according to an embodiment of the invention.

Figure 15A:
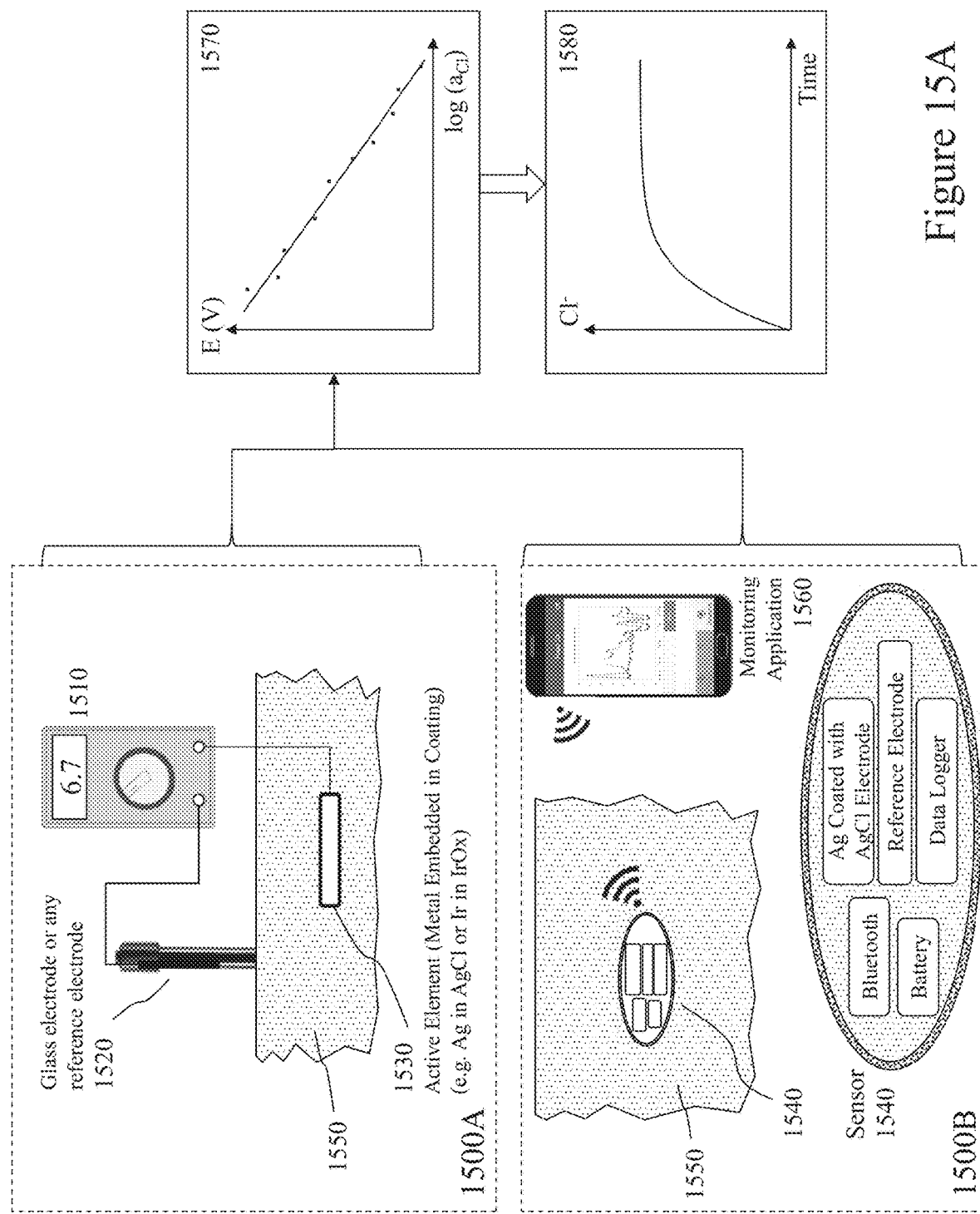
FIG. 15A depicts exemplary embedded and partially embedded sensor configurations for establishing chloride ion levels according to embodiments of the invention.

FIG. 15A there are depicted exemplary embedded and partially embedded sensor configurations for establishing chloride ion levels according to embodiments of the invention within first and second images 1500A and 1500B respectively. Within first image 1500A a partially embedded sensor configuration is depicted wherein a measurement device 1510 is connected to a reference electrode 1520, e.g. a glass electrode as known in the art, connected to the surface of the concrete as described above in respect of FIG. 4B or via a conductive pad such as described in respect of FIG. 3. The device 1510 is also connected to an active element 1530 embedded within the concrete such as a metal element embedded within a coating such as Ag in AgCl or Ir in IrOx.

Within second image 1500B an embedded sensor 1540 exploiting the concept depicted in first image 1500A is depicted which performs the measurements of measurement device 1510, reference electrode 1520, and active element 1530 but within a self-contained sensor, the embedded sensor 1540. As depicted the embedded sensor 1540 contains a data logger, a reference electrode, a chloride-sensitive coated metal (e.g. Ag with AgCl coating), a battery, and a Bluetooth transceiver which allows data to be transferred from the embedded sensor 1540 to a device 1560. Other elements, not depicted in third image 1500B, may form part of the embedded sensor 1560.

The corrosion rate of reinforcing steel in concrete can be determined using the linear polarization resistance method. In this method, the electrode potential associated with the reinforcing steel in concrete is perturbed through the application of a polarizing current. The change in potential along with the polarizing current can be used to determine the polarization resistance; which can be used to find the corrosion rate. In this method, an embedded system that consists of a device connected to the reinforcement, which generates a polarizing galvanostatic pulse, as well as a reference electrode connected to the reinforcement that records the change in potential following the application of the polarizing pulse are used. Such a measurement is done periodically in an unmanned manner. The change in potential along with the applied current can be analyzed periodically in order to determine the reinforcement corrosion rate.

Figure 15B:
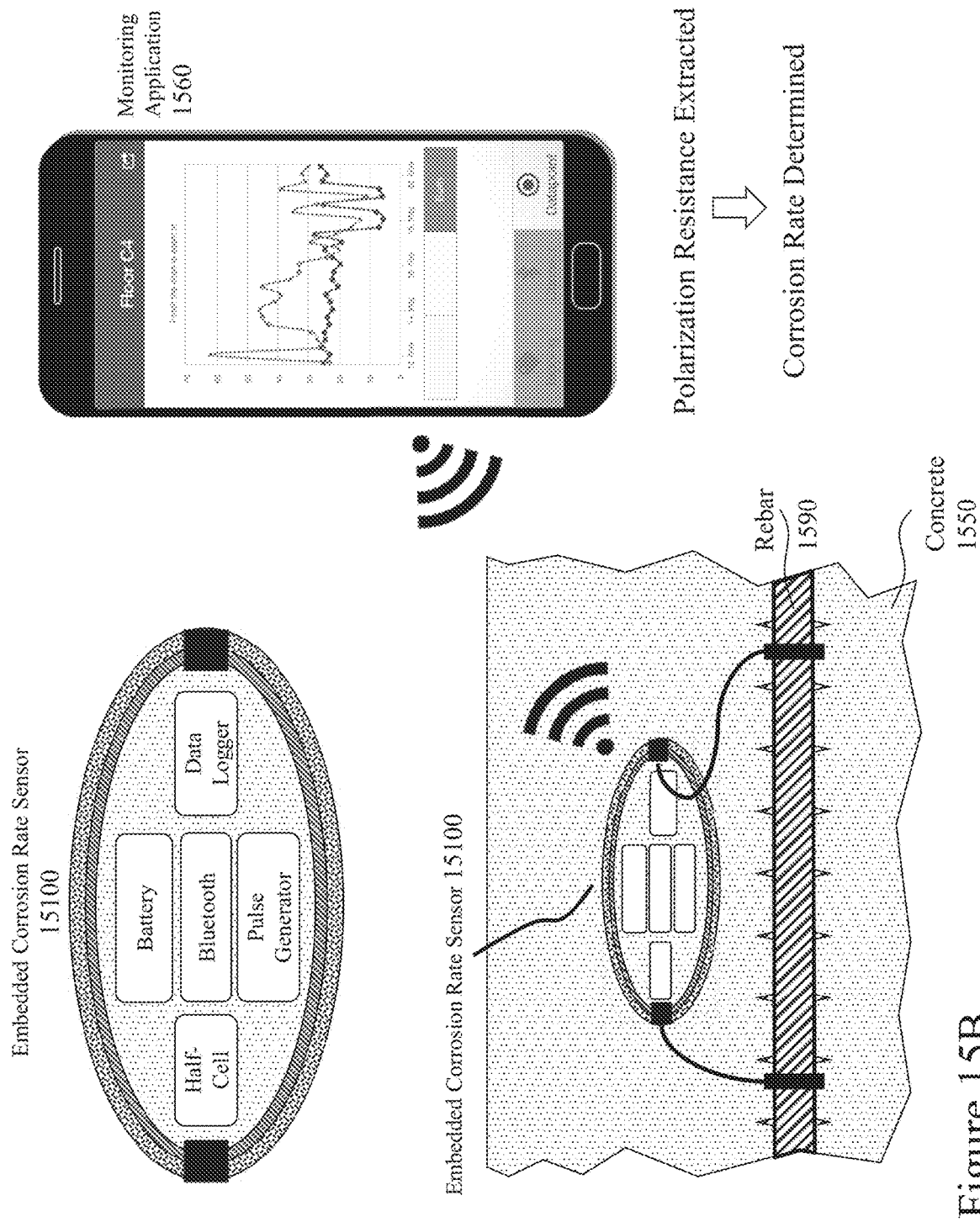
FIG. 15B depicts an exemplary embedded sensor configuration for establishing rebar corrosion rate from polarization resistance.

Accordingly, referring to FIG. 15B there is depicted an embedded sensor 15100 for performing such measurements. The results may be internally processed to generate polarization resistance and therein an estimation of corrosion and/or corrosion rate or externally processed. In either instance the data from the sensor 15100 may be wirelessly transmitted to a scanning device 1560 which acquires the data and may process it directly and then send to remote storage or send to remote storage and acquire back the determined result(s). As depicted the sensor 15100 comprises a battery, wireless interface (e.g. Bluetooth), a half-cell, a data logger and a pulse generator. Other elements of the sensor 15100 may be employed but are omitted for clarity. The sensor 15100 is attached to the rebar 1590 within the concrete 1550 allowing the pulsed measurements to establish polarization resistance to be made once the rebar is embedded in the concrete during the lifetime of the sensor 15100 or concrete infrastructure.

Integration of Sensor Data in Building Information Modelling

The automated acquisition and establishment of location of SMAKs as described above allows for the integration of this location data and the subsequent characteristics of the construction material(s) within a building information model (BIM) which can be used to facilitate the integration between different parties (e.g. owner, architect and engineer among others) and to facilitate the design, construction planning and management of the infrastructure. Adding to the technology integration services, the collection of live data of fresh, hardening and cured concrete using SMAKs allows for the live visualization of data within the BIM through PEDs and/or FEDs both at the work site and remotely. During the construction phase, the aim is to unify the information on fresh concrete properties, continuous in-place strength, temperature, relative humidity, moisture content and occurrence of defects within a structural element which will facilitate the management of the infrastructure during completion of the structure. The BIM may also integrate additional data such as actual strength versus target (design) strength, weather data, etc. Accordingly, user benefits would be seen in the optimization of scheduling, better quality control during the completion phase, easier communication between parties, quick assessment of critical situation as well as easy data-management.

Within the description above one or more SMAKs are embedded within concrete or another construction material which is subsequently deployed at a work site. For example, SMAKs added to concrete prior to transportation, during pouring etc. end up within the concrete without control of its position. Likewise, SMAKs embedded within other materials at manufacture such as plasterboard, fiberboard, etc. are deployed at a worksite without specific knowledge of the SMAKs location. Accordingly, these scenarios result in the challenge of properly identifying the location of the SMAK. If the sensor is attached, for example to a rebar, then the sensor location can be defined through manual techniques such as giving it a proper name, taking pictures, adding comments or manually identifying the location on blueprint. However, even in these instances as well as those where the location of the SMAK(s) is uncontrolled then it would be beneficial to provide a means of automatically identifying and locating the SMAK(s) and embedded sensor(s) within a project or a structure. One such methodology is geographical identification (geotagging) such as described above in respect of FIGS. 4A to 4C wherein a sensor(s) location can be defined through the use of a combination of techniques including, but not limited to, radio-frequency identification (RFID), near field communications (NFC), and beacons.

Accordingly, the location of a sensor or sensors can be automatically established and subsequently visualized through a two-dimensional (2D) or three-dimensional (3D) model. For example, a SMAK may exploit beacons to establish its location relative to the beacons which are then referenced to a global position through one or more global navigation system devices associated with the one or more beacons. Accordingly, the SMAK may establish its location which is subsequently stored and transmitted to a scanning device when interrogated by the scanning device. Accordingly, these beacons may be deployed during the initial pour of the concrete or deployment of the construction material and then subsequently removed as the construction moves to another location.

Accordingly, mapped SMAK data relative to different structures may be established. However, rather than an operator establishing a plurality of measurements across a concrete surface with a physical test system that automatically determines its location relative to a set of beacons and a GPS location the SMAKs have automatically acquired or continue to automatically acquire their location and transmit this together with the measurement data either once at initial reading or with every reading. In this manner, a user need only exploit a scanning device to acquire the SMAK data wherein it is automatically uploaded to the remote storage, processed within a BIM tool, and then available to parties associated with the project to access and review. Where the location data is acquired on initial read this may be in association with a unique identifier of the SMAK such that this data is stored within the remote databases and subsequent reads of the SMAKs establish data and unique identity so that the association of SMAK to location is established through the initial stored data.

Figure 16:
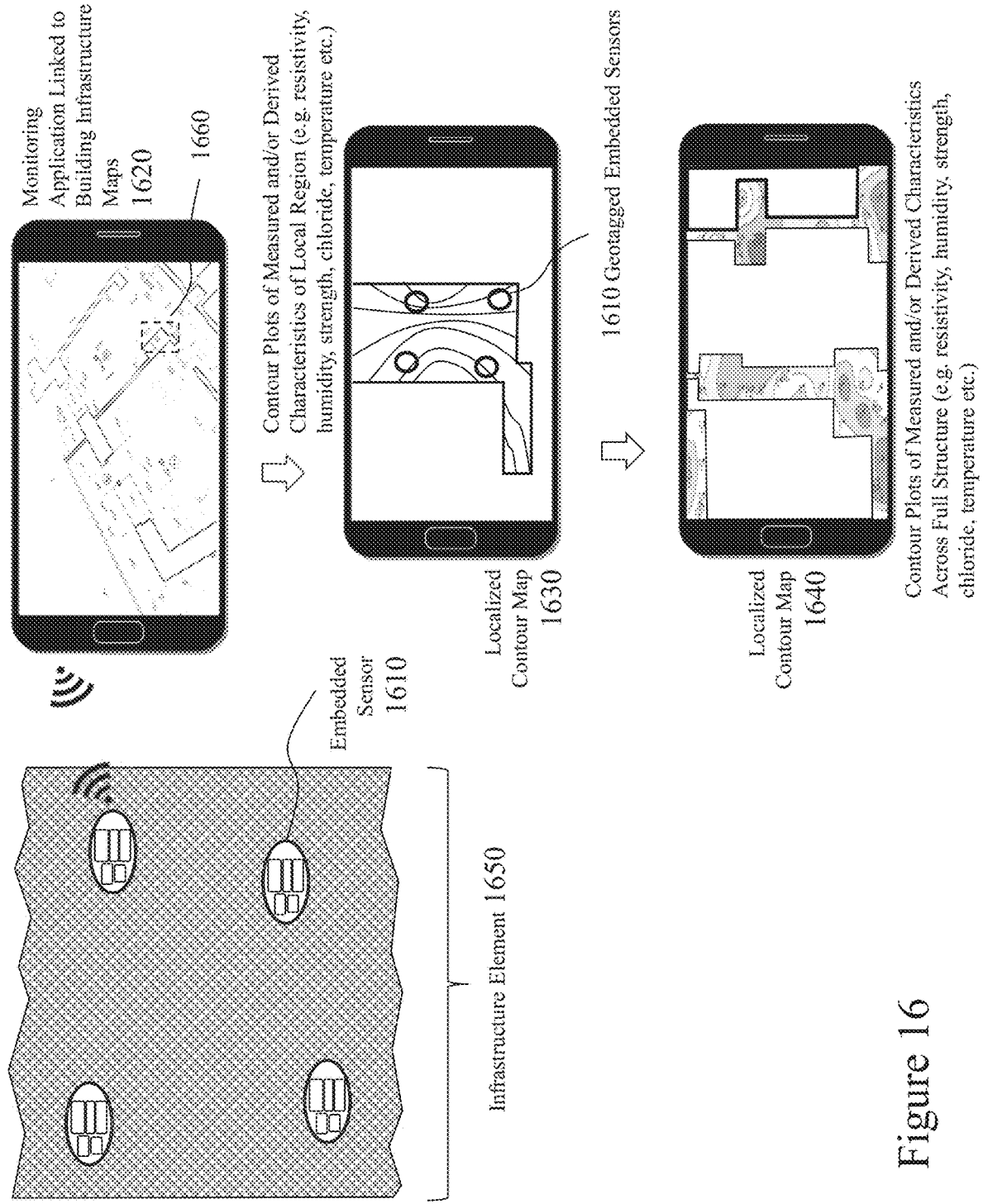
FIG. 16 depicts an exemplary schematic wherein embedded sensor data is integrated within a building information management (BIM) system according to an embodiment of the invention.

Such an exemplary process is depicted schematically in FIG. 16 wherein an infrastructure element 1650 is depicted wherein a plurality of embedded sensors 1610 are deployed within it as discussed above. Further, as discussed above the information acquired, stored, and/or generated by the embedded sensors 1610 is transferred to a scanning device and therein can be processed upon the scanning device and/or uploaded to a remote server wherein it may be processed and then downloaded to the scanning device. Accordingly, referring to second image 1620 an application associated with the embedded sensors 1650 may be linked to a BIM such that a region 1660 within the BIM may be selected and its data presented such as depicted in third image 1630 wherein a contour plot of the region 1660 is depicted together with the locations of the embedded sensors 1610 which are obtained through geotagging/geolocation such as described supra. Accordingly, as depicted in fourth image 1640 the user can adjust the portion of the infrastructure depicted, such as full structure, as well as the format of the depicted data. Accordingly, the user may elect to depict contour plots of measured and/or derived characteristics including, but not limited to, resistivity, humidity, predicted strength, chloride ion concentration, temperature etc.

Performance Based Construction Material Selection

Figure 17:
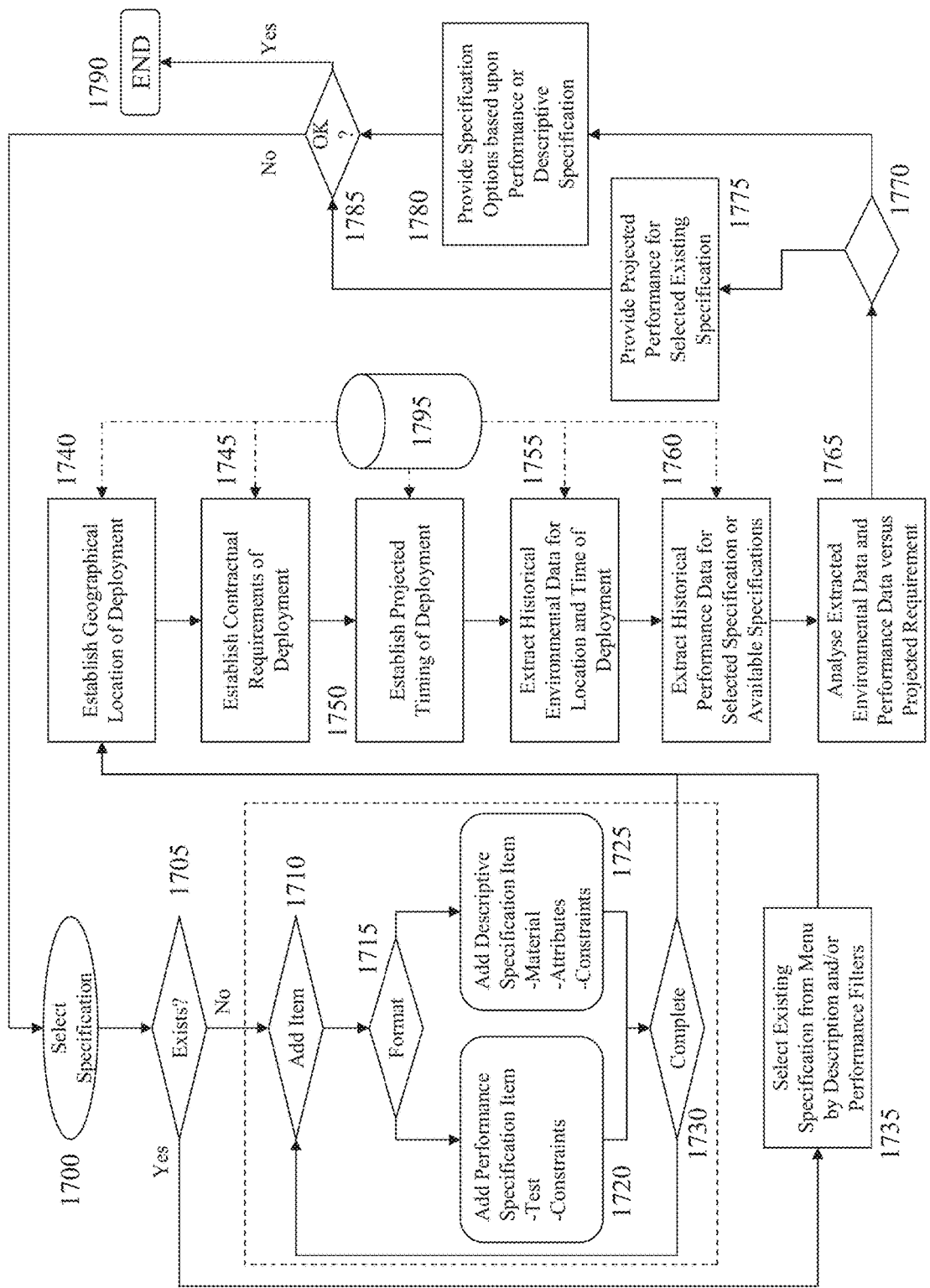
FIG. 17 depicts an exemplary process flow for the verification and/or specification of a construction material manufacturing composition based upon acquired material performance data from previous deployments acquired using sensors according to embodiments of the invention.

Referring to FIG. 17 there is depicted an exemplary process flow for the establishment of a manufacturing specification in respect of a construction material, such as concrete for example, exploiting acquired performance data from SMAKs and/or other performance monitoring sensors. Accordingly, the process as depicted comprises steps 1700 to 1790 in conjunction with a database 1795.

Step 1700 wherein the user initiates the process for selecting a material specification.

Step 1705 wherein a determination is made as to whether the specification already exists or not, wherein if the specification exists the process proceeds to step 1735 otherwise it proceeds to step 1710.

Steps 1710 to 1730 wherein the process of construction of a particular material specification containing a number of items is presented. Upon addition of an item through steps 1710 to 1725 the process determines in step 1710 whether the specification is complete or not and proceeds to step 1740 upon completion or step 1710 if not. Within some embodiments of the invention the determination of whether the completion has occurred is based upon selecting a number of items until a total number items desired is achieved. Optionally, the determination is made by the user or through a combination of the process and user. For example, the user may be guided to choose a base material (e.g. type of cement), a number of additives in predetermined classes of additive (e.g. aggregate, admixture, etc.) wherein selection of at least one in each as the process moves sequentially from one to another class would mean completion of the specification. Accordingly, the process will loop until the appropriate number of specification items are defined and/or the user denotes completion.

An initial decision is made in step 1715 as to whether the specification item to be created will be descriptively based or performance based. A descriptive specification item may reference a specific material or materials and the materials attributes and/or constraints while a performance-based specification item would be established through the physical and/or chemical characteristics of the construction material either after completion of production or upon installation and thereafter. Accordingly, these are performed in steps 1720 and 1725. In this manner the construction material may be specified in terms of final target performance rather than by specific brand, identity and/or composition. Within this series of steps 1710 to 1730 the user may also establish one or more quantifiable properties and/or standard tests and may include predetermined dependent variables and/or constraints of which the construction material must satisfy. These would typically be provided to the user from a database such as database 1795. Where the specification items are listed descriptively then the item may include the material and its material quantifiable property or properties such as water/cement ratio, a set of material attributes, and/or constraints which the materials should fall within.

Once defined, either descriptively or by performance, the specification item is preferably complete and added to the concrete specification being built. The list of completed specification items may be compared to the total number of items that are to be defined for the current specification and if all of the items have not been completed, the next specification item should be defined. Each additional item can be either descriptive or performance-based again and a concrete specification may therefore contain a mix of both descriptive and performance-based specification items. Once all of the items for a particular concrete specification have been properly defined and constrained the specification is stored.

Step 1735 wherein if the decision in step 1705 was to select an existing specification then the user proceeds to make the selection from a menu using description and/or performance filters, for example.

Step 1740 wherein upon selection of the established specification or completion of the new specification the process establishes the geographical location for the deployment of the construction material. This may, for example, be by user entry or alternatively through association of the construction material specification to a project wherein the data for the project includes this and other information as required including, but not limited to, that in steps 1745 to 1760.

Step 1745 wherein the contractual requirements associated with the deployment are established. These may, for example, be a restriction on how long formwork can be left up after construction material is poured, how much material is required, time limits for delivery and pouring as the location may be within a busy downtown core, an issue from another aspect of the project etc.

Step 1750 wherein projected timing of the project is established such as when formwork will be established, when pouring should be started, when pouring should be complete, etc. are extracted from the database 1795

Step 1755 wherein historical data relating to the location and the projected time of deployment are extracted from the database 1795.

Step 1760 wherein historical performance data for the selected specification or available specifications based upon the performance and/or descriptive specification items is extracted from the database 1795.

Step 1765 wherein the extracted historical data relating to location, time, historical environmental data, historical performance data etc. are processed to establish a projected set of construction material characteristics at one or more predetermined points in time.

Step 1770 wherein the process determines whether the user selected an existing specification and proceeds to step 1775 or provided specification options and proceeds to step 1780.

Step 1775 wherein the user is provided with projected performance of the selected existing specification based upon the location, time, historical environmental data, historical performance data etc.

Step 1780 wherein the user is provided with specification options based upon the target characteristics defined by the performance and/or specification items selected by the user being matched against the available construction material specifications based upon the location, time, historical environmental data, historical performance data etc.

Step 1785 wherein the user determines whether to stop the process wherein the process proceeds to step 1790 or to iterate and the process returns to step 1700. Optionally, in the subsequent iterations the user may be provided with options to adjust the project related data such as whether a deployment is undertaken earlier or later, whether an additive should be employed, etc.

Optionally, the process automatically performs the determination in step 1785 based upon the projected performance meeting the required performance requirements. Optionally, the process may extract the target performance specification items from the database 1795 based upon selection of the project by the user within another process step and therein perform a construction material selection automatically.

Figure 18:
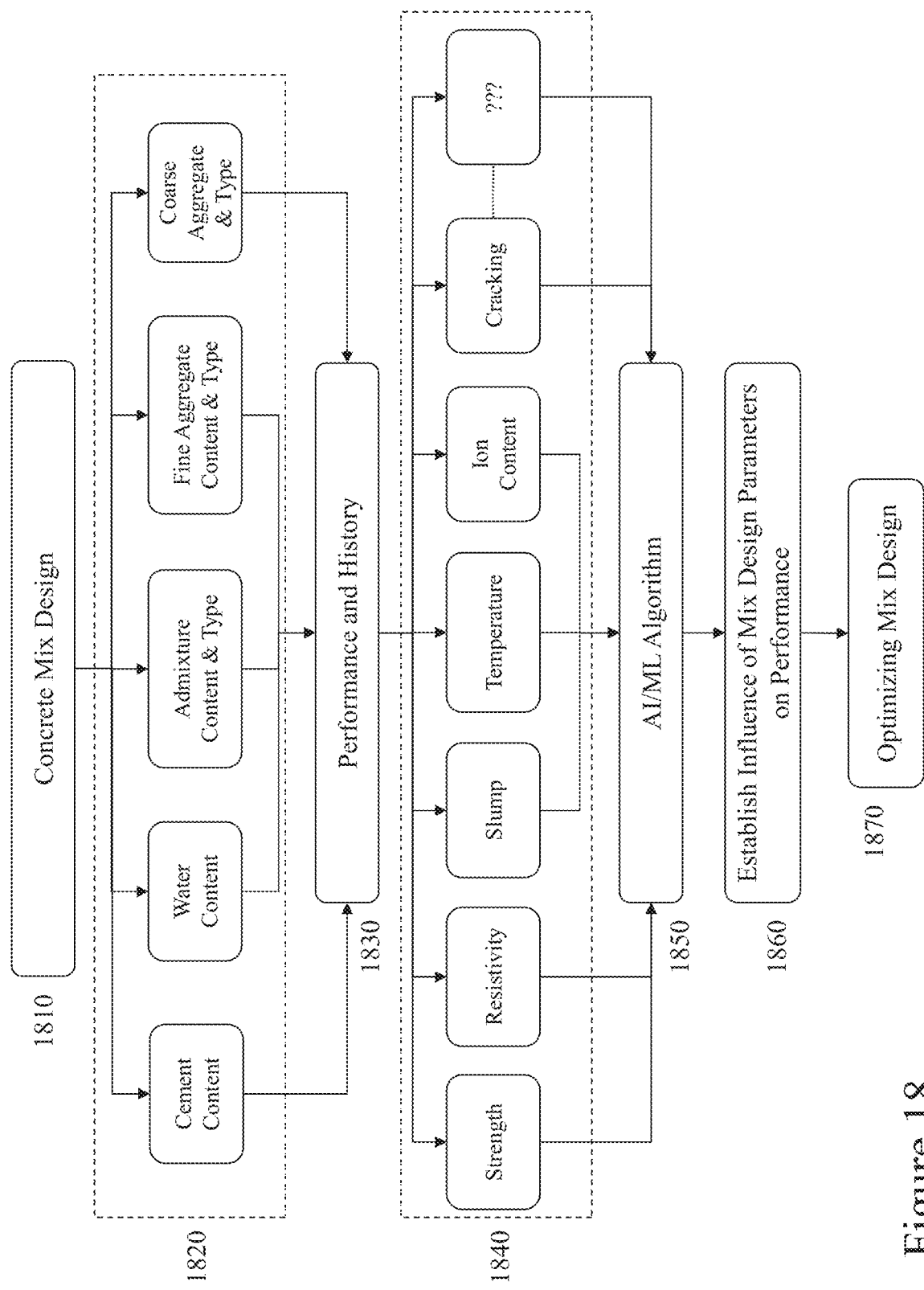
FIG. 18 depicts an exemplary process flow for optimizing a manufacturing specification for a construction material according to an embodiment of the invention exploiting machine learning and artificial intelligence.

It would also be evident that the acquisition of data relating to multiple construction materials, e.g. a concrete mix, also allows for optimization of a concrete mix as a discrete process for a manufacturer as opposed to the determination of a mix design for a specific project as described and depicted in FIG. 18. Such an exemplary process flow is depicted in FIG. 18 for optimizing a manufacturing specification for a construction material according to an embodiment of the invention exploiting machine learning and artificial intelligence comprising first to seventh blocks 1810 to 1870 respectively, these being:

First block 1810 wherein a user can select a concrete mix design;

Second block 1820 wherein the concrete mix elements are established such as cement content, water content, admixture content and type, fine aggregate content and type, and coarse aggregate content and type;

Third block 1830; wherein the performance data and history for the selected mix are extracted from the stored data within the remote servers which can comprise the data acquired from embedded sensors, partially embedded sensors, third party sources such as environmental data etc., as well as data established at the time of concrete mix production and transportation;

Fourth block 1840 wherein the extracted performance data and history are analysed to extract different properties of the concrete such as strength, resistivity, slump, temperature, ion content, cracking etc.

Fifth block 1850 wherein artificial intelligence (AI)/machine learning (ML) algorithms and/or processes are employed to process the extracted data;

Sixth block 1860 wherein the analysis performed by the AI/ML algorithms is assessed to establish the influence of mix design parameters on the performance of the concrete mix as variations in mix preparation, mix transportation, deployment, life cycle etc. can be determined and/or evaluated; and Seventh block 1870 wherein amendments to the concrete mix can be determined to optimize the mix such as for improved long term strength, reduced chloride ions, reduced time before formwork removal, reduced impact of ambient environment etc.

The process described and depicted in respect of FIG. 18 may be fully automated or it may require user input such as identification of which aspects of performance of the mix are to be assessed/optimized. Further, the analysis may be filtered such as for geographic location, season, type of infrastructure element, etc.

Figure 19:
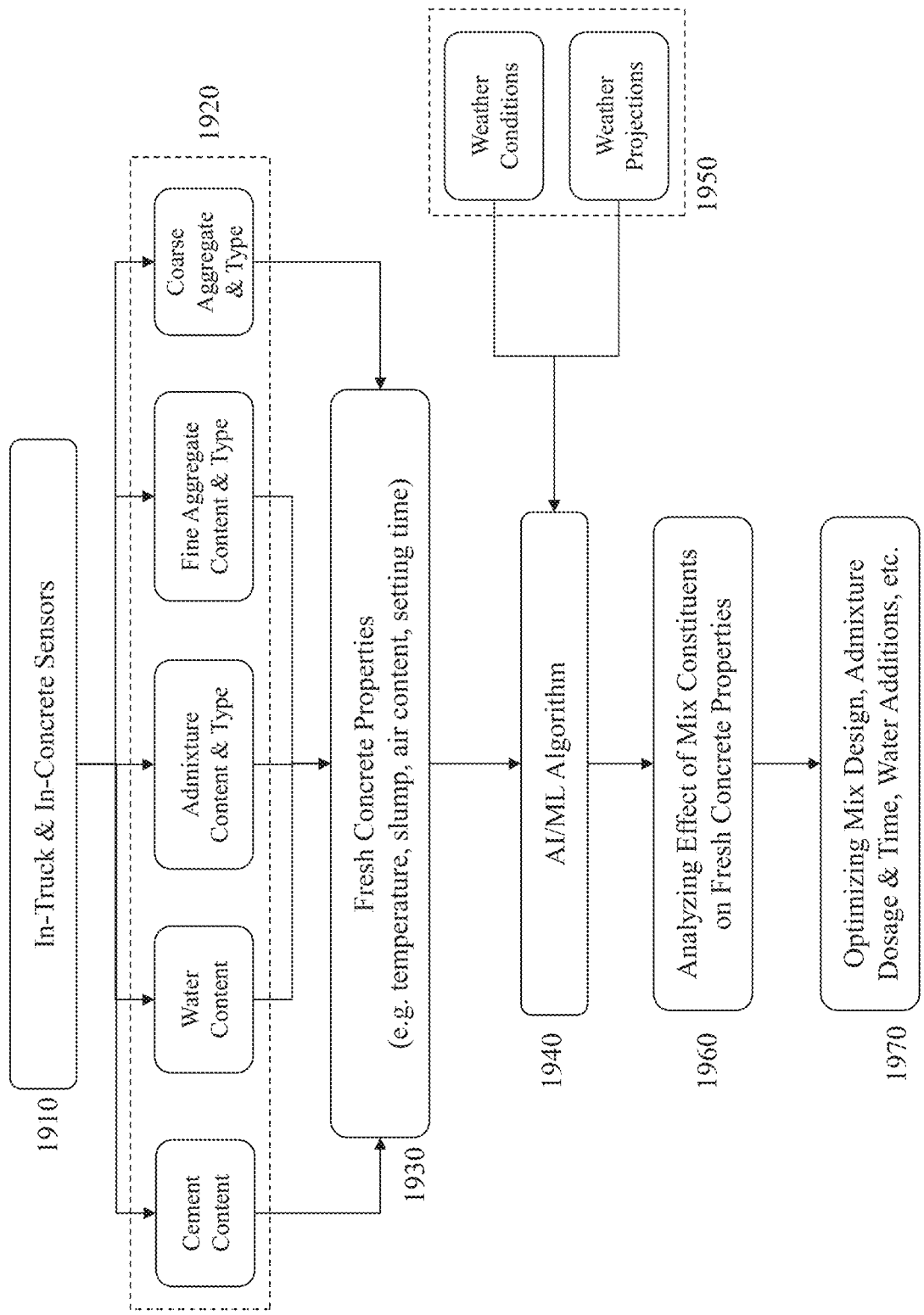
FIG. 19 depicts an exemplary process flow for optimizing a construction material during transportation according to an embodiment of the invention exploiting machine learning and artificial intelligence.

Optionally, a variant process may be implemented such as depicted in FIG. 19 wherein analysis is performed in respect of transportation of the construction material, e.g. concrete mix. In many concrete mix designs and deployments one or more admixtures are added to the concrete. These may be added at various points including, but not limited to, concrete batching, in truck, during deployment, and after deployment. Accordingly, FIG. 19 depicts an exemplary process for assessing admixtures, water etc. both in terms of which to add to the construction material based upon acquired historical data relating to their addition, delivery, performance etc. also determine when to add a particular admixture to a construction material batch and the quantity to add. For example, the analysis may determine that an admixture improving the low temperature pouring characteristics and initial curing of concrete is best added thirty minutes prior to pouring. Further, as this may be problematic for some or all deliveries the admixture(s) may be preloaded into one or more dispensers which are automatically triggered based upon downloading of a program to the concrete truck from the database for a specific delivery batch. In this manner, the admixture(s) are automatically added rather than when the truck driver can stop and add them. Equally, such analysis may determine that a batch having been loaded for two hours reaches a point where subsequent deployment will result in reduced performance or that the current projected environmental conditions will require all loads to be poured within a predetermined period of time if the concrete is required as a single contiguous block rather than multiple layers as a second pour is made upon a curing previous pour etc.

Accordingly, the exemplary process flow comprises first to seventh blocks 1910 to 1970 respectively, these being:

First block 1910 wherein data acquired from in-truck and in-concrete sensors such as described above is collected and stored within the one or more remote servers storing information relating to the sensors as well as that established from concrete batch manufacturing plants, sensors embedded within the infrastructure elements, semi-embedded sensors associate with infrastructure elements, etc.;

Second block 1920 wherein data relating to the mix transported for which data exists at the various points such as batching, truck loading, pouring, curing, ongoing life cycle monitoring etc. are retrieved and associated with the in-truck and in-concrete sensor data;

Third block 1930 wherein the fresh concrete properties such as temperature, slump, air content, setting time etc. are retrieved and associated with the data existing at the various points such as batching, truck loading, pouring, curing, ongoing life cycle monitoring etc. are retrieved and associated with the in-truck and in-concrete sensor data;

Fourth block 1940 wherein a plurality of artificial intelligence (AI)/machine learning (ML) algorithms and/or processes are employed upon the data in conjunction with data from other sources such as weather conditions and weather projections extracted from fifth block 1950;

Sixth block 1960 wherein the analysed effects of the mix constituents on the fresh concrete properties are established against the fresh concrete properties; and Seventh block 1970 wherein optimizations of the mix design, admixture dosage and time, water additions etc. are established.

Figure 20:
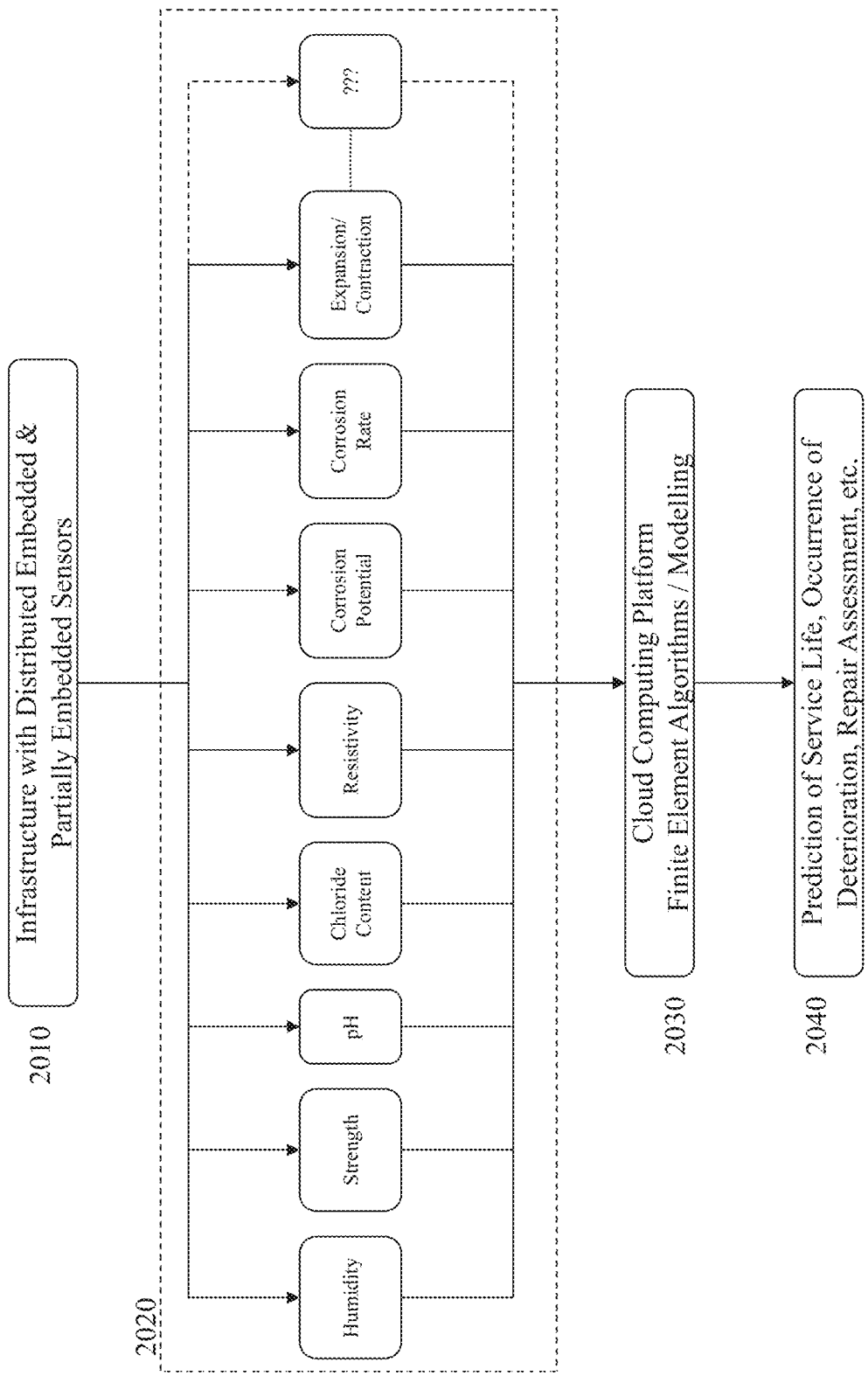
FIG. 20 depicts an exemplary process flow for service life assessment for an infrastructure element exploiting monitored installations of its construction material according to an embodiment of the invention exploiting machine learning and artificial intelligence.
Figure 21:
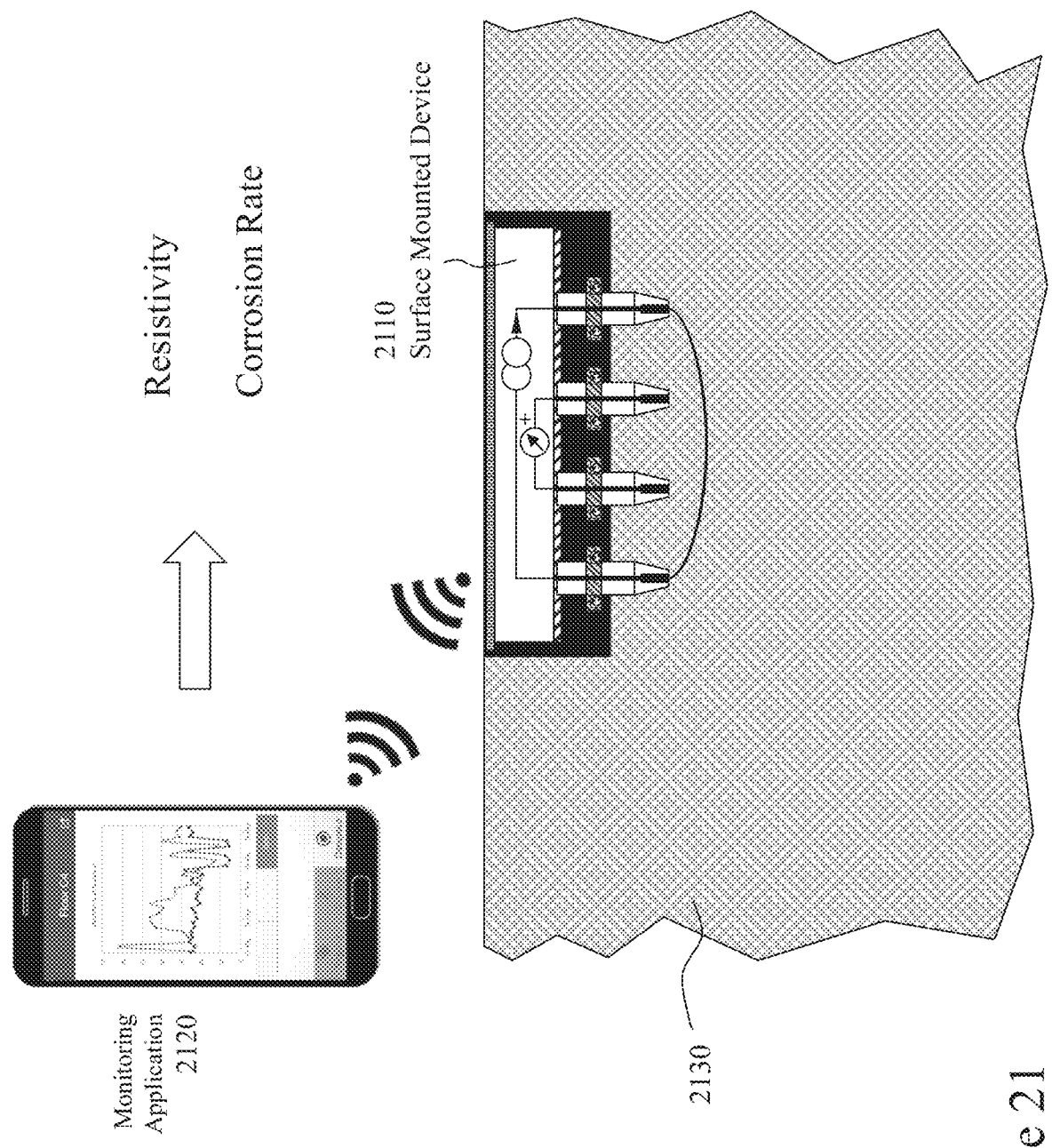
FIG. 21 depicts contactless electrical characterization of corrosion and rebar presence within concrete according to an embodiment of the invention with a partially embedded sensor.

Each of the exemplary processes described and depicted above exploits the acquisition of data from embedded sensors within the infrastructure. As depicted in FIG. 20 an item of infrastructure has a plurality of embedded and non-embedded sensors associated with it as indicated in first block 2010. These measurements as indicated in second block 2020 may include, but are not limited to, humidity, strength, pH, chloride content, resistivity, corrosion potential, corrosion rate, and expansion/contraction. This data is then embedded to a cloud computing platform exploiting finite element algorithms and finite element modelling in third block 2030 wherein in fourth block 2040 the cloud computing platform generates data relating to prediction of service life, occurrence of deterioration, repair assessment etc.

Artificial Intelligence/Machine Learning in Material and/or Plant Performance: It would be evident that a process such as depicted in FIG. 18 may exploit artificial intelligence and/or machine learning in order to establish projected material performance. Optionally, historical performance data of construction material specifications may be employed to assess plant performance in manufacturing the construction material(s). Such analysis may result in adjustments to construction material manufacturing processes and/or compositions (recipes) at one or more plants in dependence upon analysis across all plants. Such a process within FIG. 18 together with variants and/or options described can aid producers, engineers, designers, etc. Ready mixed concrete producers, for example, can have hundreds or thousands of concrete mixes (recipes or designs) which are delivered to different projects with various specifications including target strength, workability, durability, air content etc. These mixes are subjected to quality assurance (QA) and quality control (QC) through which various data on concrete properties which may be collected with SMAKs from initial manufacture to delivery and on into the life of the structure built. Accordingly, the ability to assess historical data helps ready mix producers select the most appropriate mix from their database based on the specifications requested by the customer for the location, time, etc. AI algorithms and processes including machine learning can be utilized to analyze this massive database and help the ready mix producer select the most suitable and/or economical mix that meets the required specifications.

In addition, combining SMAKs with truck-mounted sensors and/or sensors attached to the formwork etc. can be used to collect more data during the delivery process. After delivery, the SMAKs can be used to collect additional data not only during the setting, curing and hardening stages but also during the subsequent life of the structure. Through a global Internet of Things (IoT) platform all this data can be used to extend the capabilities of the Artificial Intelligence algorithms as developed above and add predictive features to the sensors and software applications exploiting these sensors and the data acquired. Such an IoT platform can also help with more accurate and real-time optimization of the concrete mix at the batching plant for an ongoing project as well as delivery etc.

ARTIFICIAL INTELLIGENCE/MACHINE LEARNING FOR ALARMS AND ALERTS ON WORK SITES: The concepts described above in respect of acquiring ongoing data relating to a construction material such as concrete, for example, both prior to deployment and subsequent to deployment can be exploited in conjunction with one or more software applications in execution upon a remote server, PEDs and/or FEDs to exploit AI/ML algorithms knowing the historical trends and performance for that concrete mix, historical and forecasted ambient conditions, and data on the practice of the construction company for accurate prediction of the concrete properties forward in time. The SMAKs and other sensors associated with the work site together with third party information sources such as weather predictions over next few hours, day, several days etc. can be used to actively monitor and project the material characteristics and provide alerts, alarms, and suggestions during the construction of a structure to improve the final properties of the concrete. The sensors can continue collecting data during the service life of the structure and the AI algorithms can monitor this data to predict the performance of concrete structures and assist with the repair and maintenance schedules.

ARTIFICIAL INTELLIGENCE/MACHINE LEARNING FOR DELIVERY VEHICLES: Next generation of concrete trucks may be equipped with onboard systems to adjust the mixture by adding water and chemical admixtures such as accelerators, air entertainers, plasticizers, etc. that control concrete properties. As discussed above the data collected from the embedded and truck-mounted sensors can be used in conjunction with the variable data from ambient conditions, GPS location of the truck, traffic data, etc. to control and monitor automatically the amount and timing of the addition of water and chemical admixtures to ensure that the final concrete at the delivery time meets the required specifications set by the customer, engineers, designer etc. Further, as noted supra additional material characteristics such as slump can be automatically determined during delivery such that determinations such as whether to reject a load on the basis of slump (workability), air content etc. can not only be made automatically but also earlier so that a replacement load can be established. Further, automatically adding said water and/or admixtures allows for automatic updating of batch related data avoiding issues relating to human error either in which admixture was actually added, the quantity added, when and how much water was added etc.

REAL TIME CONDITION ASSESSMENT AND/OR SERVICE LIFE PREDICTION: The ongoing determination of pH, chloride content at given depths, reinforcement corrosion potential, reinforcement corrosion rate, occurrence of cracking, among other collected attributes, allows an enhanced prediction of the concrete service-life in a real-time manner. Such data may be collected within a cloud based platform and analyzed using numerical algorithms, machine learning and artificial intelligence in order to predict several service-life attributes using the collected data. For example, a knowledge of the chloride content or relative humidity at several given depths allows for determination of the future point in time at which the chlorides will reach the reinforcement bar (rebar) surface in the concentrations required to initiate corrosion. Such data can also corroborate the existing knowledge base and expand on the current service-life prediction methods.

CONTINUITY OF DATA: At present only parts of the overall product, transport, deployment and life cycle of a construction material such as concrete are established. The exploitation of SMAKs according to embodiments of the invention allows for enhanced data acquisition and analytics at all points in the cycle from initial concrete batching, transportation, pouring and placing stages. Periodic acquisition of data from the SMAKs during this cycle can be stored within cloud based databases wherein remotely stored or locally stored applications may access and exploit this data in order to provide real time and forward projecting performance analysis. Accordingly, the concrete properties may be monitored within the delivery vehicle, e.g. concrete truck, using truck-mounted sensors/units and this data transferred together with additional data such as GPS location, local temperature, humidity, etc. to the cloud to complete the data history of the embedded sensor within the truck. With appropriate "tagging" of the batch to the SMAKs loaded into the batch to the truck etc. than a full history can be established.

Connectionless Electrical Pulse Response Analysis

CONCEPT: Within the description above in respect of embodiments of the invention devices such as an embedded 4-point probe device, embedded SMAKs, and devices configured for surface mounting via one or more fittings have been described. These sensor/measurement devices allowing automatic acquisition of measurements. Within embodiments of the invention, for example, surface mounted devices may be attached and employed in locations that subsequently become inaccessible through subsequent aspects of the structures building and completion or remove the requirement for users to return periodically and perform the measurements. Accordingly, sensors according to embodiments of the invention may exploit techniques described within this specification as well as others such as described by the inventors within WO 2015/172,231 entitled "Electrical Methods and Systems for Concrete Testing."

Figure 22:
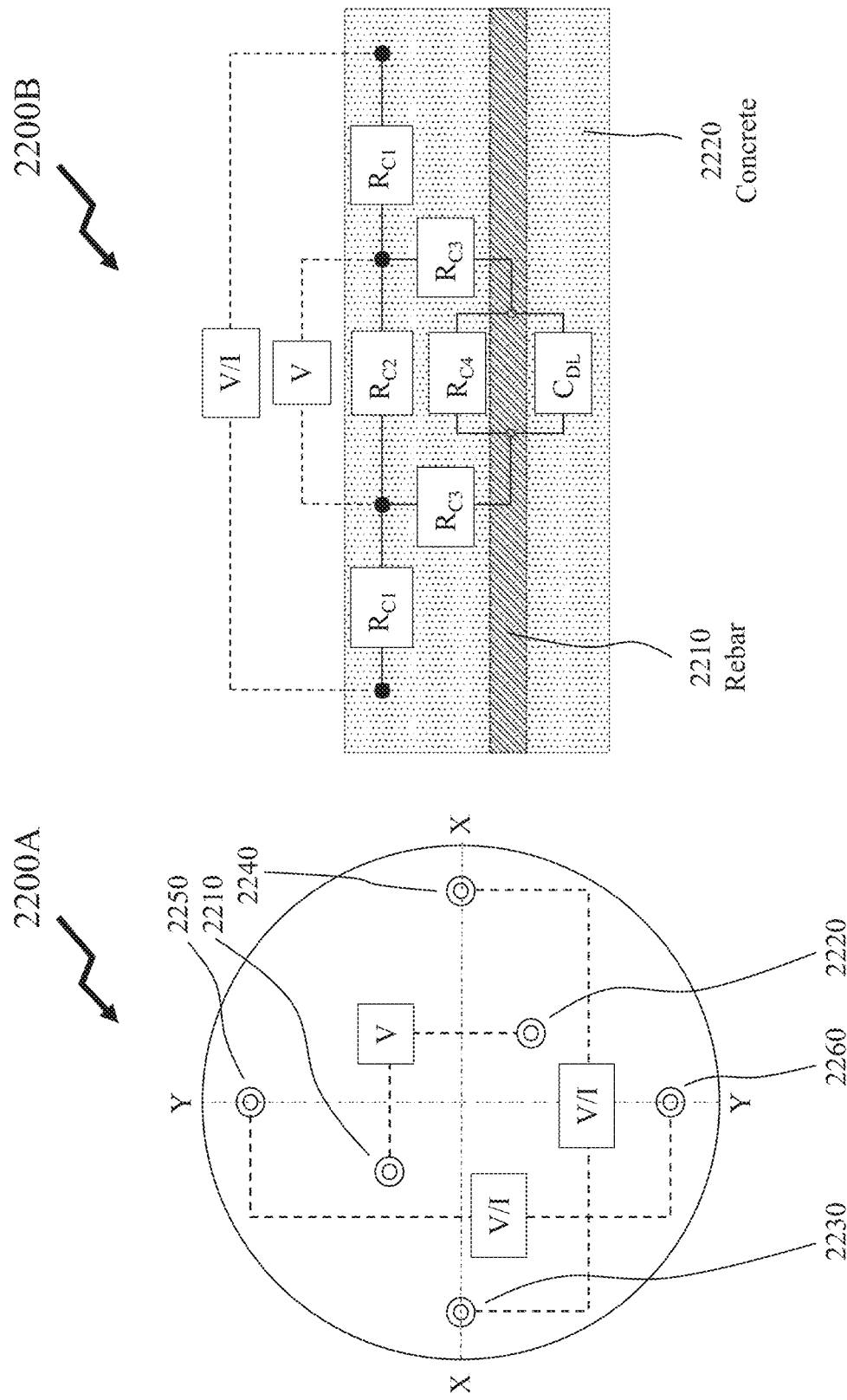
FIG. 22 depicts a 6-point probe configuration according to an embodiment of the invention and an equivalent circuit employed by the users within a Connectionless Electrical Pulse Response Analysis (CEPRA) technique according to an embodiment of the invention.

One such technique being the determination of rebar corrosion in a connectionless manner via a four-point (4P) probe or a 6-point (6P) probe which extends the measurement to two mutually perpendicular axes, such as depicted schematically in FIG. 22 in first image 2200A. In this technique, the potential difference between the two inner probes is monitored following the application of a narrow DC current pulse applied from the outer probes for a short period of time. Analyzing the recorded response yields conclusions regarding the reinforcement corrosion rate as well as the concrete resistivity. Accordingly, a sensor may periodically perform measurements in order to obtain the corrosion state and concrete resistivity. Alternatively, the 4P/6P probe may perform a pulse based analysis in combination with a swept frequency characterization. The 6P probe depicted in first image 2200A in FIG. 22 consists of first and second probes 2210 and 2220 respectively which apply a DC voltage, AC voltage, or voltage pulse according to the measurement being performed. A first set of measurement probes comprising third and fourth probes 2230 and 2240 respectively provide measurement data in response to the applied electrical signal in a first direction, labelled X, which is at 45° to the axis of the first and second probes 2210 and 2220 respectively. A first set of measurement probes comprising fifth and sixth probes 2250 and 2260 respectively provide measurement data in response to the applied electrical signal in a second direction, labelled Y, which is at −45° to the axis of the first and second probes 2210 and 2220 respectively an orthogonal to the first axis.

Accordingly, the inventors have extended these concepts to provide a Connectionless Electrical Pulse Response Analysis (CEPRA) technique and devices exploiting it. Within typical DC measurements of the polarization resistance, the steel-concrete system is represented, simplistically using Randles circuit. If an AC current, at a wide range of frequencies, is applied to this circuit and the potential response is monitored, then the circuit components can be analyzed by observing the changes in real impedance, imaginary impedance, and phase shifts. In the case of the Randles circuit, in the very high frequency range, the impedance caused by the double-layer capacitance tends to reach negligible values, and this double layer acts as a short-circuiting element, leading to most of the current flowing through the electrolyte/concrete resistance and the short circuit caused by the double-layer capacitance. Therefore, at the very high-frequency ranges, the electrolyte/concrete resistance can be measured directly as the impedance modulus. At the very low-frequency ranges, the impedance caused by the double-layer capacitance tends to reach very high values, leading to most of the current flowing through the electrolyte/concrete resistance and the polarization resistance. Therefore, at the low-frequency range, their summation can be found directly as the impedance modulus.

However, within a connectionless technique according to embodiments of the invention there is a higher system complexity. If a current pulse or a step voltage is applied, for example from the two outer probes of a Wenner probe, this current has two primary flow paths. One path is normal to the metallic electrode, which causes the charging of the double-layer capacitance or the polarization of the electrode (depending on the frequency of the applied current); another path is parallel to the metallic electrode, in which the current applied by one of the probes is consumed by the other. The portion of current flowing in each of these paths is dependent on the applied current's frequency, the concrete cover characteristics (cover depth and resistivity), the polarization resistance value, the rebar diameter, and the double-layer capacitance. These are all interrelated factors that affect the current flow path and the obtained results. This system can be represented schematically using the circuit model shown in second image 2200B which clearly identifies the two major current flow paths within the concrete medium through $R_{C2}$ and $R_{C3}$ for the rebar 2210 within the concrete structure 2220 is depicted.

Within this equivalent circuit:
$R_{C1}$ represents the probes' contact resistance, and all of the current is faced by this resistance;
$R_{C2}$ represents the current flow path between the two probes (the path not polarizing the rebar);
$R_{C3}$ represents the current flow path that polarizes the rebar or charges the double-layer capacitance.

The magnitude of current passing by each of these resistors is dependent on (1) the magnitude of their resistance, (2) the impedance caused by the capacitance or the extent of charging of this capacitance, (3) the magnitude of the polarization resistance, (4) the concrete cover depth and reinforcement diameter, and (5) the frequency of the applied current. This circuit can be solved in order to determine the polarization resistance (Rc4 in second image 2200B in FIG. 22) if the current applied from the two outer probes is swept from very high to very low frequencies. However, this is a very time consuming measurement that may take several minutes to a few hours depending on the circuit's time constant. Alternatively, the components of this system can be retrieved if the response (i.e., voltage difference between the two inner probes) to a narrow DC/AC current or voltage pulse applied from the outer probes for a short period of time is fitted to the theoretical transient obtained from this circuit. In these cases, the measured voltage response as a factor of time is similar to that of a charging RC circuit, as shown in Equation (2), assuming that the electrolyte/concrete capacitance is negligible, where $V_{ex}$ is the constant voltage applied through the external electrodes and $V_{in}$ is the potential difference measured between the two inner electrodes. This assumption is the same as that employed in all of the other monitoring techniques.

$$V_{in}(t)=V_{ex}(A-Be^{-Dt}) \quad (2)$$

$$A=f(R_{C1},R_{C2},R_{C3},R_{C4}) \quad (3)$$

$$B=g(R_{C1},R_{C2},R_{C3},R_{C4}) \quad (4)$$

$$D=h(R_{C1},R_{C2},R_{C3},R_{C4},C_{DL}) \quad (5)$$

The circuit model depicted in second image 2200B in FIG. 22 can be solved for the variables A, B, and D. Accordingly, the inventors have established that these variables follow functions as given by Equations (3) to (5) respectively. By measuring the voltage response over time, A, B, and D can be calculated by fitting Equation (2) to the measured data. These factors can then be used to calculate the circuit components shown in the equivalent circuit in second image 2200B in FIG. 22. This solution approach is rather complicated compared to the other circuits employed within the prior art. However, such a circuit can be solved using more complicated solution procedures if the cover depth is known. This is because the cover depth provides an indirect measure of the ratio of current flowing through $R_{C2}$ to that flowing through $R_{C3}$.

Figure 23:
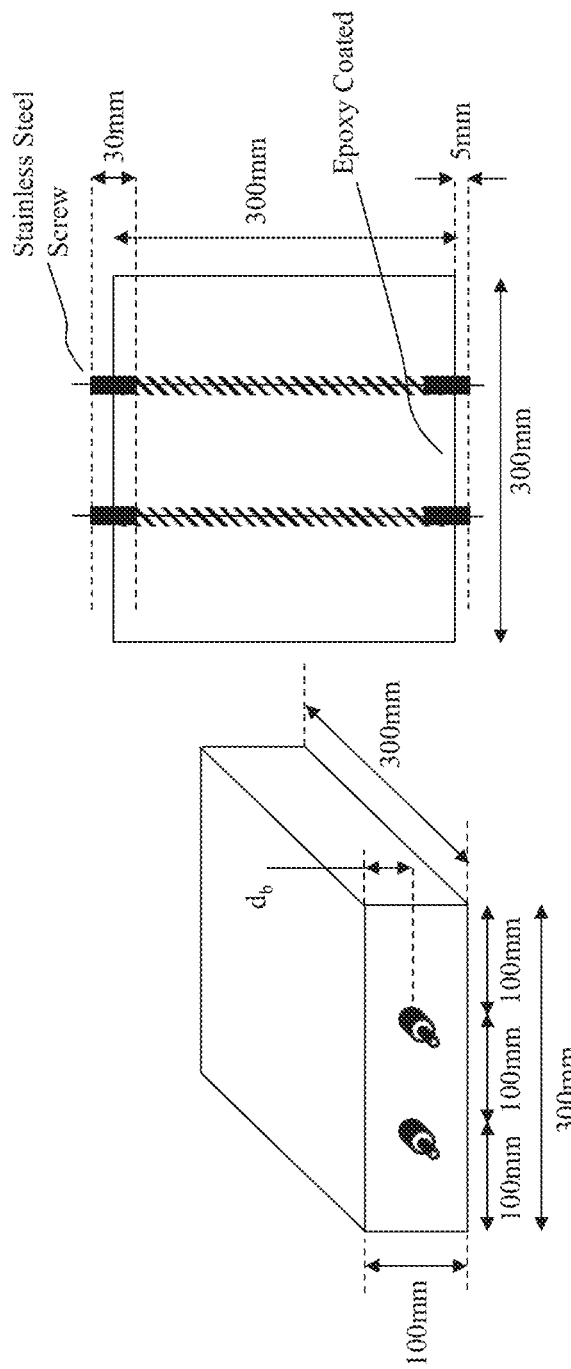
FIG. 23 depicts schematic representations of test blocks employed in verifying the CEPRA technique.

EXPERIMENTAL METHODS: A total of 16 reinforced concrete test blocks were cast to perform experimental measurements upon. These are depicted schematically in FIG. 23 wherein each block cast was 300 mm (L) by 300 mm (W) by 100 mm (H) (12"×12"×4") with each being reinforced with two black steel reinforcements at the same cover depth. The concrete mix for the blocks being listed in Table 1. The mixture was selected in order to obtain relatively high corrosion activity on the reinforcements in a short time due to the higher permeability and lower resistivity of this concrete. Four different dosages of admixed chlorides were used in the experimental tests in order to provide a wide range of activity and concrete resistivity. The admixed chloride dosages employed were 0%, 1.5%, 3% and 6% by weight of cement. For each of the admixed chloride percentages, four blocks were cast with the mix design given in Table 1. For each admixed chloride percentage three of the test blocks had the two reinforcements disposed at either 20 mm (0.8"), 40 mm (1.6"), or 70 mm (2.8") cover depth in which 10M rebar was employed (nominal diameter 11.3 mm (0.45")). For the fourth block with each admixed chloride percentage a 20M rebar (nominal diameter 19.5 mm (0.8")) was used with 40 mm (1.6") cover depth to study the effect of reinforcement area on the results.

TABLE 1

Mixture Design for Laboratory Test Blocks

| Constituent | Amount (kg/m³) | Amount (lb/ft³) |
|---|---|---|
| GU Cement | 265 | 16.6 |
| Coarse Aggregate (<19 mm (0.8")) | 1,055 | 66.0 |
| Fine Aggregate | 940 | 58.7 |
| Water | 165 | 10.3 |

Accordingly, 32 reinforcements were prepared for this study for the 16 blocks outlined. The end 3 cm (1.2") of the reinforcements were epoxy coated to prevent atmospheric corrosion and contamination from the to the atmosphere at the part of the reinforcement protruding from the concrete. The reinforcements were sandblasted to remove any prior corrosion by-products or mill scale. Finally, all of the reinforcements were weighed, and the weight recorded to the nearest 0.01 g (0.00035 oz).

Four molds were prepared allowing for the three blocks with the different cover depths and the block with 20M reinforcement to be cast at once with the same concrete mixture. The concrete was cast in accordance with ASTM C192 "Standard Practice for Making and Curing Concrete Test Specimens in the Laboratory." Casting was undertaken in two layers, with each layer tamped 30 times. The surface was finished using a steel trowel, and the specimens were covered with wet burlap and wrapped in plastic for 24 hours. The specimens were then removed from the formwork after 1 day and placed into a container with an approximately 3 cm (1.2") deep layer of water to ensure the availability of the required moisture for corrosion propagation. Weekly corrosion rate measurements were taken on all of the slabs using the CEPRA technique according to embodiments of the invention. After 7 months, the samples were removed from the containers and left to dry for a month during which time measurements were taken weekly to analyse the effect of the increased resistivity on the results. At the end of the exposure period, a total of 8 months, the reinforcements were removed by inducing a longitudinal crack along the reinforcement using a jackhammer. The mass loss of the reinforcements was found according to Procedure C.3.5 of ASTM G1 "Standard Practice for Preparing, Cleaning, and Evaluating Corrosion Test Specimens."

FINITE ELEMENT MODELING: In order to study the current propagation behavior and the time-dependent potential during the application of the CEPRA technique, a finite element model was developed.

CONSTITUTIVE RELATIONSHIPS: In order to model the polarization behavior of the reinforcement, Faradaic and capacitive processes were assumed to apply at the steel surface. The electrochemical Faradaic kinetics governing the polarization behavior occurring at the reinforcement surface can be modeled with the use of the Butler-Volmer Equation given by Equation (6) where j is the net current density, $j_0$ is the exchange current density, η is the change in potential (Φ) from the equilibrium potential ($Φ_{EQ}$) of the electrode (Φ-$Φ_{EQ}$), $b_a$ is the anodic Tafel coefficient, and $b_c$ is the cathodic Tafel coefficient.

The effects of the charge-storage process caused by the double-layer capacitance) can be incorporated into the model assuming that the electrode surface behaves as a perfect capacitor during the charge storage or release process. The corresponding current charge/discharge at any time for such a capacitor can be represented by Equation (7)

where $C_{DL}$ is the electrode's double-layer capacitance and $\delta E/\delta t$ is the change in potential with respect to time.

$$j = j_0(10^{n/b_a} - 10^{n/b_c}) \quad (6)$$

$$j_{CAP} = C_{DL}(\delta E/\delta t) \quad (7)$$

$$j = j_0(10^{n/b_a} - 10^{n/b_c}) + C_{DL}(\delta E/\delta t) \quad (8)$$

$$j = (-1/\rho)\nabla E \quad (9)$$

$$\nabla j = 0 \quad (10)$$

Using this approach, the current at the steel-concrete interface after the application of a polarizing current is the sum of the Faradaic process (Butler-Volmer kinetics) and the capacitive currents. The total time-dependent current can then be expressed by Equation (8). In order to solve for the potential and current density distribution at the surface of the reinforcement, assuming electrical charge conservation and isotropic conductivity, Ohms law (Equation (9)), and charge conservation law (Equation (10)), are used for the concrete domain, assuming that concrete is a homogeneous medium with a uniform electrical resistivity.

Figure 24:
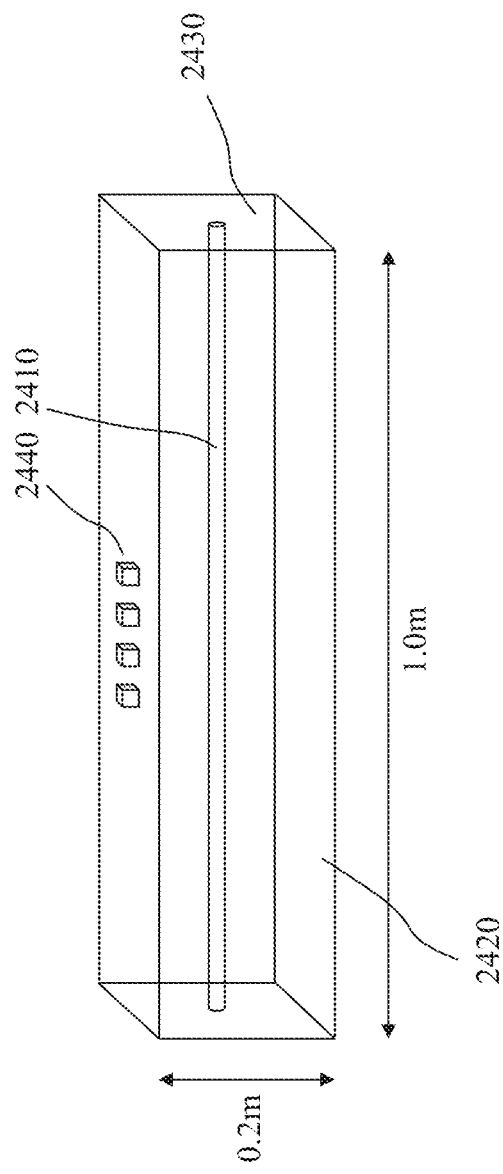
FIG. 24 depicts a domain of a finite element model employed within verifying the CEPRA technique.

FINITE ELEMENT MODELING (FEM) PROCEDURE: Three dimensional simulations were performed using a COMSOL software package. The domain of the problem is depicted in FIG. 24 wherein a reinforced concrete member 1 m in length, 0.3 m in width, and 0.2 m in height (39"×12"×8"), with a rebar embedded at a certain cover depth (variable parameter). As depicted in FIG. 24 the domain for the FEM model comprises a reinforcement surface 2410, concrete domain 2420, external boundary 2430 and probe 2440.

At the steel-concrete interface (reinforcement surface 2410), Equation (8) was employed as a Dirichlet-type boundary condition to find the time-dependent polarization behavior of the electrode. In the concrete domain (concrete domain 2420), Equations (9) and (10) were used to solve for the potential and current density distributions. External boundaries (external boundary 2430) were modeled as electrically insulated boundaries (Neumann boundary conditions with a specified normal current of zero). The CEPRA technique according to an embodiment of the invention was modeled as a Wenner array, with four probes (probe 2440) having a probe spacing of 50 mm (2") in which the two outer probes were used to apply a current of 0.5 mA and −0.5 mA. The potential difference between the inner probes was recorded using the CEPRA technique. The four probes were modeled as perfect point objects.

Solutions were performed using a MUMPS solver (MUltifrontal Massively Parallel Sparse Direct Solver) inputted in the COMSOL software which makes use of the multifrontal method Gaussian-elimination and is based on the lower-upper decomposition matrix-solving procedure. It should be noted, however, that other solvers available in the software were tried and their solutions were identical for the problem under consideration. However, the primary difference was the convergence time. The relative tolerance used was 0.001.

In such a system, the summation of the current at the reinforcement surface 2410 and at the two current-applying electrodes is expected to be zero. This was used in order to discretize the mesh and minimize errors due to the mesh elements' size and approximations. This was conducted by trying several different mesh combinations for the concrete domain and the three different boundaries as shown in FIG. 24 until the summation of current was negligible (less than 0.1% of the applied current). It was found that the optimum mesh configuration varies greatly depending on the cover depth (due to the distance between the reinforcement-surface boundary and external boundary) and concrete resistivity (due to potential gradients being different in high-resistivity systems compared to low-resistivity systems), among other factors.

MODEL INPUTS AND INVESTIGATED PARAMETERS: The model was solved for cases representing passive reinforcements and cases representing actively corroding reinforcements. This was done by changing the input parameters in the Butler-Volmer equation according to Table 22. The anodic and cathodic beta coefficients for the active case were chosen to yield a beta coefficient of 26 mV, which is the value typically used for corrosion in reinforcing steel studies within the industry. The exchange current density for the active case was adapted from that used by Marchand et al. (see "A Numerical Study of Polarization Tests Applied to Corrosion in Reinforced Concrete", ACI Special Publication, Vol. 312, 2017, pp 1-12) for the same purpose of this study. However, the effect of this parameter was studied separately. The exchange current density for the passive cases was adapted from the model outlined by Pour-Ghaz et al. (see "The Effect of Temperature in the Corrosion of Steel in Concrete. Part 1: Simulated Polarization Resistance Test and Model Development", Eur. J. Environ. Civ. Eng., Vol. 16, Nos. 3-4, 2012, pp. 491-504).

The beta coefficients for the passive case were chosen to yield a beta coefficient close to 52 mV, which is the value typically used for corrosion of reinforcing steel studies. The anodic beta for the passive case also reflects passivation control and the ineffectiveness of anodic potential polarizations in increasing the anodic current for the passive case. This number is based on the mean value obtained by the inventors. The equilibrium potentials were obtained from Pour-Ghaz whilst for each of the passive and active cases, the parameters were studied as shown in Table 3.

TABLE 2

Model Inputs for Active and Passive Cases

| Input | Passive Case | Active Case |
|---|---|---|
| $j_0$ | $10^{-5}$ A/m$^2$ | 0.1 A/m$^2$ |
| $b_a$ | 0.12 V | 0.12 V |
| $b_c$ | 0.12 V | 0.12 V |
| $\Phi_{EQ}$ | −0.78 V | −0.78 V |
| $C_{DL}$ | Variable | Variable |

TABLE 3

Parameters Investigated

| Independent Variable | Cases |
|---|---|
| Cover Depth | 20, 40, 70, and 100 mm |
| Resistivity | 20, 50, 100, 200, 500, and 1,000 ohm · cm |
| Reinforcement Diameter | 10, 20, 30 mm |
| $j_0$ (for the active case) | 0.01, 0.05, 0.1 and 0.5 A/m$^2$ |

Figure 25:
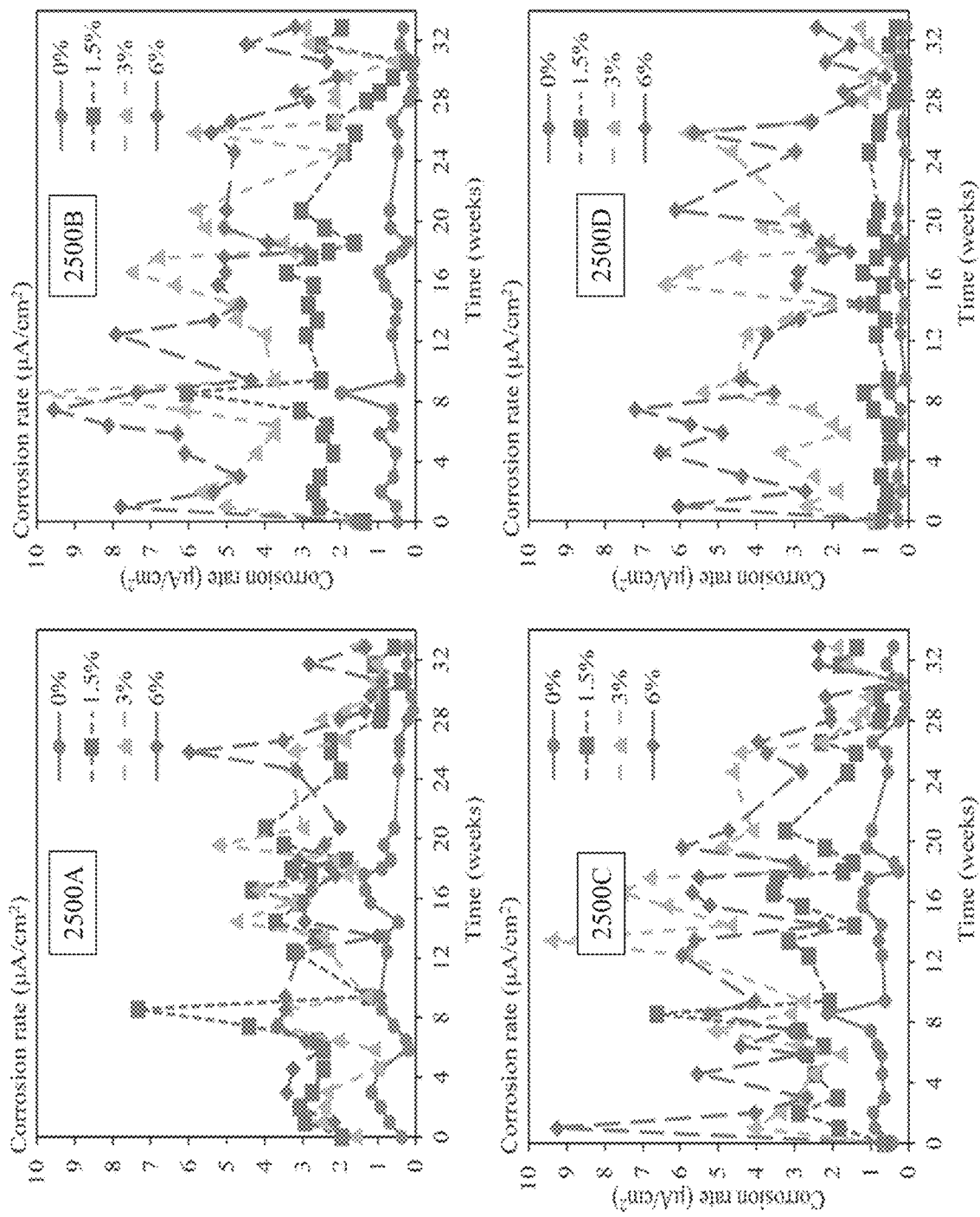
FIG. 25 depicts corrosion rate measurements obtained exploiting the CEPRA technique according to an embodiment of the invention for different experimental conditions.

EXPERIMENTAL RESULTS: Referring to FIG. 25 there are depicted first to fourth graphs 2500A to 2500D respectively for the corrosion rate measurements collected by this method throughout the exposure period. These depict:

First graph 2500A depicts the results for the 20 mm cover samples with 10M rebar;
Second graph 2500B depicts the results for the 40 mm cover samples with 10M rebar;

Third graph 2500C depicts the results for the 70 mm cover samples with 10M rebar; and Fourth graph 2500D depicts the results for the 20M rebar.

Figures 26, 28:
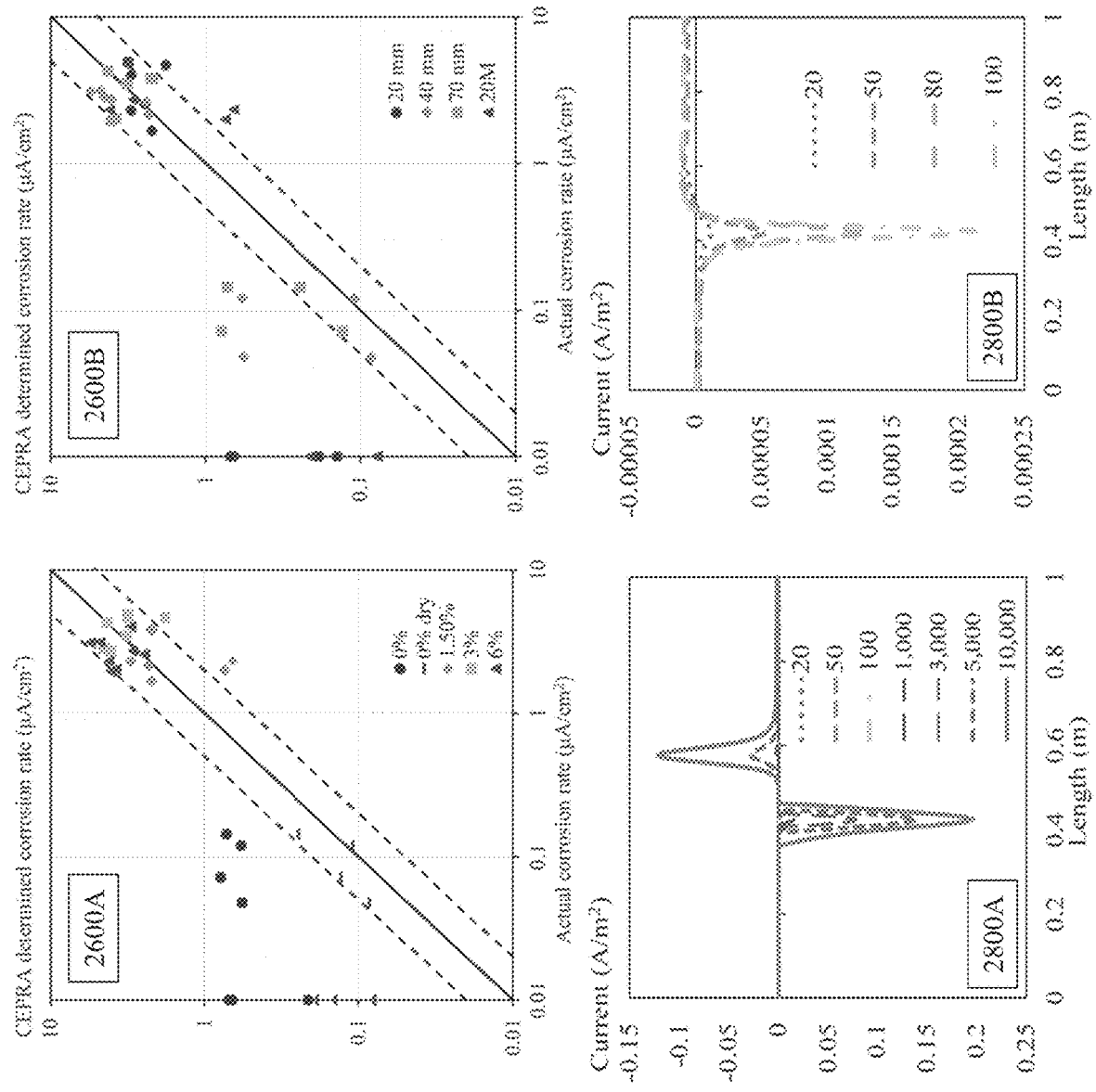
FIG. 26 depicts corrosion rate measurements obtained exploiting the CEPRA technique according to an embodiment of the invention compared to actual corrosion rates.
FIG. 28 depicts the effect of resistivity on the current distribution for the instance of a passive rebar established through simulations.

The presented results are averages of two replicate reinforcements embedded in the same concrete specimen. It is evident that the method was able to capture the effect of admixed chloride contents on the measured corrosion rates. The rebar specimens embedded in chloride-free concrete showed the lowest corrosion rates, and the corrosion rate generally was found to increase with increasing admixed chloride contents up to 3%, after which no significant increase in activity was found. Referring to FIG. 26 there are depicted first and second graphs 2600A and 2600B respectively for the weighted average corrosion rate determined by the CEPRA technique according to an embodiment of the invention plotted versus the actual corrosion rate obtained by determining the mass loss. First graph 2600A depicts the results obtained from the CEPRA technique as a factor of admixed chloride percentage whilst second graph 2600B depicts the results as a factor of cover depth or reinforcement diameter. The actual corrosion rate was obtained using the ASTM G1 procedure. The average electrochemically predicted corrosion rate was obtained by integrating the corrosion rates obtained by the technique throughout the monitoring period (depicted in FIG. 25) divided by the total period of exposure. Note that the measurements labeled dry are the average of measurements conducted during the drying month mentioned earlier on specimens with no admixed chlorides. The dashed lines within FIG. 26 depict the range of correlations accepted in the literature.

The results clearly indicate the applicability of using the CEPRA technique according to embodiments of the invention in measuring corrosion rates. For the actively corroding (specimens with admixed chlorides), the predicted corrosion rates generally agreed well with the actual corrosion rates. Results for 21 out of 24 specimens fell in the range of results typically in the literature, which is one-half to two times the actual corrosion rates. The three specimens that did not fall in the typically accepted range still showed corrosion rates that were 0.35 to 0.45 times the actual corrosion rate, which is close to the lower range. correlation is similar to, if not better than, those typically reported for well-established corrosion monitoring techniques applied for steel in concrete, especially for cases of low resistivity. The success of the CEPRA method according to embodiments of the invention is evident as the results are not affected by the reinforced concrete system characteristics in this case. This correlation was obtained similarly for a wide range of resistivities (obtained using different admixed chloride percentages), cover depths, or reinforcement diameters.

For the passive specimens (specimens without admixed chlorides) in the dry condition, the results showed corrosion rates in the range of 0.2 $\mu A/cm^2$ or less, which is in the range that is typically accepted in the literature for passive reinforcements The same reliability in determining passive corrosion rates was obtained for the case of saturated concrete with 20M reinforcements. It should also be noted that the CEPRA technique according to embodiments of the invention was obtained with a measurement time of only 6 seconds, which is much lower than the typical time required for other techniques for passive conditions. This is due to the effect of this technique in shortening the time to steady-state conditions, as demonstrated further through modeling results, and due to the exponential curve-fitting procedure used.

An overestimation of passive corrosion rates was found for the case of saturated specimens with 10M reinforcements, where the results fall in the range of 0.6 to 0.8 $\mu A/cm^2$. This is relatively higher than the range of corrosion rates expected for specimens without admixed chlorides (an order of magnitude of difference between actual and estimated corrosion rates) but is similar to results obtained for galvanostatic devices using short measurement times and non-modulated confinement, and it still allows differentiating of passive and active reinforcements. It should be noted that the specimens showing 0.6 to 0.8 $\mu A/cm^2$ in saturated conditions started to show results lower than 0.4 $\mu A/cm^2$ after 1 day of drying, which represents cases of semi saturated concrete that better resemble field cases. (Note that in the saturated condition, these specimens were allowed to dry since cast.) The substantial difference between the results obtained in the dry and saturated conditions is expected and will be discussed further through modeling results. It will be shown, through modelling, that this overestimation of rates occurs for cases of saturated, low-resistivity concrete with small-diameter reinforcements (which represents the limitation of this method), and it will be evident that the case in this study (concrete with a water-cementitious material ratio of 0.6 in saturated conditions reinforced with 10M rebar) served as a scenario compared to cases available in the field. This is evident from the good estimation of passive corrosion rates for dry, or semi saturated, concrete and for reinforcements with larger diameters in saturated concrete, which better represent field conditions.

Figure 27:
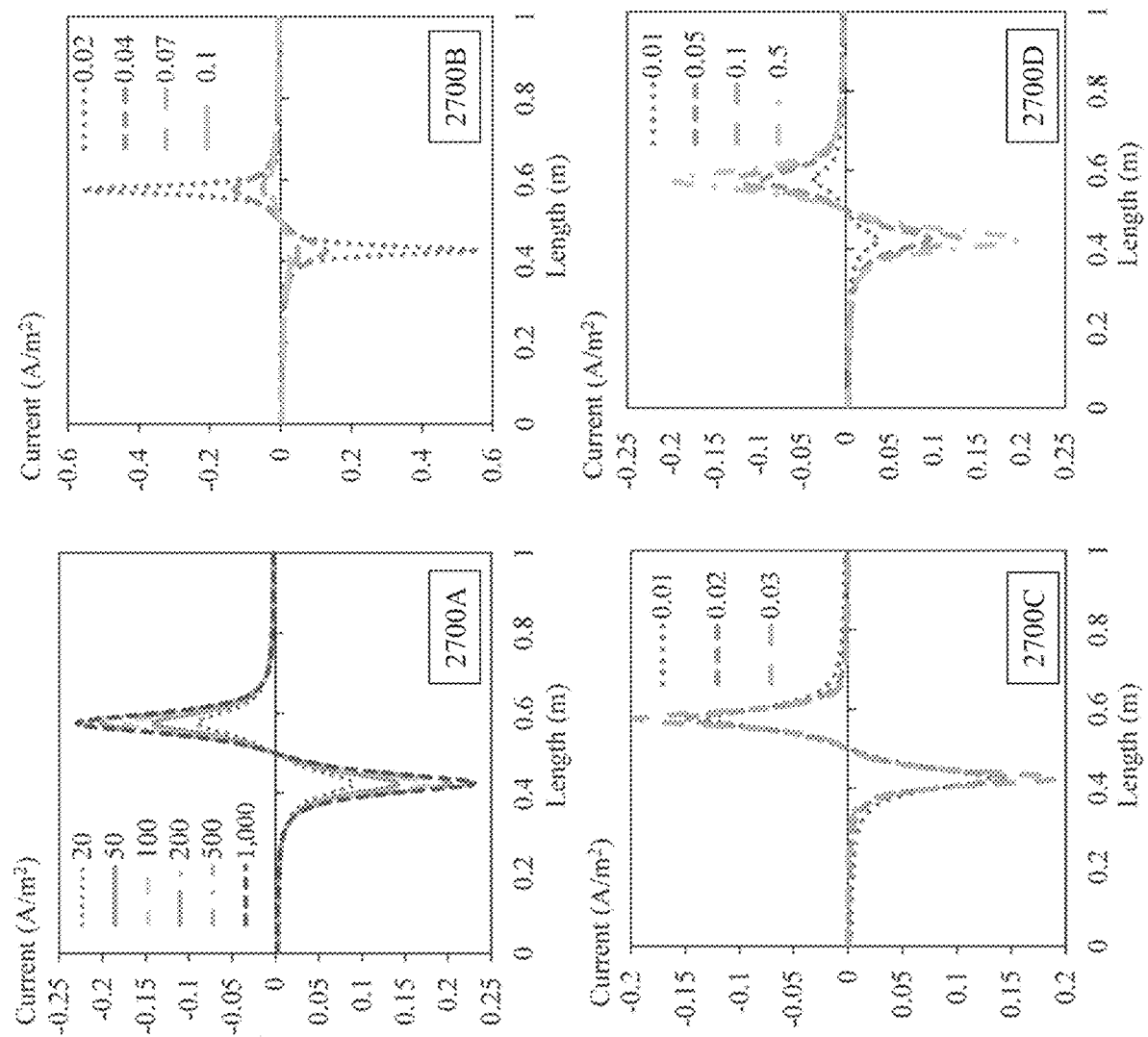
FIG. 27 depicts the influence of different experimental conditions on the distribution of the polarizing current for a uniformly corroding rebar established through simulations.

FINITE ELEMENT MODELING RESULTS: Referring to FIG. 27 there are depicted first to fourth graphs 2700A to 2700D respectively which depict modeling results on the effect of concrete resistivity, cover depth, reinforcement diameter, and exchange current density on the current distribution on the rebar surface for the case of actively corroding reinforcements. These graphs depicting, respectively:

First graph 2700A which depicts the effect of resistivity on the distribution of polarizing current for a uniformly corroding rebar;

Second graph 2700B which depicts the effect of cover depth on the distribution of polarizing current for a uniformly corroding rebar;

Third graph 2700C which depicts the effect of rebar diameter on the distribution of polarizing current for a uniformly corroding rebar; and Fourth graph 2700D which depicts the effect of exchange current density on the distribution of polarizing current for a uniformly corroding rebar;

The base case was for a cover depth of 40 mm, a resistivity of 40 ohm·m, a reinforcement diameter of 10 mm, and an exchange current density of 0.1 $A/m^2$. Each of the parameters was swept from the base case as shown. The presented results are all obtained at steady state (at a time long enough that the double-layer capacitance is charged). The negative sign indicates anodic polarization, while the positive sign indicates cathodic polarization.

The resistivity was found to influence the amount of current reaching the reinforcement in the range of low resistivities (20-200 ohm·m), where more current polarizes the reinforcement area as resistivity increases. However, in the range of higher resistivities (higher than 200 ohm·m), there was little to no influence of resistivity on the current reaching the reinforcement. The effect of resistivity on the polarizing current is simply due to the availability of two current-consumption boundaries in this technique, as opposed to one in typical three-electrode linear polarization resistance techniques. In typical techniques, any current that is applied by the counter electrode is consumed by the reinforcement if current leakage/storage is considered negligible at steady state. Within the CEPRA technique according to an embodiment of the invention, if a certain amount of current is applied from the positive (anodic) probe, it can be consumed by either the negative (cathodic) probe or in polarizing the reinforcement. As the resistivity between the two current-applying/receiving probes increases, more current preferentially polarizes the reinforcement instead of flowing between the two probes. Therefore, the current reaching the reinforcement increases as the resistivity increases. However, the polarized area shown by the CEPRA technique according to embodiments of the invention is not strongly dependent on resistivity, and confinement happens for all of the resistivities, which is very different from typical galvanostatic techniques in which confinement was found to be highly dependent on resistivity.

The effect of the cover depth showed that the current reaching the reinforcement decreases as the cover depth increases. This is because larger (higher) concrete covers allow for a larger area for the polarizing current to flow between the two current-applying probes instead of polarizing the reinforcement. For lower cover layer thicknesses, the current preferentially polarizes the reinforcement instead of flow in the electrolyte/concrete. The effect of the cover depth on the polarized area shows that lower thickness covers lead to lower polarized areas and more localized under the probe, while higher thickness covers lead to more dispersion of the applied current in the concrete cover, which is in agreement with the effect observed for other corrosion monitoring techniques This may explain the reason for the underestimation of the corrosion rate for one of the 20 mm cover depth reinforcements when assuming that the full reinforcement is polarized. The same trend is observed for the effect of the reinforcement diameter. As the reinforcement diameter increases, more current can reach the reinforcement due to a higher electrode available to consume this current. It seems that the area polarized by the technique tends to slightly decrease as the diameter increases due to the higher current consumption area available, which decreases the ability of the lateral propagation of the polarizing current. This may explain the underestimation of corrosion rate found for two of the 20M reinforcement specimens.

The influence of exchange current density, or equivalently the polarization resistance, on the area polarized by the technique is very similar to that observed for resistivity. This is because the portion of current flowing in the path polarizing the reinforcement, as opposed to that parallel to the reinforcement, is determined by the relative values of concrete resistivity and polarization resistance. Lower polarization resistances encourage more current to reach the reinforcement instead of flowing explicitly in the concrete. Nevertheless, the polarized area shown by the technique is not strongly dependent on polarization resistance (in the range of active rates), and confinement happens regardless of the polarization resistance value, which is very different from typical galvanostatic techniques in which confinement was found to be highly dependent on polarization resistance.

Although the current reaching the reinforcement is variable, it is well estimated through the model outlined above as evident by the accuracy of the technique for actively corroding reinforcements. Furthermore, these results clearly indicate that the dependency of confinement success on factors such as concrete resistivity, cover depth, reinforcement diameter, and exchange current density are marginal, and the polarized area changes with very low magnitudes. The polarization length for the CEPRA technique according to an embodiment of the invention, for the cases shown and for other cases not presented within this specification, for a wide range of concrete resistivities, cover depths, reinforcement diameters, and exchange current densities, from 50 cm (2") (in cases of very large cover depths and small diameters) to 30 cm (1.2") (in cases of very small cover depth and large reinforcement diameters). This variance in polarized area is much smaller than that found with other techniques. If, for instance, the polarized area is assumed to be 40 cm for all of these cases, the error due to this assumption will not exceed 25%. This ability to confine the polarized current, without the use of confinement techniques, stems from the current regulating nature of this technique, where the current reaching the reinforcement is variable and depends on characteristics of the steel-concrete system. This is different from prior art techniques where confinement is essential. For instance, it has been shown that achieving confinement using the guard-ring technique is very challenging in very low-resistivity systems due to the higher tendency of the polarizing current to disperse laterally. This effect does not occur in the CEPRA technique according to embodiments of the invention because the current reaching the reinforcement decreases as resistivity decreases, leading to a lower effect of resistivity on confinement success.

Referring to FIG. 28 there are depicted first and second graphs 2800A and 2800B respectively for the effect of resistivity on the current distribution for the case of passive rebar. The results were obtained for cover depths of 40 mm and 10 mm. As discussed above, higher resistivities generally lead to higher amounts of current reaching the reinforcement. For low resistivities, second graph 2800B, it was found that confinement occurs only in the branch of the reinforcement near the cathodic probe While the full reinforcement area near the probe is polarized, up to 0.5 m (20") in the cases simulated. This is simply due to the challenge of polarizing a passive electrode anodically. This is due to the electrode's very low exchange current density and the very high anodic Tafel slope (due to passivation control) leading to the reinforcement having a very limited ability to consume the anodic polarizing current. On the other hand, for cathodic polarizations, passive reinforcements tend to become better current consumers because the cathodic Tafel slope is much lower than the anodic one (if no diffusion limitation exists). This leads to a limitation of the CEPRA model due to the lack of symmetry between the two sides of the reinforcements, which means that $R_{C3}$ (Shown earlier) will not be the same under the probes ($R_{C3}$ will be identical for both sides only if the anodic and cathodic beta coefficients are equal). In the of high-resistivity systems, the symmetry is restored, and confinement occurs, which leads to a better estimate of passive corrosion rates. This can partially explain the estimate of passive corrosion rates in the cases of semi saturated and dry concrete. This limitation of confining anodic polarizations for passive electrodes is similar for all the techniques using anodic polarizations.

It should be also noted that the CEPRA model assumes that high- and frequency current-propagation behaviors follow the same path. This is important in applying the model successfully. Referring to FIG. 29 there is depicted the typical current-propagation path for the case of a passive reinforcement at the high-frequency range (obtained 1 μs after current application). This is the same path as that for the high- and low-frequency responses for active reinforcements. These paths are identical in FIG. 29 and are therefore not presented here. Now referring to FIG. 30 there is depicted the typical current-propagation path for the case of a passive reinforcement, with low-resistivity concrete (40 ohm·m), at the low-frequency range (500 seconds after current application). As mentioned previously, the high- and low-frequency paths are rather similar in cases of actively corroding electrodes (both similar to FIG. 29), which explains the validity of the model and the obtained through it. However, this is not the case for the passive reinforcement in low resistivity concrete because in the high frequency portion, the reinforcement's double layer acts as a relatively good current consumer (causing a short-circuit effect), while in the low-frequency region, this reinforcement acts as a current insulator (due to the high $R_P$) and hardly any current polarizes the reinforcement. It is evident that in the low frequency range for the passive reinforcements, the electrode tends to encourage current flow in a different path than that for the high-frequency response (around and beneath the reinforcement). The low and high-frequency current paths will tend to become increasingly similar, and subsequently provide better results, when the current polarizing the reinforcement in the low-frequency range increases. This polarizing current increases as the electrode's area available for current consumption increases or as the system resistivity increases, which explains the good results obtained for the dry or semi saturated (high-resistivity) cases, as well as cases with large reinforcement diameters (these cases better simulate field conditions). This may indicate that the overestimation found in the case of saturated, low-resistivity concrete with small-diameter passive rebar is not characteristic of the technique and only occurs in such scenarios.

Figure 31:
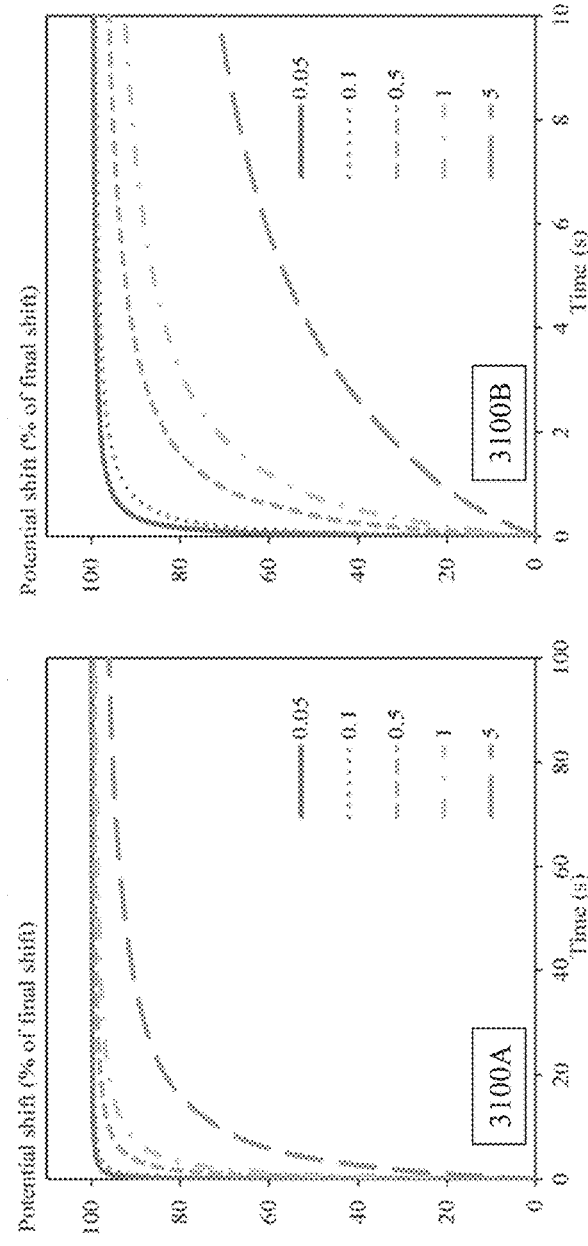
FIGS. 31 and 32 depict the effect of double layer capacitance on the obtained time transient for a passive rebar established through simulations.
Figure 32:
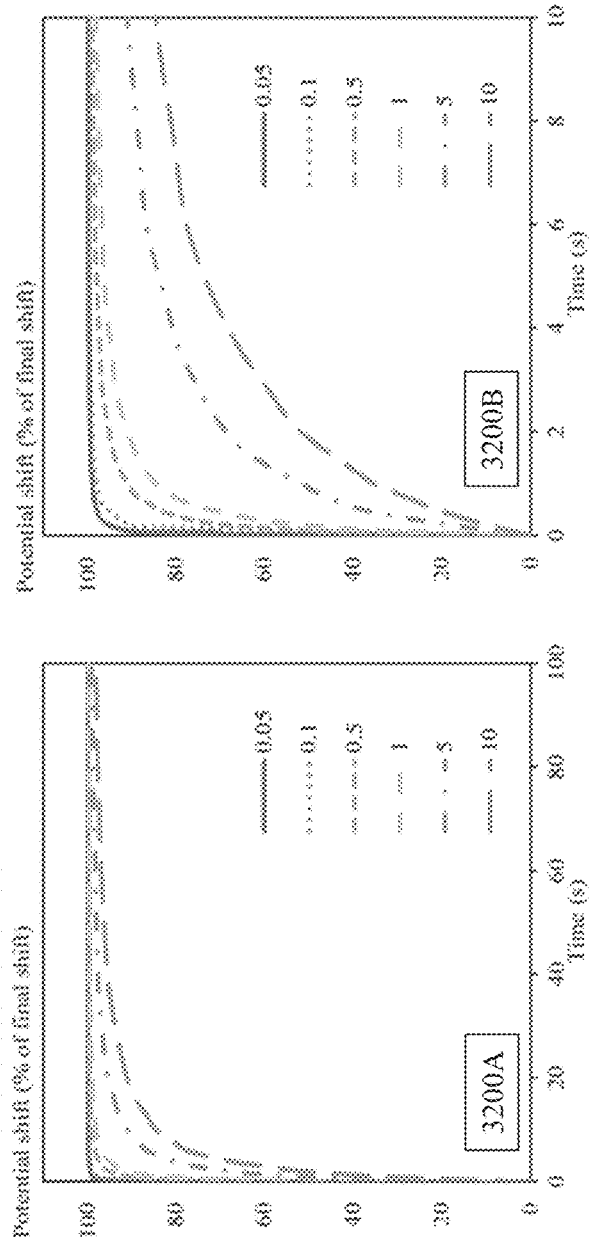

Referring to FIGS. 31 and 32 there are depicted the potential difference between the two inner probes as a factor of time for a case of resistivity of 40 ohm·m, a cover depth of 40 mm, and a reinforcement diameter of 10 mm for a passive and active rebar, respectively. It is evident that the technique reduces the time to reaching quasi-steady-state conditions compared to prior art techniques. FIG. 31 depicts first and second graphs 3100A and 3100B respectively which depict the effect of double layer capacitance on the obtained time transient for the case of a passive rebar up to 100 seconds and 10 seconds respectively. FIG. 32 depicts first and second graphs 3200A and 3200B respectively which depict the effect of double layer capacitance on the obtained time transient for the case of an active rebar up to 100 seconds and 10 seconds respectively.

A measurement time of 10 seconds was found to provide adequate information about the polarization behavior of the reinforcement up to capacitance values in the range of 1 $F/m^2$ for the passive case (88% of the steady-state polarization was achieved in 10 seconds) and 5 $F/m^2$ in the active case (91% of the steady-state was achieved in 10 seconds). The time requirement with prior art techniques has been a major challenge for determining the reinforcements corrosion rates, especially with the very low exchange current density assumed in this model ($10^{-5}$ $A/m^2$). The ability to shorten the measurement time associated with this technique has been proven experimentally, theoretically, and numerically by the current study. The primary reason for this is that the polarizing current is very low in the area found in the middle of the reinforcement. Another is the lower electrode area contributing to the polarization. However, this changes if the resistivity reaches very high values due to the higher current received by the reinforcement, where higher resistivities lead to higher times to quasi-steady-state conditions This shortening of the time to steady-state conditions leads to the CEPRA technique according to embodiments of the invention have the ability to determine corrosion rates in the passive case in only a few seconds, as evidenced by the experimental results. This ability to perform the measurements is not applicable for techniques with constant applied currents.

Figure 33:
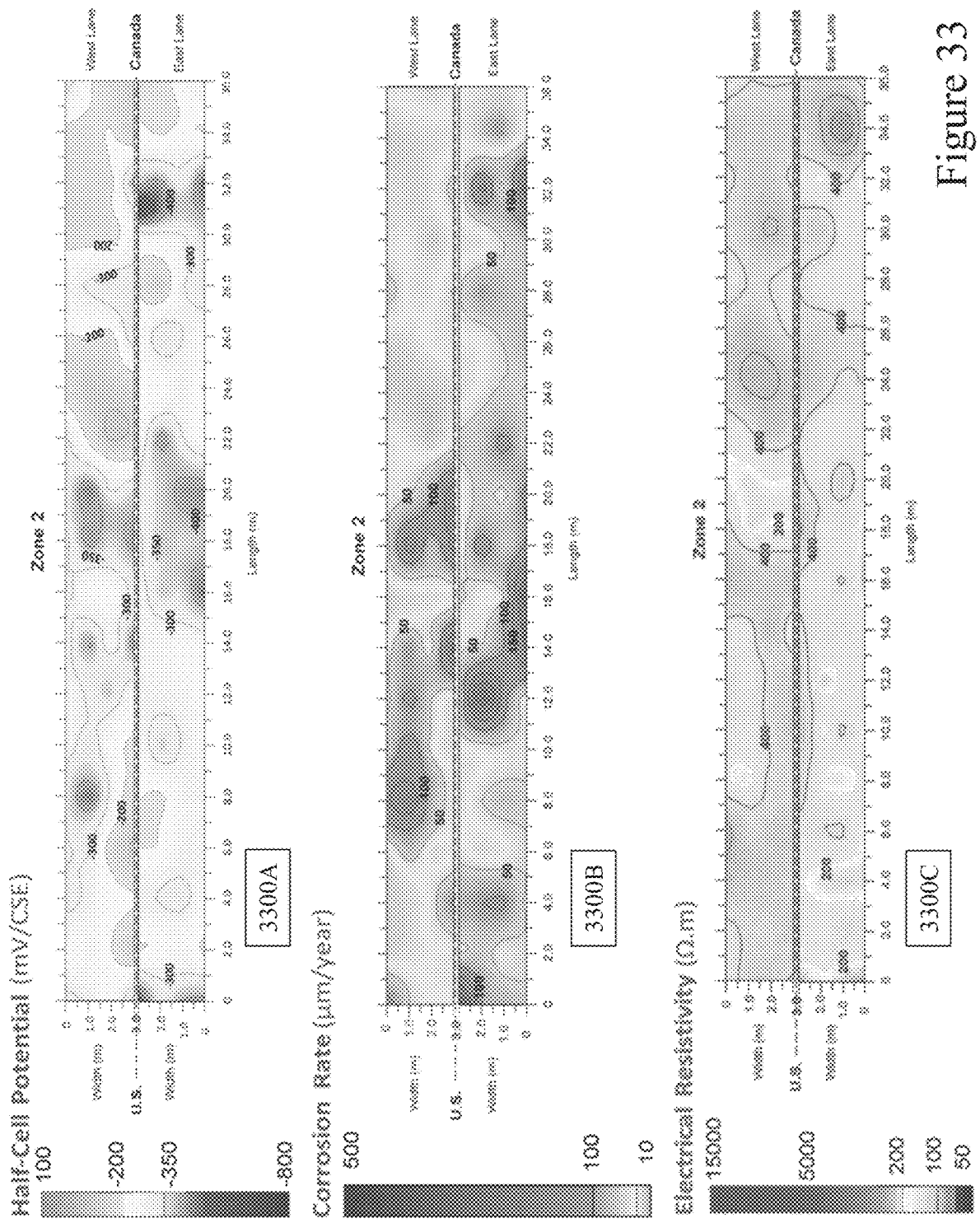
FIG. 33 depicts contour plots of the Three Nations Bridge established using the CEPRA technique according to an embodiment of the invention.

In order to demonstrate the ability of the CEPRA technique to obtain measurements rapidly measurements were performed upon the south channel bridge of Three Nations Bridge crossing between the State of New York and Cornwall, Ontario, Canada. This bridge carries international traffic of approximately 2 million vehicles per year and comprises a high level suspension bridge straddling a waterway used by large ocean going ships navigating the Saint Lawrence Seaway. Accordingly, a 36 m×6 m (approximately 120'×20') was mapped. The results are depicted in first to third plots 3300A to 3300C in FIG. 33 representing the resistivity measured, the derived corrosion potential, and the derived corrosion rate respectively. It is evident from second and third plots 3300B and 3300C respectively that both the corrosion potential and corrosion rate measurements identified similar high risk zones within the assessed section of the bridge. Table 4 below summarizes the evaluation criteria applied to the resistivity measurements to assess risk. In contrast to the normal visual inspection and chain dragging methods which are only able to detect damage when sufficient ciorrosion has occurred for the corrosion to manifest itself the CEPRA technique according to embodiments of the invention provides information on the state of corrosion at the time of the measurement even if the corrosion has not propagated enough to cause sufficient damage to be visually or acoustically observable.

TABLE 4

| Resistivity versus Corrosion State | |
|---|---|
| Resistivity (ohm · m) | Corrosion State Assessed |
| >20 | Low |
| 10-20 | Moderate |
| 5-10 | High |
| <5 | Severe |

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system may further include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alphanumeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method of performing an assessment of a predetermined characteristic of a concrete structure comprising:
    applying a narrow electrical pulse to a pair of first electrodes in contact with an area of the concrete structure containing a rebar;
    measuring a time dependent voltage response from a pair of second electrodes in line with and between the pair of first electrodes and in contact with the area of concrete structure containing the rebar;

fitting the measured time dependent voltage response to a theoretical transient to establish a fitted transient function;

determining constants of the fitted transient function; and determining one or more electrical equivalent circuit elements of an equivalent circuit model of the concrete structure containing the rebar in dependence upon the constants of the fitted transient function; and the predetermined characteristic of the concrete structure is established in dependence upon the determined one or more electrical equivalent circuit elements of the equivalent circuit model of the concrete structure.

2. The method according to claim 1, wherein
the fitted transfer function is $V_{in}(t)=V_{ex}(A-Be^{-Dt})$; and
the determined constants are A, B and D.

3. The method according to claim 1, wherein
the equivalent circuit model comprises:
  a pair of resistive elements ($R_{C1}$) between each first electrode of the pair of first electrodes and its nearest second electrode of the pair of second electrodes;
  a second resistive element ($R_{C2}$) between the pair of second electrodes; and
  a sub-circuit between the pair of second electrodes comprising:
  a pair of third resistive elements ($R_{C3}$), each third resistive element of the pair of resistive elements coupled from a second electrode of the pair of second electrodes to an end of a resistive-capacitive circuit; and
  the resistive-capacitive circuit comprising a fourth resistive element ($R_{C4}$) in parallel with a capacitive element ($C_{DL}$).

4. The method according to claim 3, further comprising
determining a cover depth of concrete above the rebar between the rebar and a device comprising the pair of first electrodes and the pair of second electrodes; and
employing the cover depth to provide an indirect measurement of a ratio of current flowing through $R_{C2}$ to that flowing through $R_{C3}$.

5. The method according to claim 1, wherein
the fitted transfer function is $V_{in}(t)=V_{ex}(A-Be^{-Dt})$;
the determined constants are A, B and D;
the equivalent circuit model comprises:
  a pair of first resistive elements ($R_{C1}$) between each first electrode of the pair of first electrodes and its nearest second electrode of the pair of second electrodes;
  a second resistive element ($R_{C2}$) between the pair of second electrodes; and
  a sub-circuit between the pair of second electrodes comprising:
  a pair of third resistive elements ($R_{C3}$), each third resistive element of the pair of resistive elements coupled from a second electrode of the pair of second electrodes to an end of a resistive-capacitive circuit; and
  the resistive-capacitive circuit comprising a fourth resistive element ($R_{C4}$) in parallel with a capacitive element ($C_{DL}$); and
the determined constant A is a function of $R_{C1}$, $R_{C2}$, $R_{C3}$, and $R_{C4}$;
the determined constant B is a function of $R_{C1}$, $R_{C2}$, $R_{C3}$, and $R_{C4}$; and
the determined constant D is a function of $R_{C1}$, $R_{C2}$, $R_{C3}$, $R_{C4}$, and $C_{DL}$.

6. The method according to claim 1, wherein
the electrical pulse is one of a DC voltage pulse and a DC current pulse.

7. The method according to claim 1, wherein
the electrical pulse is one of an AC voltage pulse and an AC current pulse.

8. The method according to claim 1, further comprising
determining a cover depth of concrete above the rebar between the rebar and a device comprising the pair of first electrodes and the pair of second electrodes; and
employing the cover depth of the concrete over the rebar in determining the one or more electrical equivalent circuit elements.

9. The method according to claim 1, wherein
the predetermined characteristic of the concrete structure is a corrosion rate of the rebar.

10. The method according to claim 1, wherein
the predetermined characteristic of the concrete structure is a resistivity of the concrete.

11. A system for performing an assessment of a predetermined characteristic of a concrete structure comprising:
a measurement device comprising:
  a pair of first electrodes configured to be placed into contact with an area of the concrete structure containing a rebar;
  a pair of second electrodes configured in line with and between the pair of first electrodes and to contact the area of the concrete structure containing the rebar whilst the pair of first electrodes are in contact with the area of the concrete structure containing the rebar;
  an electrical circuit coupled to the pair of first electrodes for generating a narrow electrical pulse to a pair of first electrodes; and
  a measurement circuit for measuring a time dependent voltage response from the pair of second electrodes; and
an analysis system executing instructions to configure the analysis system to perform a process comprising:
  receiving the measured time dependent voltage response from the measurement device;
  fitting the measured time dependent voltage response to a theoretical transient to establish a fitted transient function;
  determining constants of the fitted transient function; and
  determining one or more electrical equivalent circuit elements of an equivalent circuit model of the concrete structure containing the rebar in dependence upon the constants of the fitted transient response; and
the assessment of the predetermined characteristic of the concrete structure is established in dependence upon the determined one or more electrical equivalent circuit elements of the equivalent circuit model of the concrete structure.

12. The method according to claim 11, wherein
the fitted transfer function is $V_{in}(t)=V_{ex}(A-Be^{-Dt})$; and
the determined constants are A, B and D.

13. The method according to claim 11, wherein
the equivalent circuit model comprises:
  a pair of resistive elements ($R_{C1}$) between each first electrode of the pair of first electrodes and its nearest second electrode of the pair of second electrodes;
  a second resistive element ($R_{C2}$) between the pair of second electrodes; and
  a sub-circuit between the pair of second electrodes comprising:
  a pair of third resistive elements ($R_{C3}$), each third resistive element of the pair of resistive elements coupled from a second electrode of the pair of second electrodes to an end of a resistive-capacitive circuit; and the resistive-capacitive circuit comprising a fourth resistive element ($R_{C4}$) in parallel with a capacitive element ($C_{DL}$).

14. The method according to claim 11, wherein the fitted transfer function is $V_{in}(t)=V_{ex}(A-Be^{-Dt})$;

the determined constants are A, B and D;

the equivalent circuit model comprises:

a pair of first resistive elements ($R_{C1}$) between each first electrode of the pair of first electrodes and its nearest second electrode of the pair of second electrodes;

a second resistive element ($R_{C2}$) between the pair of second electrodes; and a sub-circuit between the pair of second electrodes comprising:

a pair of third resistive elements ($R_{C3}$), each third resistive element of the pair of resistive elements coupled from a second electrode of the pair of second electrodes to an end of a resistive-capacitive circuit; and the resistive-capacitive circuit comprising a fourth resistive element ($R_{C4}$) in parallel with a capacitive element ($C_{DL}$); and the determined constant A is a function of $R_{C1}$, $R_{C2}$, $R_{C3}$, and $R_{C4}$;

the determined constant B is a function of $R_{C1}$, $R_{C2}$, $R_{C3}$, and $R_{C4}$; and the determined constant D is a function of $R_{C1}$, $R_{C2}$, $R_{C3}$, $R_{C4}$, and $C_{DL}$.

15. The method according to claim 11, further comprising determining a cover depth of concrete above the rebar between the rebar and a device comprising the pair of first electrodes and the pair of second electrodes; and employing the cover depth to provide an indirect measurement of a ratio of current flowing through $R_{C2}$ to that flowing through $R_{C3}$.

16. The method according to claim 11, wherein the electrical pulse is one of a DC voltage pulse and a DC current pulse.

17. The method according to claim 11, wherein the electrical pulse is one of an AC voltage pulse and an AC current pulse.

18. The method according to claim 11, further comprising determining a cover depth of concrete above the rebar between the rebar and a device comprising the pair of first electrodes and the pair of second electrodes; and employing the cover depth of the concrete over the rebar in determining the one or more electrical equivalent circuit elements.

19. The method according to claim 11, wherein the predetermined characteristic of the concrete structure is either a corrosion rate of the rebar or resistivity of the concrete.

* * * * *